United States Patent
Zitnik et al.

(10) Patent No.: US 12,296,169 B2
(45) Date of Patent: *May 13, 2025

(54) BATTERYLESS IMPLANTABLE MICROSTIMULATORS

(71) Applicant: SetPoint Medical Corporation, Valencia, CA (US)

(72) Inventors: Ralph J. Zitnik, Santa Barbara, CA (US); Michael A. Faltys, Valencia, CA (US); Jacob A. Levine, West Hempstead, NY (US); Jesse M. Simon, Koh Phangan (TH)

(73) Assignee: SetPoint Medical Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/604,465

(22) Filed: Mar. 13, 2024

(65) Prior Publication Data
US 2024/0216688 A1  Jul. 4, 2024

Related U.S. Application Data

(63) Continuation of application No. 17/875,327, filed on Jul. 27, 2022, now Pat. No. 11,964,150, which is a
(Continued)

(51) Int. Cl.
*A61N 1/36* (2006.01)
*A61N 1/372* (2006.01)
(Continued)

(52) U.S. Cl.
CPC ..... *A61N 1/36053* (2013.01); *A61N 1/37205* (2013.01); *A61N 1/3756* (2013.01);
(Continued)

(58) Field of Classification Search
CPC ................ A61N 1/36053; A61N 1/37205
(Continued)

(56) References Cited

U.S. PATENT DOCUMENTS

| 2,164,121 A | 6/1939 | Pescador |
| 3,363,623 A | 1/1968 | Atwell |

(Continued)

FOREIGN PATENT DOCUMENTS

| CN | 201230913 A | 5/2009 |
| CN | 101528303 A | 9/2009 |

(Continued)

OTHER PUBLICATIONS

US 6,184,239 B1, 02/2001, Puskas (withdrawn)
(Continued)

*Primary Examiner* — Nadia A Mahmood
(74) *Attorney, Agent, or Firm* — Shay Glenn LLP

(57) ABSTRACT

Methods and apparatuses (e.g., devices and systems) for vagus nerve stimulation, including (but not limited to) sub-diaphragmatic vagus nerve stimulation. In particular, the methods and apparatuses described herein may be used to stimulate the posterior sub-diaphragmatic vagus nerve to treat inflammation and/or inflammatory disorders. The implantable microstimulators described herein may be leadless and batteryless.

20 Claims, 57 Drawing Sheets

Related U.S. Application Data continuation of application No. 16/356,906, filed on Mar. 18, 2019, now Pat. No. 11,471,681, which is a continuation-in-part of application No. 15/411,936, filed on Jan. 20, 2017, now Pat. No. 10,314,501.

(60) Provisional application No. 62/286,945, filed on Jan. 25, 2016, provisional application No. 62/286,940, filed on Jan. 25, 2016, provisional application No. 62/286,943, filed on Jan. 25, 2016, provisional application No. 62/281,029, filed on Jan. 20, 2016.

(51) Int. Cl.
*A61N 1/375* (2006.01)
*A61B 5/24* (2021.01)
*A61N 1/378* (2006.01)

(52) U.S. Cl.
CPC ............ *A61B 5/24* (2021.01); *A61N 1/36167* (2013.01); *A61N 1/37518* (2017.08); *A61N 1/378* (2013.01)

(58) Field of Classification Search
USPC .......................................................... 607/60
See application file for complete search history.

(56) References Cited

U.S. PATENT DOCUMENTS

| | | |
|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesce et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,690,693 A | 11/1997 | Wang et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Lino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Reninie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |

(56) References Cited

U.S. PATENT DOCUMENTS

| | | |
|---|---|---|
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Lasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezal et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,474 B1 | 5/2004 | Loeb et al. |
| 6,735,475 B1 | 5/2004 | Whitehurst et al. |
| 6,760,626 B1 | 7/2004 | Boveja |
| 6,762,032 B1 | 7/2004 | Nelson et al. |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezal |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,634,315 B2 | 12/2009 | Cholette |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,869 B1 | 1/2011 | Farazi |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,504,161 B1 | 8/2013 | Kornet et al. |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,989,867 B2 * | 3/2015 | Chow ............... A61N 1/0551 607/60 |
| 8,996,116 B2 | 3/2015 | Faltys et al. |
| 9,114,262 B2 | 8/2015 | Libbus et al. |
| 9,162,064 B2 | 10/2015 | Faltys et al. |

(56) References Cited

U.S. PATENT DOCUMENTS

| | | |
|---|---|---|
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 9,572,983 B2 | 2/2017 | Levine et al. |
| 9,662,490 B2 | 5/2017 | Tracey et al. |
| 9,700,716 B2 | 7/2017 | Faltys et al. |
| 9,833,621 B2 | 12/2017 | Levine |
| 9,849,286 B2 | 12/2017 | Levine et al. |
| 9,987,492 B2 | 6/2018 | Tracey et al. |
| 9,993,651 B2 | 6/2018 | Faltys et al. |
| 10,166,395 B2 | 1/2019 | Tracey et al. |
| 10,220,203 B2 | 3/2019 | Faltys et al. |
| 10,449,358 B2 | 10/2019 | Levine et al. |
| 10,561,846 B2 | 2/2020 | Tracey et al. |
| 10,583,304 B2 | 3/2020 | Faltys et al. |
| 10,596,367 B2 | 3/2020 | Faltys et al. |
| 10,695,569 B2 | 6/2020 | Levine et al. |
| 10,716,936 B2 | 7/2020 | Faltys et al. |
| 10,912,712 B2 | 2/2021 | Tracey et al. |
| 11,051,744 B2 | 7/2021 | Levine et al. |
| 11,110,287 B2 | 9/2021 | Faltys et al. |
| 11,173,307 B2 | 11/2021 | Levine et al. |
| 11,207,518 B2 | 12/2021 | Huston et al. |
| 11,260,229 B2 | 3/2022 | Manogue |
| 11,278,718 B2 | 3/2022 | Faltys et al. |
| 11,311,725 B2 | 4/2022 | Levine et al. |
| 11,344,724 B2 | 5/2022 | Huston et al. |
| 11,383,091 B2 | 7/2022 | Faltys et al. |
| 11,406,833 B2 | 8/2022 | Faltys et al. |
| 11,471,681 B2 | 10/2022 | Zitnik et al. |
| 11,547,852 B2 | 1/2023 | Levine et al. |
| 11,857,788 B2 | 1/2024 | Manogue |
| 11,890,471 B2 | 2/2024 | Levine et al. |
| 11,938,324 B2 | 3/2024 | Zanos et al. |
| 11,964,150 B2 | 4/2024 | Zitnik et al. |
| 11,969,253 B2 | 4/2024 | Levine et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1 | 2/2003 | Perreault et al. |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1 | 1/2004 | Whitehurst et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0243211 A1 | 12/2004 | Colliou et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezal |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075694 A1 | 4/2005 | Schmeling et al. |
| 2005/0075698 A1 | 4/2005 | Phillips et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |

(56) References Cited

U.S. PATENT DOCUMENTS

| | | |
|---|---|---|
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178706 A1 | 8/2006 | Lisogurski et al. |
| 2006/0190044 A1 | 8/2006 | Libbus et al. |
| 2006/0190053 A1 | 8/2006 | Dobak |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0136098 A1 | 6/2007 | Smythe et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0015659 A1 | 1/2008 | Zhang |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0166348 A1 | 7/2008 | Kupper et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234780 A1 | 9/2008 | Smith |
| 2008/0234790 A1 | 9/2008 | Bayer et al. |
| 2008/0281197 A1 | 11/2008 | Wiley et al. |

(56) References Cited

U.S. PATENT DOCUMENTS

| | | |
|---|---|---|
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0076561 A1 | 3/2009 | Libbus et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125076 A1 | 5/2009 | Shuros et al. |
| 2009/0125079 A1 | 5/2009 | Armstrong et al. |
| 2009/0131995 A1 | 5/2009 | Sloan et al. |
| 2009/0171405 A1 | 7/2009 | Craig |
| 2009/0177112 A1 | 7/2009 | Gharib et al. |
| 2009/0182388 A1 | 7/2009 | Von Arx et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2009/0281594 A1 | 11/2009 | King et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0167937 A1 | 7/2010 | Goldknopf et al. |
| 2010/0191304 A1 | 7/2010 | Scott |
| 2010/0204766 A1 | 8/2010 | Zdeblick et al. |
| 2010/0215632 A1 | 8/2010 | Boss et al. |
| 2010/0219796 A1 | 9/2010 | Kallmyer |
| 2010/0241183 A1 | 9/2010 | DiLorenzo |
| 2010/0241195 A1 | 9/2010 | Meadows et al. |
| 2010/0241207 A1 | 9/2010 | Bluger |
| 2010/0249859 A1 | 9/2010 | DiLorenzo |
| 2010/0280500 A1 | 11/2010 | Skelton et al. |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0009734 A1 | 1/2011 | Foley et al. |
| 2011/0042574 A1 | 2/2011 | Nishino et al. |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0145588 A1 | 6/2011 | Stubbs et al. |
| 2011/0152967 A1 | 6/2011 | Simon et al. |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0301658 A1 | 12/2011 | Yoo et al. |
| 2011/0301667 A1 | 12/2011 | Olson et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2012/0296176 A1 | 11/2012 | Herbst |
| 2012/0302821 A1 | 11/2012 | Burnett |
| 2013/0013016 A1 | 1/2013 | Diebold |
| 2013/0018439 A1 | 1/2013 | Chow et al. |
| 2013/0066392 A1 | 3/2013 | Simon et al. |
| 2013/0066395 A1 | 3/2013 | Simon et al. |
| 2013/0071390 A1 | 3/2013 | Stadheim et al. |
| 2013/0150756 A1 | 6/2013 | Vitek et al. |
| 2013/0245718 A1 | 9/2013 | Birkholz et al. |
| 2013/0278226 A1 | 10/2013 | Cong et al. |
| 2013/0289385 A1 | 10/2013 | Lozano et al. |
| 2013/0317580 A1 | 11/2013 | Simon et al. |
| 2014/0046407 A1 | 2/2014 | Ben-Ezra et al. |
| 2014/0070761 A1 | 3/2014 | Labbe et al. |
| 2014/0105255 A1 | 4/2014 | Kutner |
| 2014/0206945 A1 | 7/2014 | Liao |
| 2014/0213926 A1 | 7/2014 | Vaidyanathan |
| 2014/0257425 A1 | 9/2014 | Arcot-Krishnamurthy et al. |
| 2014/0277260 A1 | 9/2014 | Khalil et al. |
| 2014/0288551 A1 | 9/2014 | Bharmi et al. |
| 2014/0324118 A1 | 10/2014 | Simon et al. |
| 2014/0330335 A1 | 11/2014 | Errico et al. |
| 2014/0371818 A1 | 12/2014 | Bond et al. |
| 2015/0018728 A1 | 1/2015 | Gross et al. |
| 2015/0119956 A1 | 4/2015 | Libbus et al. |
| 2015/0133717 A1 | 5/2015 | Ghiron et al. |
| 2015/0180271 A1 | 6/2015 | Angara et al. |
| 2015/0196767 A1 | 7/2015 | Ahmed |
| 2015/0202446 A1 | 7/2015 | Franke et al. |
| 2015/0233904 A1 | 8/2015 | Nayak |
| 2015/0241447 A1 | 8/2015 | Zitnik et al. |
| 2016/0089540 A1 | 3/2016 | Bolea |
| 2016/0250097 A9 | 9/2016 | Tracey et al. |
| 2016/0279435 A1 | 9/2016 | Hyde et al. |
| 2016/0331952 A1 | 11/2016 | Faltys et al. |
| 2016/0367808 A9 | 12/2016 | Simon et al. |
| 2017/0189699 A1 | 7/2017 | Dellamano et al. |
| 2017/0202467 A1 | 7/2017 | Zitnik et al. |
| 2017/0239484 A1 | 8/2017 | Ram Rakhyani et al. |
| 2017/0245379 A1 | 8/2017 | Kang |
| 2017/0254818 A1 | 9/2017 | Haskins et al. |
| 2017/0304621 A1 | 10/2017 | Malbert et al. |
| 2017/0361093 A1 | 12/2017 | Yoo et al. |
| 2018/0021580 A1 | 1/2018 | Tracey et al. |
| 2018/0078769 A1 | 3/2018 | Dinsmoor et al. |
| 2018/0085578 A1 | 3/2018 | Rennaker, II et al. |
| 2018/0117320 A1 | 5/2018 | Levine et al. |
| 2018/0289970 A1 | 10/2018 | Faltys et al. |
| 2019/0010535 A1 | 1/2019 | Pujol Onofre et al. |
| 2019/0022389 A1 | 1/2019 | Leonhardt |
| 2019/0030334 A1 | 1/2019 | Lerman et al. |
| 2019/0054295 A1 | 2/2019 | Pannu et al. |
| 2019/0090358 A1 | 3/2019 | Aresta et al. |
| 2019/0111263 A1 | 4/2019 | Levine et al. |
| 2019/0192847 A1 | 6/2019 | Faltys et al. |
| 2019/0209844 A1 | 7/2019 | Estellar et al. |
| 2019/0290902 A1 | 9/2019 | Romero-Ortega et al. |
| 2020/0078589 A1 | 3/2020 | Simon et al. |
| 2020/0171312 A1 | 6/2020 | Dinsmoor et al. |
| 2020/0384259 A1 | 12/2020 | Chasensky et al. |
| 2021/0121696 A1 | 4/2021 | Parker et al. |
| 2021/0251848 A1 | 8/2021 | Tracey et al. |
| 2021/0353949 A1 | 11/2021 | Faltys et al. |
| 2022/0072309 A9 | 3/2022 | Levine et al. |
| 2022/0118257 A1 | 4/2022 | Huston et al. |
| 2022/0193413 A1 | 6/2022 | Levine et al. |
| 2022/0212001 A1 | 7/2022 | Faltys et al. |
| 2022/0212012 A1 | 7/2022 | Manogue |
| 2022/0257941 A1 | 8/2022 | Levine et al. |
| 2022/0280797 A1 | 9/2022 | Faltys et al. |
| 2023/0019961 A1 | 1/2023 | Huston et al. |
| 2023/0158301 A1 | 5/2023 | Levine et al. |
| 2023/0241387 A1 | 8/2023 | Levine et al. |
| 2023/0321445 A1 | 10/2023 | Zanos et al. |
| 2024/0042201 A1 | 2/2024 | Huston et al. |
| 2024/0215900 A1 | 7/2024 | Levine et al. |
| 2024/0299745 A1 | 9/2024 | Levine et al. |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| DE | 2628045 A1 | 1/1977 |
| DE | 3736664 A1 | 5/1989 |
| DE | 20316509 U1 | 4/2004 |
| EP | 0438510 B1 | 8/1996 |

(56) References Cited

FOREIGN PATENT DOCUMENTS

| | | |
|---|---|---|
| EP | 0726791 B1 | 6/2000 |
| EP | 1001827 B1 | 1/2004 |
| EP | 2213330 A2 | 8/2010 |
| EP | 2073896 B1 | 10/2011 |
| EP | 3470111 A1 | 4/2019 |
| GB | 04133 | 2/1910 |
| GB | 2073428 A | 10/1981 |
| JP | 2017502787 | 1/2017 |
| JP | 2019517830 | 6/2019 |
| KR | 20050039445 A | 4/2005 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |
| WO | WO2015/009907 A1 | 1/2015 |
| WO | WO2016/134197 A1 | 8/2016 |
| WO | WO2019/204884 A1 | 10/2019 |

OTHER PUBLICATIONS

Gautron et al.; Neurobiology of inflammation-associated anorexia; Frontiers in Neuroscience; 3(59); 10 pages; Jan. 8, 2010.
Abraham, Coagulation abnormalities in acute lung injury and sepsis, Am. J. Respir. Cell Mol. Biol., vol. 22(4), pp. 401-404, Apr. 2000.
Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.
Anderson et al.; Reflex principles of immunological homeostasis; Annu. Rev. Immunol.; 30; pp. 313-335; Apr. 2012.
Antonica, A., et al., Vagal control of lymphocyte release from rat thymus, J. Auton. Nerv. Syst., vol. 48(3), pp. 187-197, Aug. 1994.
Asakura et al., Non-surgical therapy for ulcerative colitis, Nippon Geka Gakkai Zasshi, vol. 98, No. 4, pp. 431-437, Apr. 1997 (abstract only).
Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.
Ben-Noun et al.; Neck circumference as a simple screening measure for identifying overweight and obese patients; Obesity Research; vol. 9; No. 8; pp. 470-477; Aug. 8, 2001.
Benoist, et al., "Mast cells in autoimmune disease" Nature., vol. 420(19): pp. 875-878, Dec. 2002.
Benthem et al.; Parasympathetic inhibition of sympathetic neural activity to the pancreas; Am.J.Physiol Endocrinol.Metab; 280(2); pp. E378-E381; Feb. 2001.
Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression in shock, New York Surgical Society, New York, NY, Apr. 11, 2001.
Bernik, et al., Pharmacological stimulation of the cholinergic anti-inflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oedema in rats, Res. Esp. Med. Vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status, Br. J. Anaesth., vol. 77(1), pp. 110-117, Jul. 1996.
Blum, A. et al., Role of cytokines in heart failure, Am. Heart J., vol. 135(2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to Shock, vol. 11, 1999, Molecular, cellular, and systemic pathobioligal aspects and therapeutic approaches, abstacts and program, Fourth international Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.
Bulloch et al.; Characterization of choline O-acetyltransferase (ChAT) in the BALB/C mouse spleen; Int.J.Neurosci .; 76(1-2); pp. 141-149; May 1994.
Bumgardner, G. L. et al., Transplantation and cytokines, Seminars in Liver Disease, vol. 19, No. 2, Thieme Medical Publishers; pp. 189-204, © 1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.

(56) References Cited

OTHER PUBLICATIONS

Cano et al.; Characterization of the central nervous system innervation of the rat spleen using viral transneuronal tracing; J.Comp Neurol.; 439(1); pp. 1-18; Oct. 2001.
Caravaca et al.; A novel flexible cuff-like microelectrode for dual purpose, acute and chronic electrical interfacing with the mouse cervical vagus nerve; Journal of Neural Engineering; 14(6);066005; Nov. 1, 2017.
Carteron, N. L., Cytokines in rheumatoid arthritis: trials and tribulations, Mol. Med. Today, vol. 6(8), pp. 315-323, Aug. 2000.
Cavaillon et al.; The pro-inflammatory cytokine casade; Immune Response in the Critically Ill; Springer-Verlag Berlin Hiedelberg; pp. 37-66; Jan. 21, 2002.
Cheyuo et al.; The parasympathetic nervous system in the quest for stroke therapeutics; J. Cereb. Blood Flow Metab.; 31(5);pp. 1187-1195; May 2011.
Cicala et al., "Linkage between inflammation and coagulation: An update on the molecular basis of the crosstalk," Life Sciences, vol. 62(20); pp. 1817-1824, Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroImmunoModulation, vol. 12(5), pp. 307-309, Sep. 2005.
Crusz et al.; Inflammation and cancer; advances and new agents; Nature reviews Clinical Oncology; 12(10); pp. 584-596; doi: 10.1038/nrclinonc.2015.105; Jun. 30, 2015.
Dake; Chronic cerebrospinal venous insufficiency and multiple sclerosis: Hostory and background; Techniques Vasc. Intervent. Radiol.; 15(2); pp. 94-100; Jun. 2012.
Das, Critical advances in spticemia and septic shock, Critical Care, vol. 4, pp. 290-296, Sep. 7, 2000.
De Jonge et al.; Stimulation of the vagus nerve attenuates macrophage activation by activating the Jak2-STAT3 signaling pathway; Nature Immunology; 6(8); pp. 844-851; Aug. 2005.
Del Signore et al; Nicotinic acetylcholine receptor subtypes in the rat sympathetic ganglion: pharmacological characterization, subcellular distribution and effect of pre- and postganglionic nerve crush; J. Neuropathol.Exp.Neurol.; 63(2); pp. 138-150; Feb. 2004.
Diamond et al.; Mapping the immunological homunculus; Proc. Natl. Acad. Sci. USA; 108(9); pp. 3461-3462; Mar. 1, 2011.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, Faseb J., vol. 8, No. 15, pp. 1314-1325, Dec. 1994.
Dorr et al.; Effect of vagus nerve stimulation on serotonergic and noradrenergic transmission; J. Pharmacol. Exp. Ther.; 318(2); pp. 890-898; Aug. 2006.
Doshi et al., Evolving role of tissue factor and its pathway inhibitor, Crit. Care Med., vol. 30, suppl. 5, pp. S241-S250, May 2002.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Ellington et al., In vitro selection of RNA molecules that bind specific ligands, Nature, vol. 346, pp. 818-822, Aug. 30, 1990.
Ellrich et al.; Transcutaneous vagus nerve stimulation; Eur. Neurological Rev.; 6(4); pp. 254-256; Winter 2011.
Emery et al.; Rituximab versus an alternative TNF inhibitor in patients with rheumatoid arthritis who failed to respond to a single previous TNF inhibitor: switch-ra, a global, oberservational, comparative effectiveness study; Annals of the Rheumatic Diseases; 4(6); pp. 979-984; Jun. 2015.
Engineer et al.; Directing neural plasticity to understand and treat tinnitus; Hear. Res.; 295; pp. 58-66; Jan. 2013.
Engineer et al.; Reversing pathological neural activity using targeted plasticity; Nature; 470(7332); pp. 101-104; Feb. 3, 2011 (Author Manuscript).
Esmon, The protein C pathway, Crit. Care Med., vol. 28, suppl. 9, pp. S44-S48, Sep. 2000.
Fields; New culprits in chronic pain; Scientific American; pp. 50-57; Nov. 2009.
Fleshner, M., et al., Thermogenic and corticosterone responses to intravenous cytokines (IL-1? and TNF -?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gao et al.; Investigation of specificity of auricular acupuncture points in regulation of autonomic function in anesthetized rats; Autonomic Neurosc.; 138(1-2); pp. 50-56; Feb. 29, 2008.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(-)-ET 126: A potent and selective M1 antagonist in vitro and in vivo, Life Sciences, vol. 58, No. 12, pp. 991-1000, Feb. 1996.
Ghia, et al., The vagus nerve: a tonic inhibitory influence associated with inflammatory bowel disease in a murine model, Gastroenterology, vol. 131, No. 4, pp. 1122-1130, Oct. 2006.
Giebelen, et al., Stimulation of ?7 cholinergic receptors inhibits lipopolysaccharide-induced neutrophil recruitment by a tumor necrosis factor ?-independent mechanism, Shock, vol. 27, No. 4, pp. 443-447, Apr. 2007.
Gottenberg et al.; Non-TNF-targeted biologic vs a second anti-TNF drug to treat theumatoid arthritis in patients with insufficient response to a first anti TNF drug: a randomized clinical trial; JAMA; 316(11); pp. 1172-1180; Sep. 2016.
Goyal et al., Nature of the vagal inhibitory innervation to the lower esophageal sphincter, Journal of Clinical Investigation, vol. 55, pp. 1119-1126, May 1975.
Gracie, J. A., et al., A proinflammatory role for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Groves et al.; Recordings from the rat locus coeruleus during acute vagal nerve stimulation in the anaesthetised rat; Neuroscience Letters; 379(3); pp. 174-179; May 13, 2005.
Guarente, Leonard, Ph. D.; Sirtuins, Aging, and Medicine; N Engl J Med ; vol. 364:pp. 2235-2244; Jun.-2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; pp. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.

(56) References Cited

OTHER PUBLICATIONS

Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; Jul. 1980.
Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Housley et al.; Biomarkers in multiple sclerosis; Clinical Immunology; 161(1); pp. 51-58; Nov. 2015.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monocular cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby-Year Book, inc., St. Louis, MO, US, pp. 930-937, Nov. 1, 1999.
Jacob et al.; Detrimental role of granulocyte-colony stimulating factor in neuromyelitis optica: clinical case and histological evidence; Multiple Sclerosis Journal; 18(12); pp. 1801-1803; Dec. 2012.
Jaeger et al., The structure of HIV-1 reverse transcriptase complexed with an RNA pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.
Joshi et al., Potent inhibition of human immunodeficiency virus type 1 replection by template analog reverse transcriptase, J. Virol., 76(13), pp. 6545-6557, Jul. 2002.
Kalishevskaya et al. "The character of vagotomy-and atropin-induced hypercoagulation," Sechenov Physiological Journal of the USSR, 65(3): pp. 398-404, Mar. 1979.
Kalishevskaya et al.; Nervous regulation of the fluid state of the blood; Usp. Fiziol. Nauk;, vol. 13; No. 2; pp. 93-122; Apr.-Jun. 1982.
Kanai, T. et al., Interleukin-18 and Crohn's disease, Digestion, vol. 63, suppl. 1, pp. 37-42; 2001 (year of pub. sufficiently earlier than effective US filing date and any foreign priority date).
Katagiri, M., et al., Increased cytokine production by gastric mucosa in patients with helicobacter pylori infection, J. Clin, Gastroenterol., vol. 25, Suppl. 1, pp. S211-S214, 1997.
Katsavos et al.; Biomarkers in multiple sclerosis: an up-to-date overview; Multiple Sclerosis International; vol. 2013, Article ID 340508, 20 pages; Jan. 1, 2013.

Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kawashima, et al., Extraneuronal cholinergic system in lymphocytes, Pharmacology & Therapeutics, vol. 86, pp. 29-48, Apr. 2000.
Kees et al; Via beta-adrenoceptors, stimulation of extrasplenic sympathetic nerve fibers inhibits lipopolysaccharide-induced TNF secretion in perfused rat spleen; J.Neuroimmunol .; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep. 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.
Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.
Koopman et al.; Pilot study of stimulation of the cholinergic anti-inflammatory pathway with an implantable vagus nerve stimulation device in patients with rheumatoid arthritis; 2012 ACR/ARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only); on Sep. 24, 2020.
Koopman et al.; THU0237 first-in-human study of vagus nerve stimulation for rheumatoid arthritis: clinical and biomarker results through day 84; Annals of the Rheumatic Diseases; 72(Suppl 3):A245; Jun. 1, 2013 (Abstract Only).
Koopman et al.; Vagus nerve stimulation inhibits cytokine production and attenuates disease severity in rheumatoid arthritis; Proceedings of the National Academy of Sciences; 113(29); pp. 8284-8289; Jul. 19, 2016.
Krarup et al.; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, Shock, vol. 5, No. 5, pp. 385-388, May 1996.
Kuznik, "Role of the vascular wall in the process of hemostatis," Usp Sovrem Biol., vol. 75(1): pp. 61-85; 1973 (the year of publication is sufficiently earlier than the effective U.S. filing date and any foreign priority date so that the particular month of publication is not in issue).
Kuznik, et al., "Blood Coagulation in stimulation of the vagus nerve in cats," Biull. Eskp. Biol. Med., vol. 78(7): pp. 7-9; 1974 (the year of publication is sufficiently earlier than the effective U.S. filing date and any foreign priority date so that the particular month of publication is not in issue).
Kuznik, et al., "Heart as an efferent regulator of the process of blood coagulation and fibrinolysis," Kardiologiia, vol. 13(3): pp. 10-17; 1973 (the year of publication is sufficiently earlier than the effective U.S. filing date and any foreign priority date so that the particular month of publication is not in issue).

(56) References Cited

OTHER PUBLICATIONS

Kuznik, et al., "Role of the heart and vessels in regulating blood coagulation and fibrinolysis," Kagdiologiia, vol. 13(4): pp. 145-154, Apr. 1973.

Kuznik, et al., "Secretion of blood coagulation factors into saliva under conditions of hypo-and hypercoagulation," Voprosy Meditsinskoi Khimii, vol. 19(1): pp. 54-57; 1973(the year of publication is sufficiently earlier than the effective U.S. filing date and any foreign priority date so that the particular month of publication is not in issue).

Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.

Kuznik, et al., "The role of the vascular wall in the mechanism of control of blood coagulation and fibrinolysis on stimulation of the vagus nerve," Cor Vasa, vol. 17(2): pp. 151-158; 1975 (the year of publication is sufficiently earlier than the effective U.S. filing date and any foreign priority date so that the particular month of publication is not in issue).

Lang, et al., "Neurogienic control of cerebral blood flow," Experimental Neurology, 43(1): pp. 143-161, Apr. 1974.

Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.

LeNovere, N. et al., Molecular evolution of the nicotinic acetylcholine receptor: an example of multigene family in excitable cells, J. Mol. Evol., 40, pp. 155-172, Feb. 1995.

Leonard, S. et al., Neuronal nicotinic receptors: from structure to function, Nicotine & Tobacco Res. 3:203-223, Aug. 2001.

Lips et al.; Coexpression and spatial association of nicotinic acetylcholine receptor subunits alpha7 and alpha10 in rat sympathetic neurons; J.Mol. Neurosci .; 30; pp. 15-16; Feb. 2006.

Lipton, J. M. et al.; Anti-inflammatory actions of the neuroimmunomodulator ?-MSH, Immunol. Today, vol. 18, pp. 140-145, Mar. 1997.

Loeb et al.; Cuff electrodes for chronic stimulation and recording of peripheral nerve activity; Journal of Neuroscience Methods; vol. 64; pp. 95-103; Jan. 1996.

Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.

Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).

Martindale: The Extra Pharmacopoeia; 28th Ed. London; The Pharmaceutical Press; pp. 446-485; © 1982.

Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.

Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.

McGuinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.

Miguel-Hidalgo, J.J.; The role of glial cells in drug abuse; Current Drug Abuse Reviews; vol. 2; No. 1; pp. 76-82; Jan. 2009.

Milligan et al.; Pathological and protective roles of glia in chronic pain; Nat Rev Neurosci.; vol. 10; No. 1; pp. 23-26; Jan. 2009.

Minnich et al.; Anti-cytokine and anti-inflammatory therapies for the treatment of severe sepsis: progress and pitfalls; Proceedings of the Nutrition Society; vol. 63(3); pp. 437-441; Aug. 2004.

Mishchenko, et al., "Coagulation of the blood and fibrinolysos in dogs during vagal stimulation," Sechenov Physiological Journal of the USSR, vol. 61(1): pp. 101-107, 1975.

Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.

Molina et al., CNI-1493 attenuates hemodynamic and pro-inflammatory responses to LPS, Shock, vol. 10, No. 5, pp. 329-334, Nov. 1998.

Monaco et al.; Anti-TNF therapy:past,present, and future; International Immunology; 27(1); pp. 55-62; Jan. 2015.

Nadol et al., "Surgery of the Ear and Temporal Bone," Lippinkott Williams & Wilkins, 2nd Ed., 2005, (Publication date: Sep. 21, 2004), p. 580.

Nagashima et al., Thrombin-activatable fibrinolysis inhibitor (TAFI) deficiency is compatible with murine life, J. Clin. Invest., 109, pp. 101-110, Jan. 2002.

Nathan, C. F., Secretory products of macrophages, J. Clin. Invest., vol. 79(2), pp. 319-326, Feb. 1987.

Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.

Navzer et al.; Reversing pathological neural activity using targeted plasticity; Nature; 470(7332); pp. 101-104; Feb. 3, 2011.

Neuhaus et al.; P300 is enhanced in responders to vagus nerve stimulation for treatment of major depressive disorder; J. Affect. Disord.; 100(1-3); pp. 123-128; Jun. 2007.

Noguchi et al., Increases in Gastric acidity in response to electroacupuncture stimulation of hindlimb of anesthetized rats, Jpn. J. Physiol., 46(1), pp. 53-58, Feb. 1996.

Norton, Can ultrasound be used to stimulate nerve tissue, BioMedical Engineering OnLine, 2(1), pp. 6, Mar. 4, 2003.

Olofsson et al.; Rethinking inflammation: neural circuits in the regulation of immunity; Immunological Reviews; 248(1); pp. 188-204; Jul. 2012.

Olofsson et al.; Single-pulse and unidirectional electrical activation of the cervical vagus nerve reduces tumor necrosis factor in endotoxemia; Bioelectronic Medicine; 2(1); pp. 37-42; Jun. 2015.

Oshinsky et al.; Non-invasive vagus nerve stimulation as treatment for trigeminal allodynia; Pain; 155(5); pp. 1037-1042; May 2014.

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.

Palov et al.; The cholinergic anti-inflammatory pathway: a missing link in neuroimmunomodulation; Molecular Medicine; 9(5); pp. 125-134; May 2003.

Pateyuk, et al., "Treatment of Botkin's disease with heparin," Klin. Med., vol. 51(3): pp. 113-117, Mar. 1973.

Pavlov et al.; The cholinergic anti-inflammatory pathway; Brain, Behavior, and Immunity; 19; p. 493-499; Nov. 2005.

Pavlov et al.; Controlling inflammation: the cholinergic anti-inflammatory pathway; Biochem. Soc. Trans.; 34(Pt 6); pp. 1037-1040; Dec. 2006.

Payne, J. B. et al., Nicotine effects on PGE2 and IL-1 beta release by LPS-treated human monocytes, J. Perio. Res., vol. 31, No. 2, pp. 99-104, Feb. 1996.

Peuker; The nerve supply of the human auricle; Clin. Anat .; 15(1); pp. 35-37; Jan. 2002.

Pongratz et al.; The sympathetic nervous response in inflammation; Arthritis Research and Therapy; 16(504); 12 pages; retrieved from the internet (http://arthritis-research.com/content/16/6/504) ; Jan. 2014.

Prystowsky, J. B. et al., Interleukin-1 mediates guinea pig gallbladder inflammation in vivo, J. Surg. Res., vol. 71, No. 2, pp. 123-126, Aug. 1997.

Pulkki, K. J., Cytokines and cardiomyocyte death, Ann. Med., vol. 29(4), pp. 339-343, Aug. 1997.

Pullan, R. D., et al., Transdermal nicotine for active ulceratiive colitis, N. Engl. J. Med., vol. 330, No. 12, pp. 811-815, Mar. 24, 1994.

(56) References Cited

OTHER PUBLICATIONS

Pulvirenti et al.; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Rendas-Baum et al.; Evaluating the efficacy of sequential biologic therapies for rheumatoid arthritis patients with an inadequate response to tumor necrosis factor -alpha inhibitors; Arthritis research and therapy; 13; R25; 15 pages; ; Feb. 2011.
Rinner et al.; Rat lymphocytes produce and secrete acetylcholine in dependence of differentiation and activation; J.Neuroimmunol .; 81(1-2); pp. 31-37; Jan. 1998.
Robinson et al.; Studies with the Electrocardiogram the Action of the Vagus Nerve on the Human Heart; J Exp Med; 14(3):217-234; Sep. 1911.
Romanovsky, A. A., et al., The vagus nerve in the thermoregulatory response to systemic inflammation, Am. J. Physiol., vol. 273, No. 1 (part 2), pp. R407-R413, Jul. 1, 1997.
Rosas-Ballina et al.; Acetylcholine-synthesizing T cells relay neural signals in a vagus nerve circuit Science; 334(6052); pp. 98-101; 10 pages; (Author Manuscript); Oct. 2011.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, Jul. 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.

Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95(1), pp. 31-35, Sep. 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373; Feb. 1969.
Strojnik et al.; Treatment of drop foot using and implantable peroneal underknee stimulator; Scand. J. Rehab. Med.; vol. 19(1); pp. 37R43; Dec. 1986.
Strowig et al.; Inflammasomes in health and disease; Nature; vol. 481; pp. 278-286; doi: 10.1038/nature10759; Jan. 19, 2012.
Sugano et al., Nicotine inhibits the production of inflammatory mediators in U937 cells through modulation of nuclear factor-kappaß activation, Biochemical and Biophysical Research Communications, vol. 252, No. 1, pp. 25-28, Nov. 9, 1998.
Suter et al.; Do glial cells control pain?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparison between chinese blended medicine "Shoseiryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and amold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J. et al., Shock and tissue injury induced by recombinant human cachectin, Science, vol. 234, pp. 470-474, Oct. 24, 1986.
Tracey, K. J.; Reflex control of immunity; Nat Rev Immunol; 9(6); pp. 418-428; Jun. 2009.
Tracey, K.J., The inflammatory reflex, Nature, vol. 420, pp. 853-859, Dec. 19-26, 2002.
Tsutsui, H., et al., Pathophysiolocical roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Der Horst et al.; Stressing the role of FoxO proteins in lifespan and disease; Nat Rev Mol Cell Biol.; vol. 8; No. 6; pp. 440-450; Jun. 2007.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Vanhoutte, et al., Muscarinic and beta-adrenergic prejunctional modulation of adrenergic neurotransmission in the blood vessel wall, Gen Pharmac., vol. 14(1), pp. 35-37, Jan. 1983.

(56) References Cited

OTHER PUBLICATIONS vanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16(2), pp. 101-102, Feb. 2000.
Vida et al.; Aplha 7-cholinergic receptor mediates vagal induction of splenic norepinephrine; Journal of Immunology; 186(7); pp. 4340-4346; 16 pages; (Author Manuscript); Apr. 2011.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.
Walland et al., Compensation of muscarinic brochial effects of talsaclidine by concomitant sympathetic activation in guinea pigs; European Journal of Pharmacology, vol. 330(2-3), pp. 213-219, Jul. 9, 1997.
Wang et al.; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF-? dysregulation in asthma: relationship to ongoing corticosteroid therapy, Can. Respir. J., vol. 7, No. 3, pp. 229-237, May-Jun. 2000.
Watanabe, H. et al., The significance of tumor necrosis factor (TNF) levels for rejection of joint allograft, J. Reconstr. Microsurg., vol. 13, No. 3, pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary, definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.
Westerheide et al.; Stress-inducible regulation of heat shock factor 1 by the deacetylase SIRT1.; Science; Vo. 323; No. 5717; pp. 1063-1066; Feb.-2009.
Whaley, K. et al., C2 synthesis by human monocytes is modulated by a nicotinic cholinergic receptor, Nature, vol. 293, pp. 580-582, Oct. 15, 1981.

Woiciechowsky, C. et al., Sympathetic activation triggers systemic interleukin-10 release in immunodepression induced by brain injury, Nature Med., vol. 4, No. 7, pp. 808-813, Jul. 1998.
Yang et al.; Acetylcholine inhibits LPS-induced MMP-9 production and ccell migration via the alpha7 nAChR-JAK2/STAT3 pathway in RAW264.7 cells; Cellular Physiology and Biochemistry; 36(5); pp. 2025-2038; (the year of publication is sufficiently earlier than the effective U.S. filing date and any foreign priority date so that the particilar month of publication is not in issue) 2015.
Yang et al.; Axon myelination and electrical stimulation in a microfluidic, compartmentalized cell culture platform; Neuromolecular medicine; vol. 14; pp. 112-118; Jun. 2012.
Yeh, S.S. et al., Geriatric cachexia: the role of cytokines, Am. J. Clin. Nutr., vol. 70(2), pp. 183-197, Aug. 1999.
Yu et al.; Low-level transcutaneous electrical stimulation of the auricular branch of the vagus nerve: a non-invasive approach to treat the initial phase of atrial fibrillation, Heart Rhythm; pp. 428-435; Mar. 2013.
Zamotrinsky et al.; Vagal neurostimulation in patients with coronary artery disease; Auton. Neurosci.; 88(1-2); pp. 109-116; Apr. 2001.
Zhang et al., Tumor necrosis factor, The Cytokine Handbook, 3rd ed., Ed. Thompson, Academic Press, pp. 517-548, Jul. 1, 1998.
Zhang et al.; Chronic vagus nerve stimulation improves autonomic control and attenuates systemic inflammation and heart failure progression in a canine high-rate pacing model; Circulation Heart Fall., 2; pp. 692-699; Nov. 2009.
Zhang et al.; Roles of SIRT1 in the acute and restorative phases following induction of inflammation.; J Biol Chem.; vol. 285; No. 53; pp. 41391-401; Dec.-2010.
Zhao et al.; Transcutaneous auricular vagus stimulation protects endotoxemic rat from lipopolysaccharide-induced inflammation; Evid. Based Complement Alternat. Med.; vol. 2012; Article ID 627023; 10 pages; Dec. 29, 2012.
Zitnik et al.; Treatment of chronic inflammatory diseases with implantable medical devices; Cleveland Clinic Journal of Medicine; 78(Suppl 1); pp. S30-S34; Aug. 2011.
Calle et al.; U.S. Appl. No. 18/562,283 entitled "Neurostimulation parameter authentication and expiration system for nuerostimulation," filed Nov. 17, 2023.
Levine et al.; U.S. Appl. No. 18/431,974 entitled "Vagus nerve stimulation pre-screening test," filed Feb. 3, 2024.
Levine; U.S. Appl. No. 18/605,809 entitled "Bimodal vagus nerve simulation to treat neurodegenerative disorders," filed Mar. 14, 2024.
Hebb et al.; Creating the Feedback Loop: Closed-Loop Neurostimulation; Neurosurgery Clinics of North America; 25(1); pp. 187-204; Jan. 28, 2014.
Li et al.; U.S. Appl. No. 18/645,129 entitled "System and methods of stimulation at trigeminaly innervated regions for disorders of cerebral perfusion," filed Apr. 24, 2024.
Levine et al.; U.S. Appl. No. 18/730,753 entitled "Treatment of inflammatory disorders," filed Jul. 19, 2024.
Huston et al.; U.S. Appl. No. 18/829,209 entitled "Methods and apparatuses for reducing bleeding via electrical trigeminal nerve stimulation," filed Sep. 9, 2024.
McLean et al.; Delayed nerve stimulation promotes axon-protective neurofilament phosphorylation, accelerates immune cell clearance and enhances remyelination in vivo in focally demyelinated nerves; PloS one; 9(10); e110174; 17 pages; Oct. 13, 2014.

\* cited by examiner

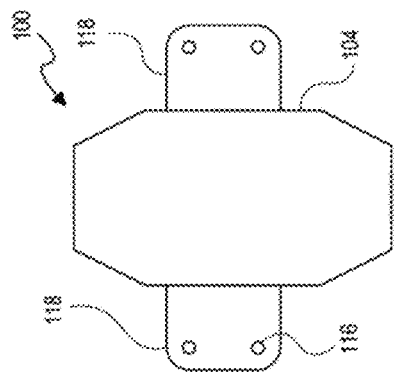
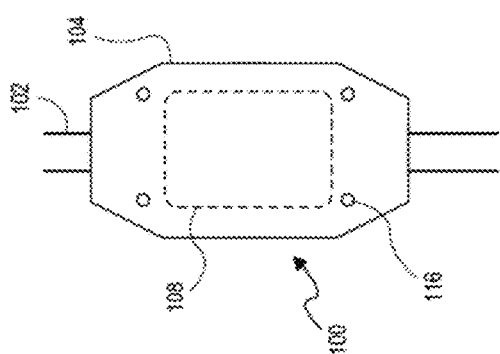
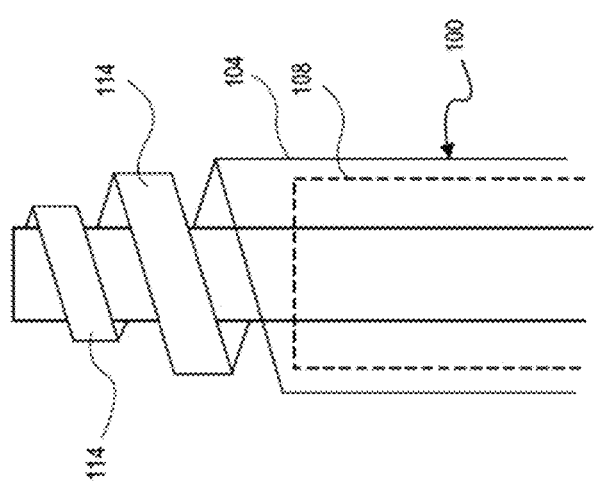
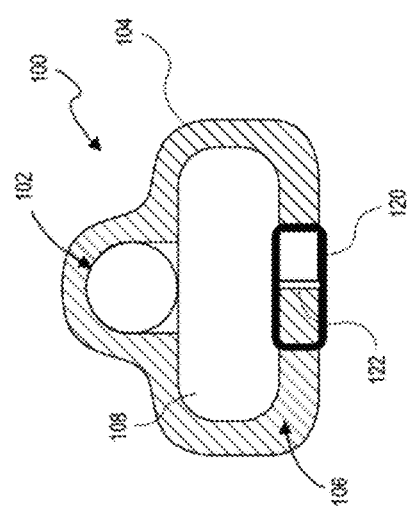

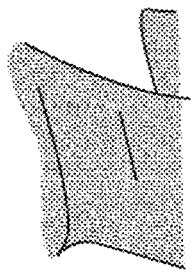
1. Cervical Incision on Lange's Crease
FIG. 22A
2. Cut Down
FIG. 22B
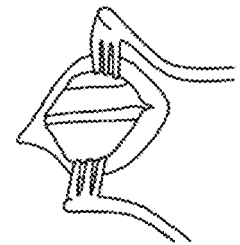
3. Expose Nerve
FIG. 22C
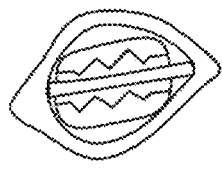
4. Place Pod under nerve
FIG. 22D
5. Place stimulator in POD
FIG. 22E
6. Suture POD Closed
FIG. 22F
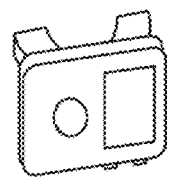
7. Use Surgical Tester to verify operation
FIG. 22G
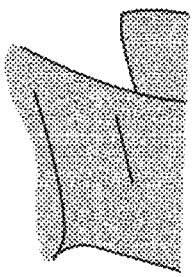
8. Close Cervical Incision
FIG. 22H

FIG. 24D
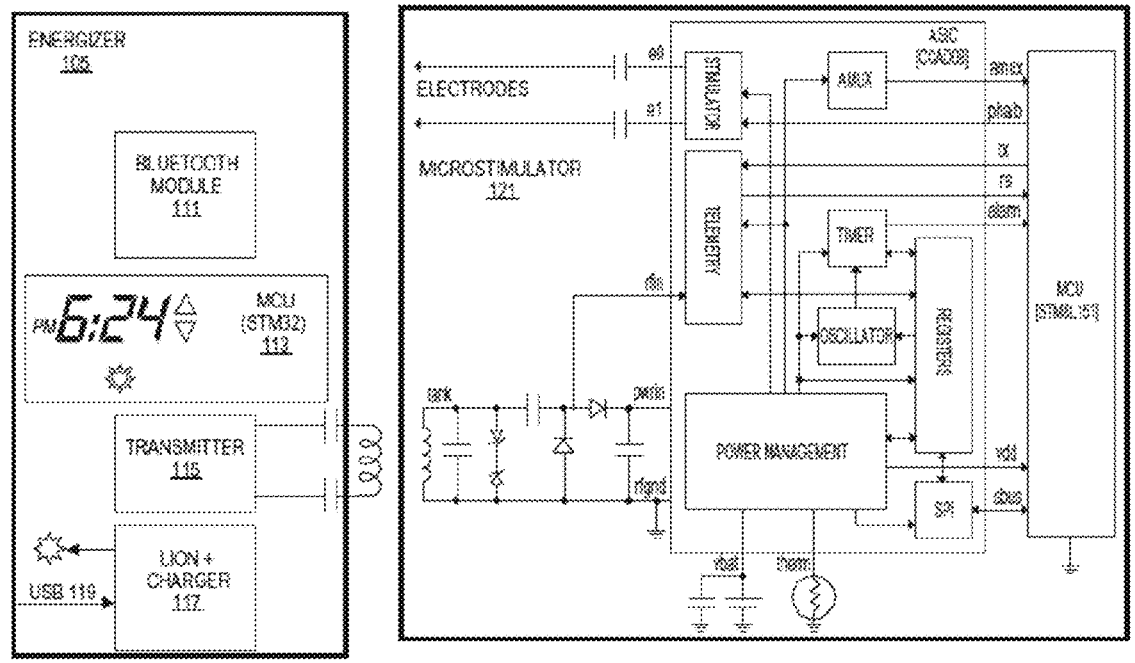
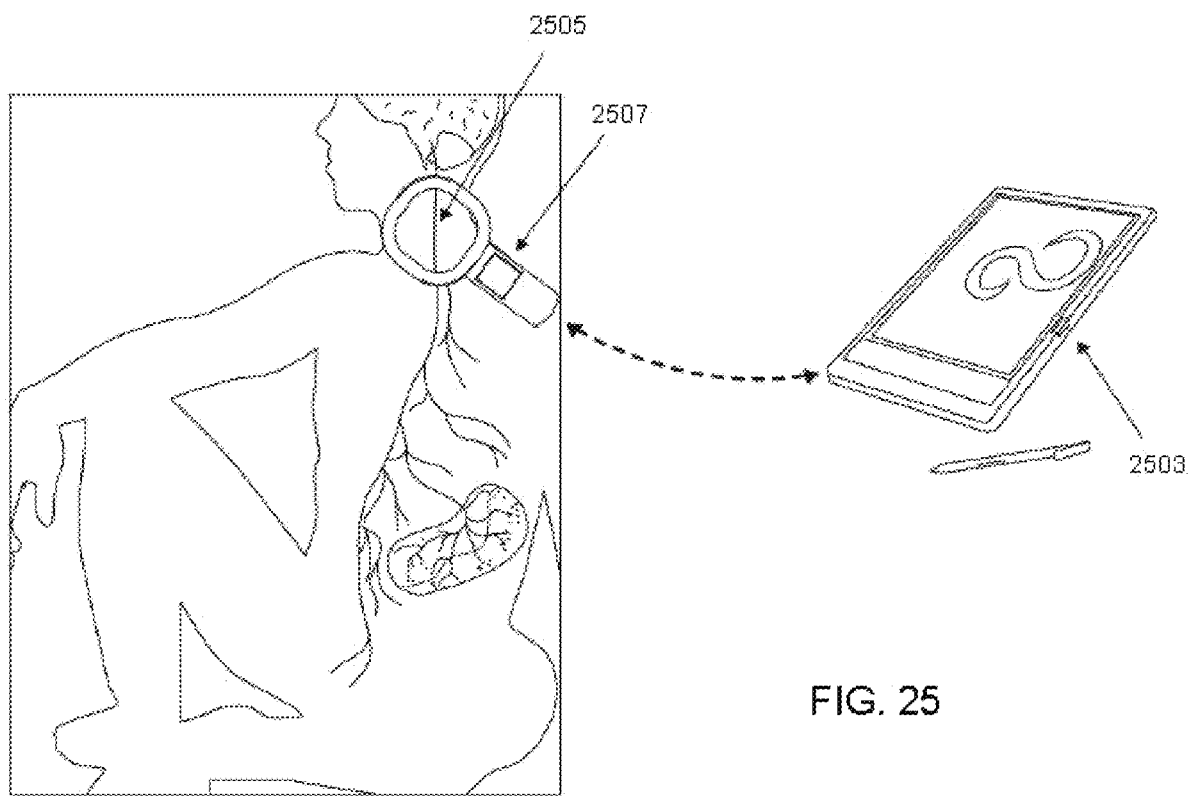
FIG. 25

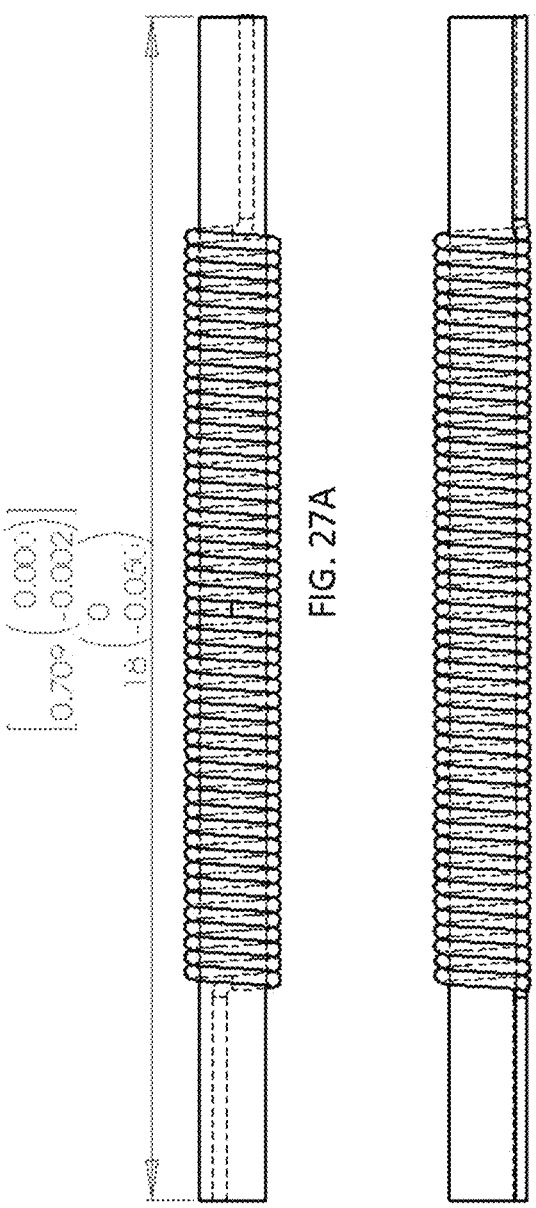
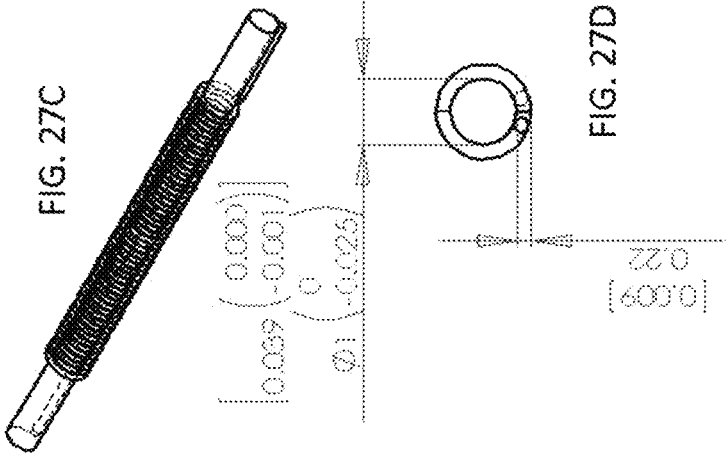
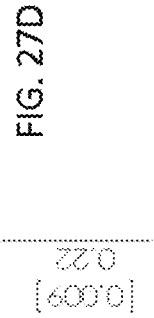
FIG. 27C
FIG. 27D
FIG. 27A
FIG. 27B
Specifications:
Coil Inductance = 20.4 μH +/-5%
MnZn Ferrite Core (77 or 78 material)
Ferrite Permeability = μ ≥ 2000
Maximum Operating Frequency = 131 kHz
Total Diameter of wire ≤ 0.009"
51 Turns
Suggested Insulated wire:
MWS 32 AWG SPN155 (NEMA MW80C)
Suggested Bondable Insulated wire:
MWS 33 AWG SPNB105 (NEMA MW29C)

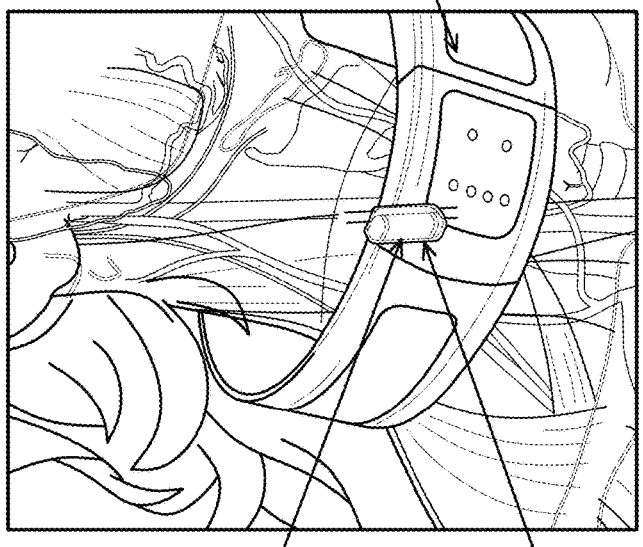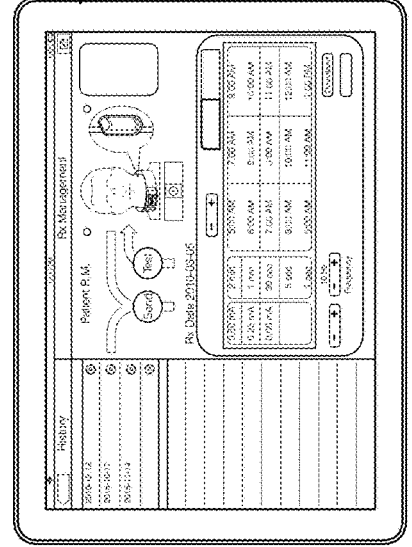
FIG. 38

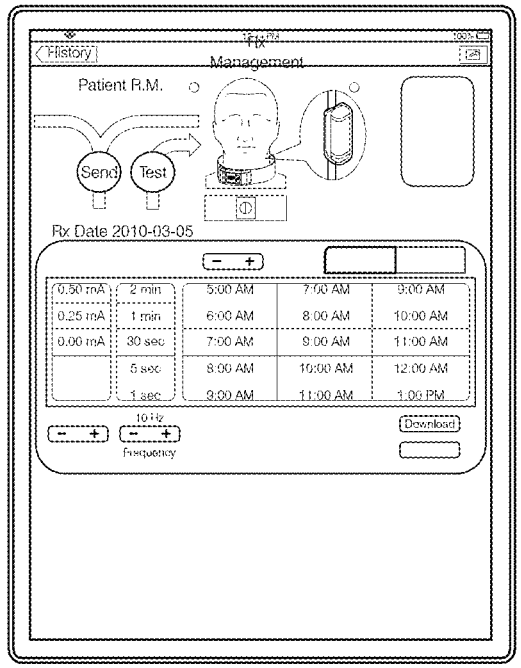
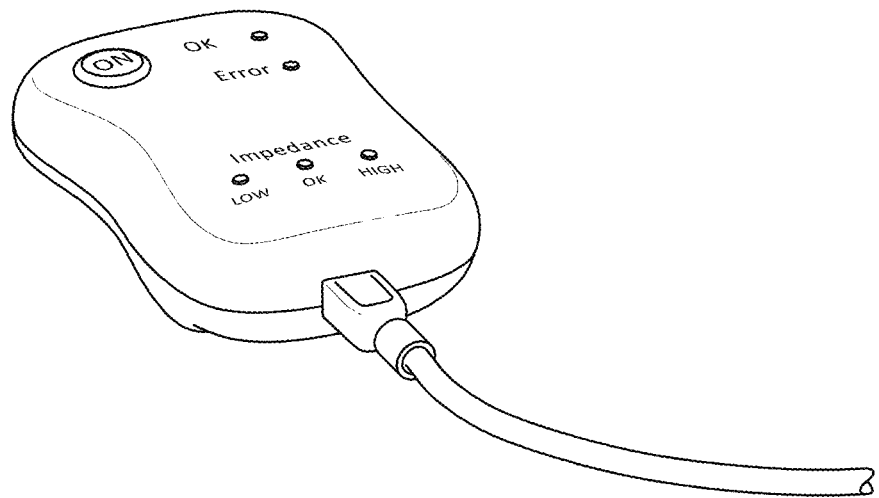
FIG. 42

≤ 20 mm

FLEXIBLE NECK CAN BE BENT TO ALLOW MOST CONVENIENT ACCESS TO IMPLANT; WILL HOLD ITS SHAPE

HEAD STYLE
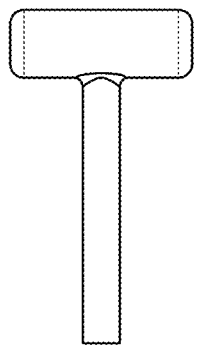
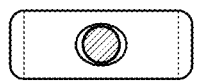
FIG. 46A
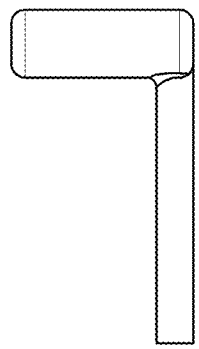
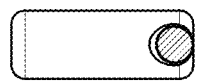
FIG. 46B
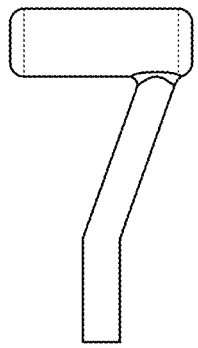
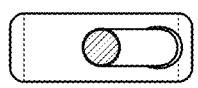
FIG. 46C
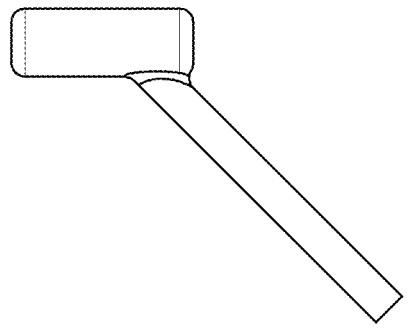
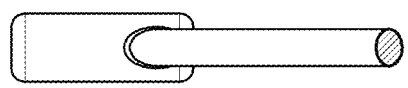
FIG. 46D

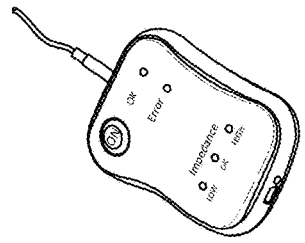
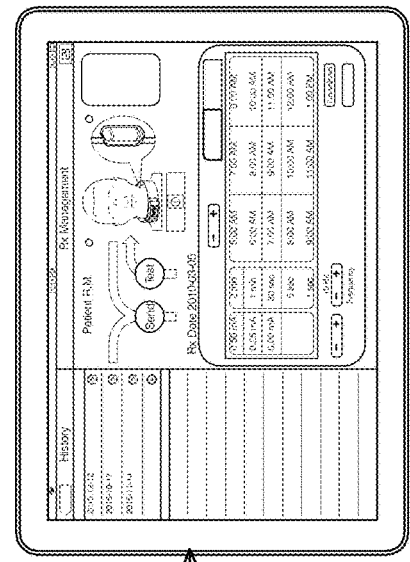
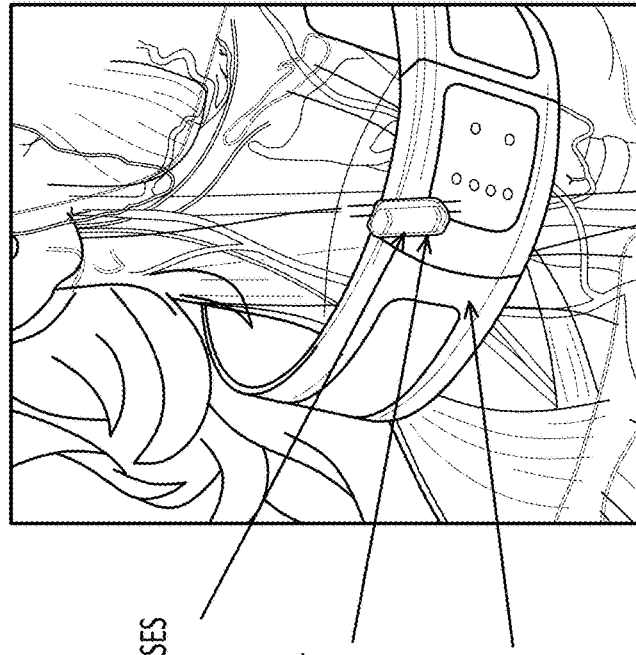

TEST PROBE
- STERILE INSITU TESTING

SURGICAL TESTER
- PRECONDITIONS MR
- INSITU TESTING

COMPLETE MICROREGULATOR SYSTEM

MICROREGULATOR (MR)
- DELIVERS STIMULUS DOSES
- RECHARGABLE BATTERY

POD
- POSITIONS MR AGAINST VAGUS
- SHIELDS AND DIRECTS CURRENT

ENERGIZER/CHARGER
- CHARGES MR (DAILY/WEEKLY)
- ENABLES MANUAL DOSING
- COMMUNICATION LINK BETWEEN MR & RxPAD

RxPad
- UTILIZES APPLE iPad
- PROGRAMS MR

FIG. 47

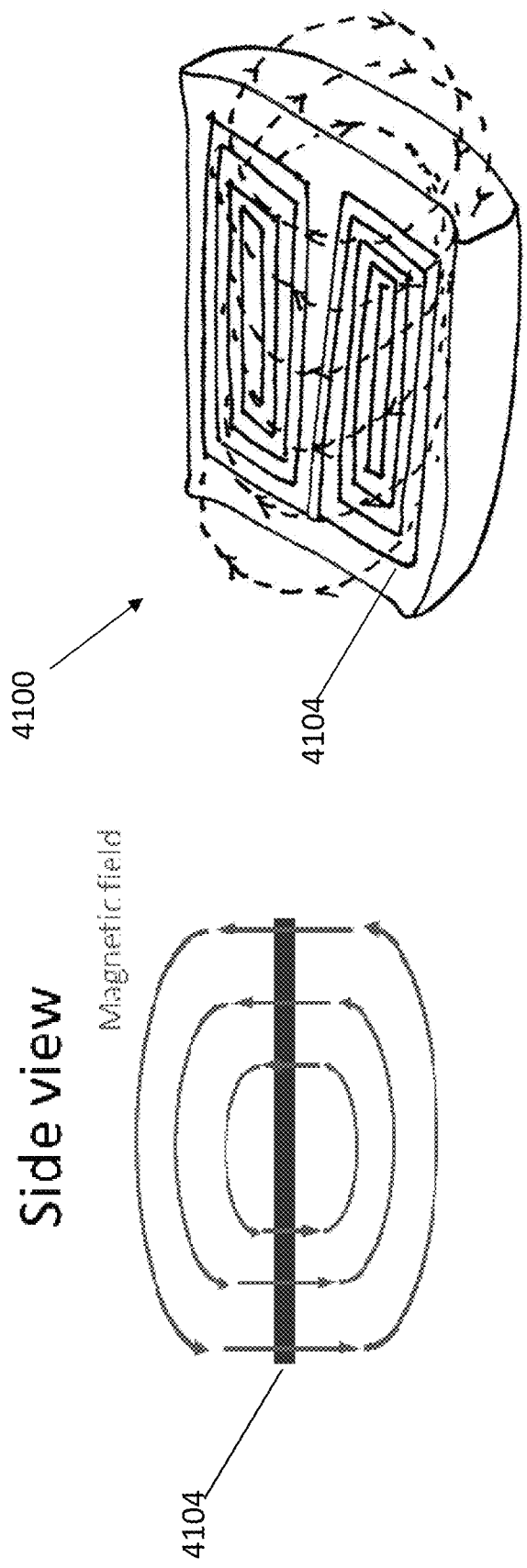

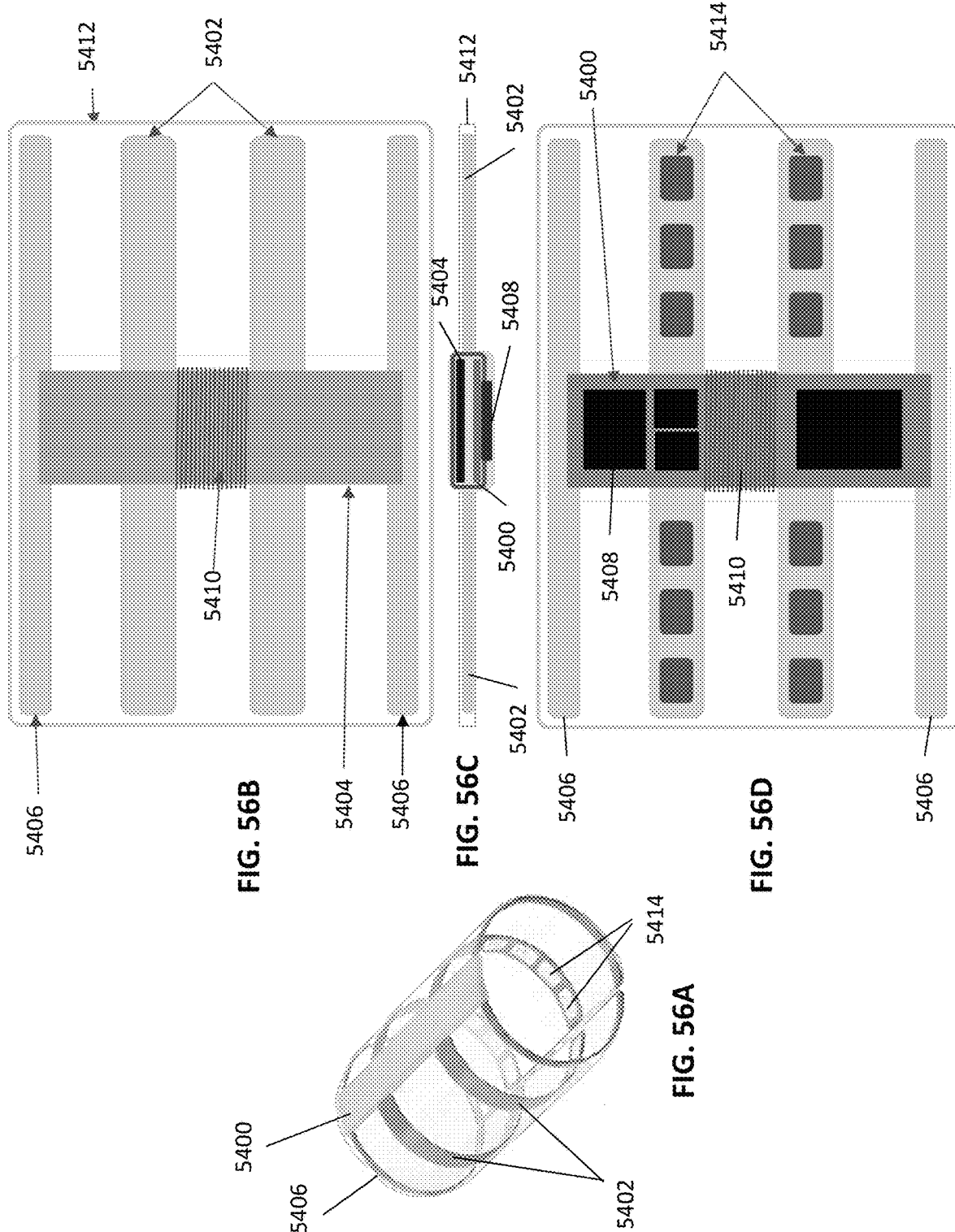

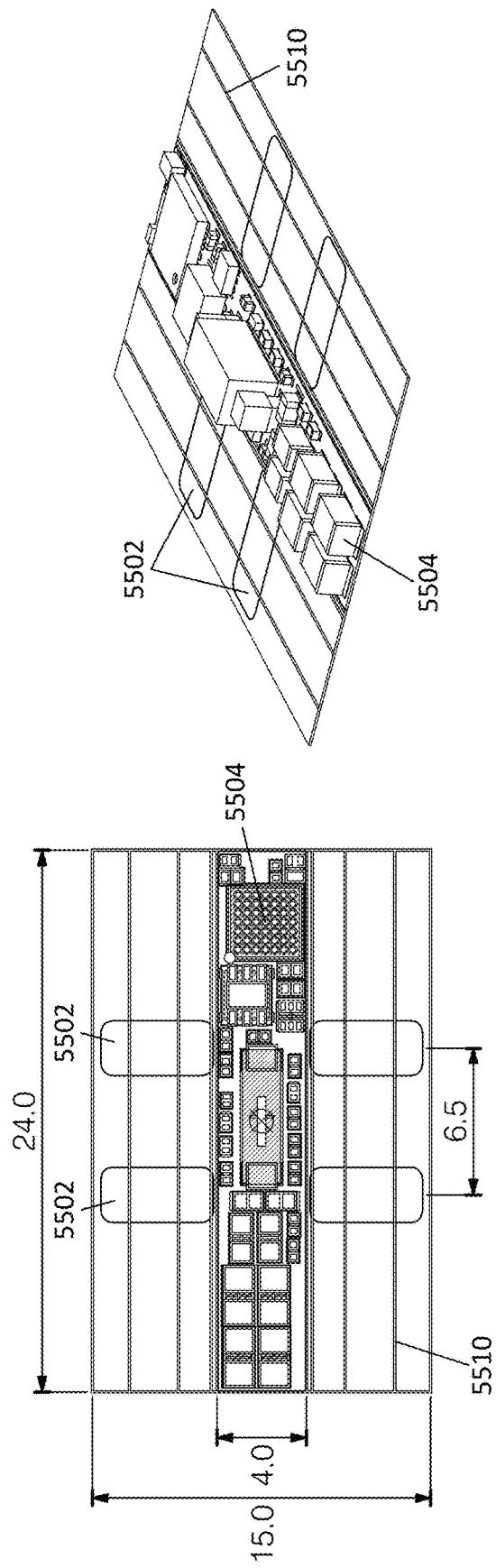
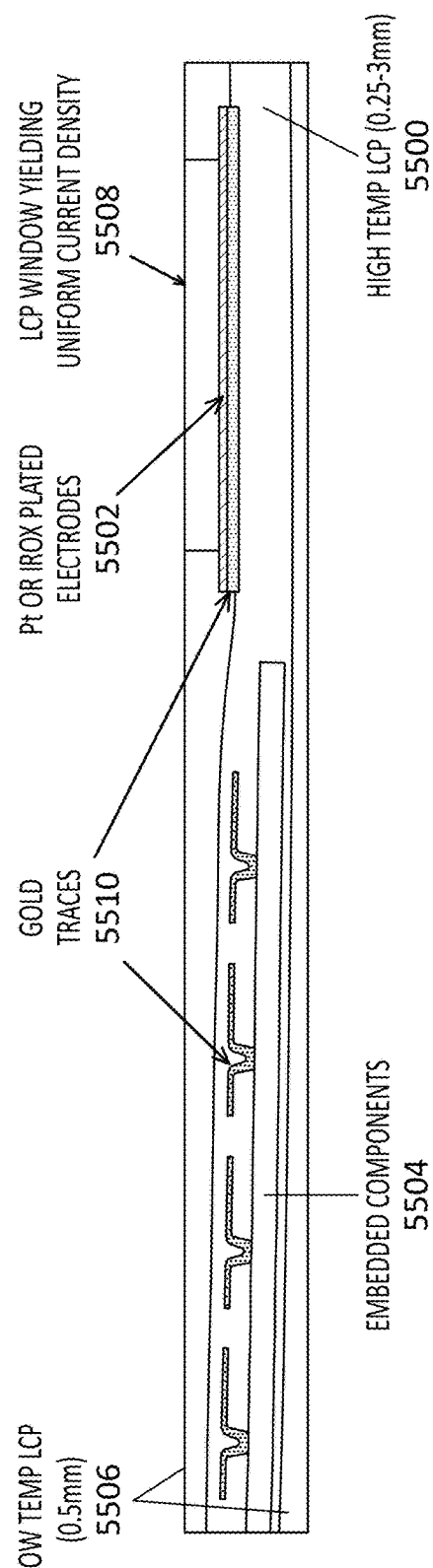
FIG. 57B
FIG. 57A
FIG. 57C

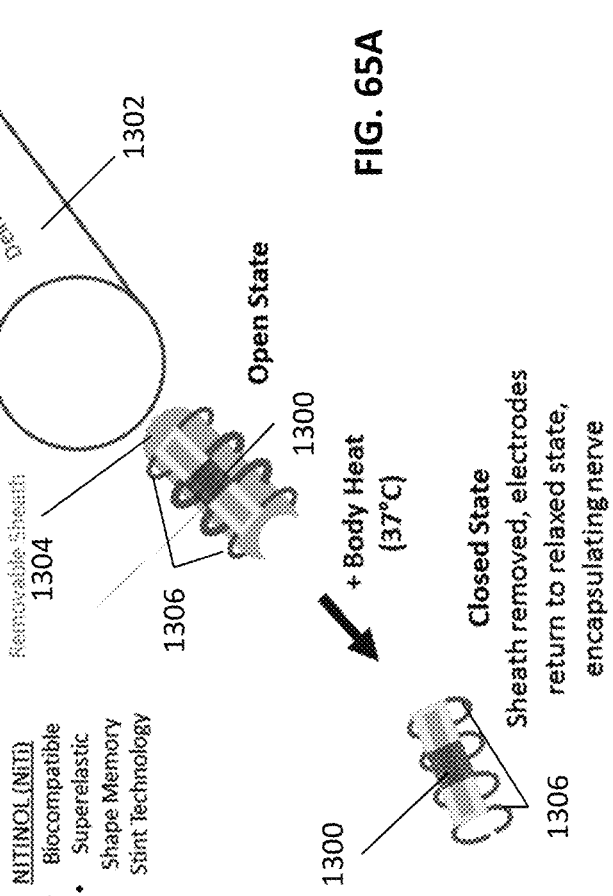
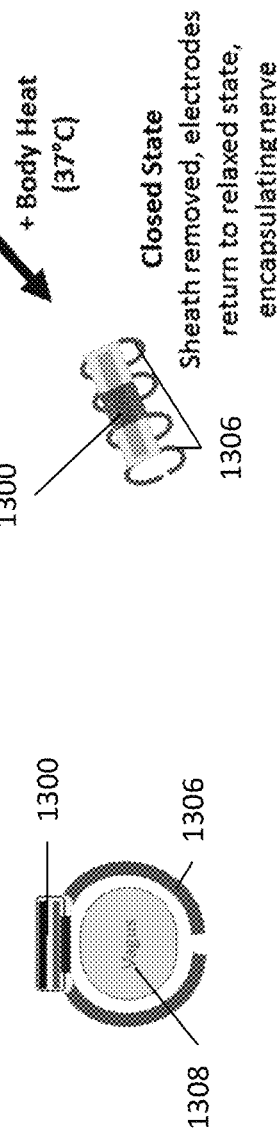
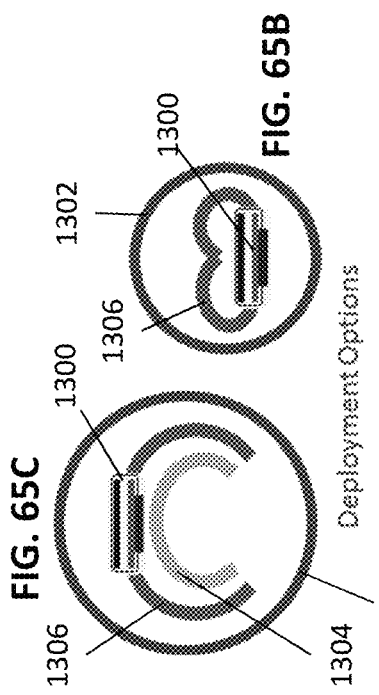
FIG. 65A
FIG. 65B
FIG. 65C
FIG. 65D

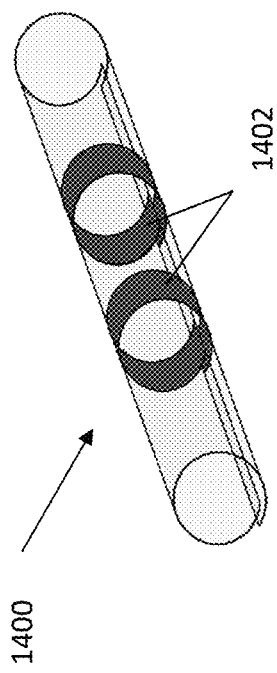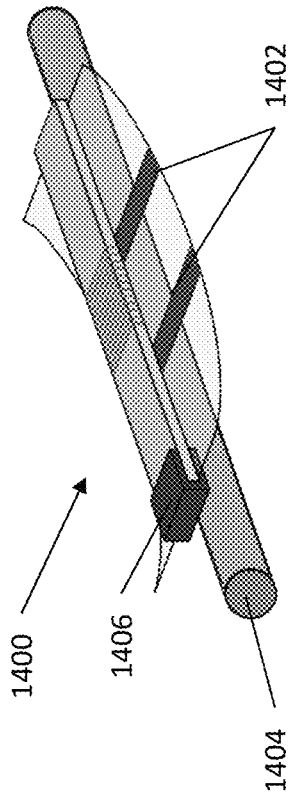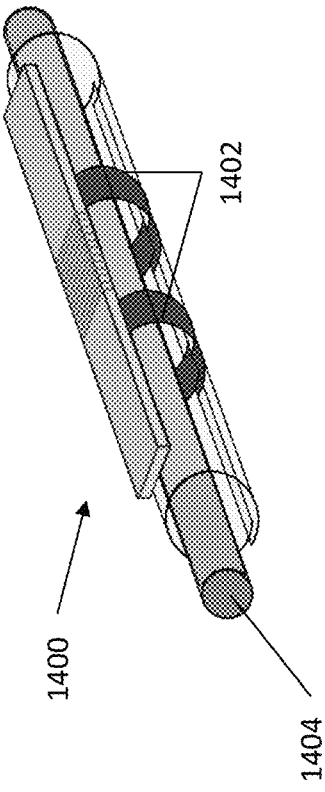

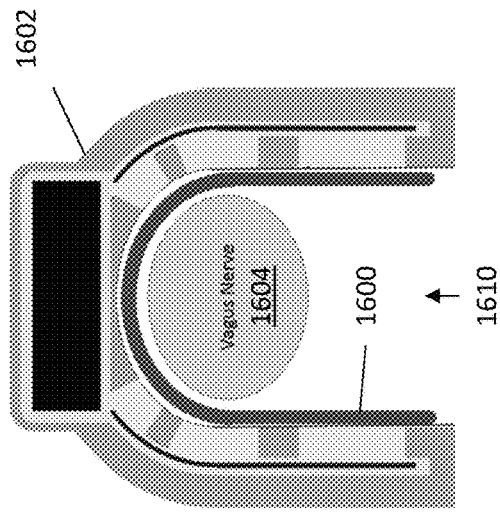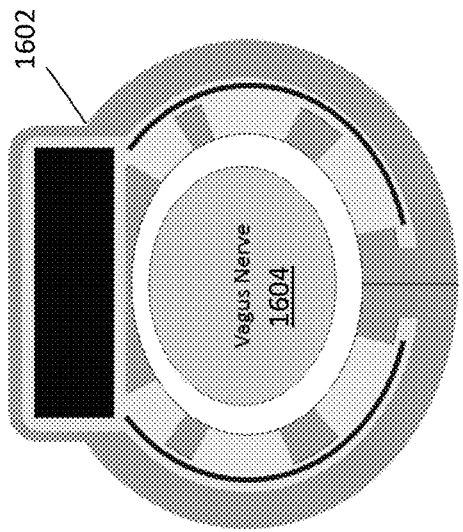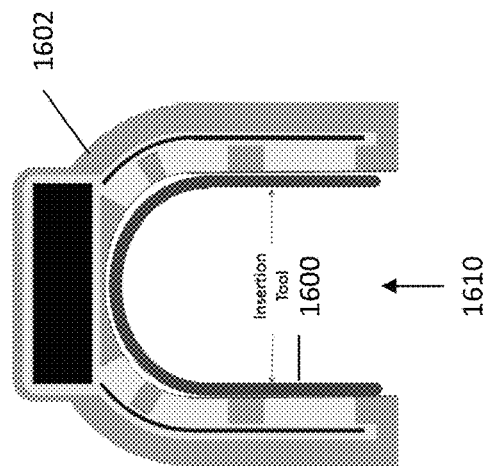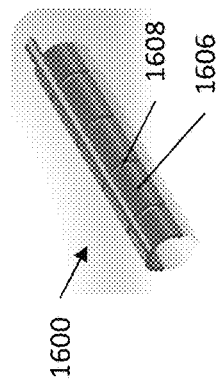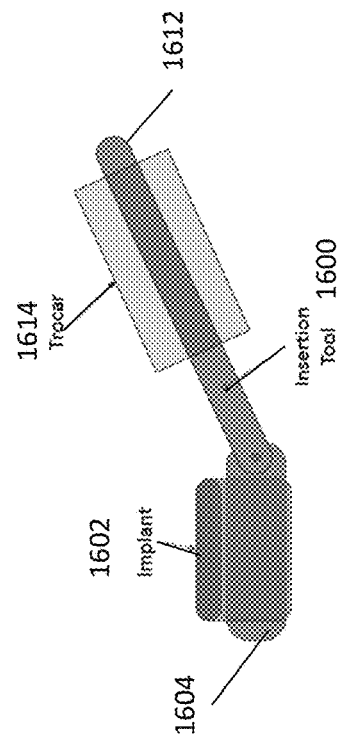
FIG. 68A
FIG. 68B
FIG. 68C
FIG. 68D
FIG. 68E

BATTERYLESS IMPLANTABLE MICROSTIMULATORS

CROSS REFERENCE TO RELATED APPLICATION

This patent application is a continuation of U.S. patent application Ser. No. 17/875,327, titled "BATTERYLESS IMPLANTABLE MICROSTIMULATORS," filed Jul. 27, 2022, now U.S. Patent Application Publication No. 2022/0362555, which is a continuation of U.S. patent application Ser. No. 16/356,906, titled "BATTERYLESS IMPLANTABLE MICROSTIMULATORS," filed Mar. 18, 2019, now U.S. Pat. No. 11,471,681, which claims priority as a continuation-in-part to U.S. patent application Ser. No. 15/411,936, titled "IMPLANTABLE MICROSTIMULATORS AND INDUCTIVE CHARGING SYSTEMS," filed on Jan. 20, 2017, now U.S. Pat. No. 10,314,501, which claims priority to U.S. Provisional Patent Application No. 62/281,029, titled "SUB-DIAPHRAGMATIC STIMULATION OF THE CHOLINERGIC ANTI-INFLAMMATORY PATHWAY," filed on Jan. 20, 2016; U.S. Provisional Patent Application No. 62/286,940, titled "PILLOW CHARGER FOR IMPLANTABLE NEURAL STIMULATION DEVICES," filed on Jan. 25, 2016; U.S. Provisional Patent Application No. 62/286,943, titled "NEURAL STIMULATION DEVICES AND SYSTEMS," filed on Jan. 25, 2016; and U.S. Provisional Patent Application No. 62/286,945, titled "INDUCTIVE CHARGERS FOR NEURAL STIMULATION DEVICES," filed on Jan. 25, 2016. Each of these patent applications is herein incorporated by reference in its entirety.

This application may also be related to one or more of: U.S. patent application Ser. No. 14/887,192, titled "NEURAL STIMULATION DEVICES AND SYSTEMS FOR TREATMENT OF CHRONIC INFLAMMATION", filed on Oct. 19, 2015, Publication No. US-2016-0038745-A1 and Patent Cooperation Treaty (PCT) Application No. PCT/US2016/032169, titled "EXTERNAL PROGRAMMER", filed on May 12, 2016, Publication No. WO2016/183353. Each of these patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Embodiments of the invention relate generally to apparatuses (e.g., systems and devices) and methods of establishing neuronal stimulation. In particular, described herein are implantable microstimulation (MS) devices for treatment of chronic inflammation adapted for electrically stimulating one or more nerves (e.g., the vagus nerve) to treat chronic inflammation by modulation of the inflammatory response via the nicotinic cholinergic anti-inflammatory ("NCAP") pathway. These apparatuses may batteryless. Any of the methods and apparatuses described herein may be in particular adapted for stimulation of the vagus nerve below the diaphragm (e.g., sub-diaphragmatic vagus nerve stimulation).

BACKGROUND

Electrical stimulation of the cholinergic anti-inflammatory pathway (NCAP) by stimulation of the carotid vagus nerve been well described. For example, see U.S. Pat. Nos. 6,838,471, 8,914,114, 9,211,409, 6,610,713, 8,412,338, 8,996,116, 8,612,002, 9,162,064, 8,855,767, 8,886,339, 9,174,041, 8,788,034 and 9,211,410, each of which is herein incorporated by reference in its entirety.

Implantable electrical stimulation devices have been developed for therapeutic treatment of a wide variety of diseases and disorders. For example, implantable cardioverter defibrillators (ICDs) have been used in the treatment of various cardiac conditions. Spinal cord stimulators (SCS), or dorsal column stimulators (DCS), have been used in the treatment of chronic pain disorders including failed back syndrome, complex regional pain syndrome, and peripheral neuropathy. Peripheral nerve stimulation (PNS) systems have been used in the treatment of chronic pain syndromes and other diseases and disorders. Functional electrical stimulation (FES) systems have been used to restore some functionality to otherwise paralyzed extremities in spinal cord injury patients.

Typical implantable electrical stimulation systems may include one or more programmable electrodes on a lead that are connected to an implantable pulse generator (IPG) that contains a power source and stimulation circuitry. However, these systems can be difficult and/or time consuming to implant, as the electrodes and the IPG are usually implanted in separate areas and therefore the lead must be tunneled through body tissue to connect the IPG to the electrodes. Also, leads are susceptible to mechanical damage over time, particularly as they are usually thin and long.

Recently, small implantable neural stimulator technology, i.e. microstimulators, having integral electrodes attached to the body of a stimulator has been developed to address the disadvantages described above. This technology allows the typical IPG, lead and electrodes described above to be replaced with a single integral device. Integration of the lead has several advantages including reduction of surgery time by eliminating, for example, the need for implanting the electrodes and IPG in separate places, the need for a device pocket, the need for tunneling to the electrode site, and requirements for strain relief ties on the lead itself. Reliability may therefore be increased significantly, especially in soft tissue and across joints because active components, such as lead wires, are now part of the rigid structure and are not subject to the mechanical damage due to repeated bending or flexing over time.

There remains a need for a leadless integral device that is stably positioned on the nerve, and can provide for removal and/or replacement of the stimulation device with relative ease.

Charging and/or communication with an implant by electrical induction (e.g., via one or more inductive coils) may be well suited for use with implantable microstimulators, including those adapted for use to treat inflammation. However, induction may be difficult, particularly where the implant is located deep within the body, as may be the case with a sub-diaphragmatic implant, or where the orientation is not known or is difficult to align with. In previous iterations of the recharging portion of the system, the recharger included a coil that could be worn around a patient's neck. In this configuration, the coil is able to generate an electromagnetic field having sufficient strength to penetrate the patient's body and reach the implanted device for recharging the implanted device. While this recharging scheme is effective, it requires the patient to periodically wear a ring around their necks.

Described herein are microstimulators, charging systems, and methods of using them that may address some of the needs identified above.

Although stimulation of the vagus nerve at the upper levels has been well characterized, stimulation of the NCAP pathway at more distal sites, including sub-diaphragmatic sites has not been well characterized, and poses unique problems and opportunities.

For example, stimulation of sub-diaphragmatic sites may provide fewer adverse events and particularly possibly providing fewer undesirable cardiac effects and laryngeal effects. However, sub-diaphragmatic placement has not been characterized, and may be expected to have a lower efficacy. In addition, the NCAP pathways in sub-diaphragmatic regions may be difficult to access and provide stable placement of a microstimulator.

Also described herein are methods an apparatuses that may address the issues raised above.

SUMMARY OF THE DISCLOSURE

The present invention relates generally to apparatuses (systems and devices) and methods for treating an inflammatory disease stimulation the NCAP. Any of the methods and apparatuses described herein may be configured for sub-diaphragmatic stimulation. Also described herein are methods of implanting a stimulation apparatus (including sub-diaphragmatic implantation of a stimulation apparatus) for NCAP stimulation, apparatuses for stimulation (including sub-diaphragmatic stimulation apparatuses for sub-diaphragmatic NCAP stimulation), and methods and apparatuses for noninvasively charging a stimulation apparatus, including but not limited to apparatuses and methods for sub-diaphragmatic NCAP stimulation.

Described herein are microstimulators (MSs, also referred to herein as microregulators or MRs) that may be implanted for stimulating a nerve, such as the vagus nerve. Any of these apparatuses may include a coil for receiving (and in some variations transmitting) information and/or for inductively charging the implanted device. The coil may be referred to as an antenna or inductive coil, or inductive coil antenna. In some variations the coil may be wrapped around a housing and/or a core which may be completely or partially ferromagnetic, which may modify (e.g., concentrate, direct) the magnetic field for effective charging and/or communication with a remote charger.

For example, a microstimulator may include: a housing made of a high magnetic permeability material; a coil wrapped around the housing, wherein the housing functions as a magnetic core for the coil; a resonator comprising the coil and a capacitor configured to resonate at a predetermined frequency range; a pair of electrodes disposed on the housing; a battery within the housing; and an electronic assembly within the housing, wherein the electronic assembly comprises power management circuitry configured to receive power from the resonator to charge the battery, and a microcontroller configured to control stimulation of the vagus nerve from the electrodes.

In general, a material having a high magnetic field permeability may include certain iron alloys (ferrites), ferrite-filled polymer, ferrite-embedded polymer, alloys of iron and nickel (e.g., commercially sold as MUMETAL and PERMALLOY) and the like. The high magnetic permeability material may be selected from the group consisting of a ferrite and a Mu-metal.

In any of these variations, the high magnetic permeability material may include one or more slits configured to reduce formation of eddy currents in the high magnetic permeability material.

In any of the variations described herein, the resonator (including the coil and a capacitor) may be configured to resonate at a predetermined frequency range, as described in greater detail herein.

A microstimulator may include: a housing; a pair of electrodes disposed on the housing; a battery within the housing; an electronic assembly disposed on a printed circuit board within the housing; a high magnetic permeability core integrated with the printed circuit board; a coil wrapped around the printed circuit board; and a resonator within the housing, the resonator comprising the coil and a capacitor configured to resonate at a predetermined frequency range; wherein the electronic assembly comprises power management circuitry configured to receive power from the resonator to charge the battery, and a microcontroller configured to control stimulation of the vagus nerve from the electrodes.

In some variations, the high magnetic permeability core may be a rod or a plate.

Any of the microstimulators described herein may include a pair of end caps attached to a first end and a second end of the housing. The end caps may be made of a high magnetic permeability material and the high magnetic permeability core may extend to at least one of the end caps.

A microstimulator may include: a housing; a pair of electrodes disposed on the housing; a battery within the housing, the battery coated (and in some variations covered) with a high magnetic permeability material; a coil wrapped around the battery; a resonator within the housing, the resonator comprising the coil and a capacitor configured to resonate at a predetermined frequency range; and an electronic assembly within the housing; wherein the electronic assembly comprises power management circuitry configured to receive power from the resonator to charge the battery, and a microcontroller configured to control stimulation of the vagus nerve from the electrodes.

A microstimulator may include: a magnetic core having a first end and a second end; a coil wrapped around the magnetic core; a housing, wherein the magnetic core and coil are disposed outside of the housing; a pair of electrodes disposed on the housing; a battery within the housing; a resonator comprising the coil and a capacitor configured to resonate at a predetermined frequency range; and an electronic assembly within the housing; wherein the electronic assembly comprises power management circuitry configured to receive power from the resonator to charge the battery, and a microcontroller configured to control stimulation of the vagus nerve from the electrodes. The first end of the magnetic core may be attached to the housing.

The magnetic core may be configured to be remotely placed away from the housing while remaining in electrical communication with the electronic assembly.

Any of the microstimulators described herein may be adapted for application to a vagus nerve.

The apparatuses (devices and systems) and methods of using them described herein may incorporate some or all of the features of microstimulators (which may also be referred to as microcontrollers), nerve cuffs ("PODs"), chargers, and programmer/controllers described herein may be similar or identical to those described in U.S. patent application Ser. No. 12/874,171, titled "PRESCRIPTION PAD FOR TREATMENT OF INFLAMMATORY DISORDERS", filed on Sep. 1, 2010, Publication No. US-2011-0054569-A1 and U.S. patent application Ser. No. 12/797,452, titled "NERVE CUFF WITH POCKET FOR LEADLESS STIMULATOR", filed on Jun. 9, 2010, now U.S. Pat. No. 8,886,339 and U.S. patent application Ser. No. 14/887,192, titled "NEURAL STIMULATION DEVICES AND SYSTEMS FOR TREATMENT OF CHRONIC INFLAMMATION", filed on Oct. 19, 2015, Publication No. US-2016-0038745-A1.

The apparatuses (devices and systems) described herein may include chargers that are adapted to direct the magnetic field for communication with an implanted microstimulator. These chargers may include a high magnetic permeability material that shapes the magnetic field. In particular, the charger may be configured as a collar or wearable loop (belt, wristlet, anklet, necklace, etc.) that includes a magnetically permeable material to displace the density of the magnetic field axially "up" or "down" relative to the loop.

For example, a charger for inductively charging a neurostimulator implanted within a portion of the patient's body may include: a coil configured to be disposed around the portion of the patient's body with the implanted neurostimulator; a covering having a tubular shaped disposed over the coil, wherein the covering comprises a high magnetic permeability material that is arranged on an inner surface of the tubular shape but is not on an outer surface; an amplifier configured to drive an electrical current through the coil to generate an electromagnetic field; and a controller configured to modulate the electrical current driven through the coil.

For example, a charger for charging a neurostimulator implanted within a portion of the patient's body may include: a coil configured to be disposed around the portion of the patient's body with the implanted neurostimulator; a covering disposed over the coil, wherein the covering is made at least in part of a high magnetic permeability material, wherein the high magnetic permeability material has a magnetic permeability greater than 10 times the magnetic permeability of vacuum; an amplifier configured to drive an electrical current through the coil to generate an electromagnetic field; and a controller configured to modulate the electrical current driven through the coil.

In general, the high magnetic permeability material may be selected from the group consisting of a ferrite, a ferrite polymer composite, a ferrite filled polymer, a ferrite loaded rubber, and a ferrite tape.

The high magnetic permeability material (HMPM) may be disposed asymmetrically over the coil in order to concentrate and bias the electromagnetic field passing through the coil towards the implanted neurostimulator. For example, the HMPM may form a U-shape over the coil with the mouth of the U-shape (opening) directed axially "up" to direct the field in this direction. The high magnetic permeability material may be disposed on a skin facing side of the covering that is configured to face the patient's skin when the coil is disposed around the portion of the patient's body with the implanted neurostimulator. The high magnetic permeability material may be disposed on a portion of the covering that is configured to face implant when the coil is disposed around the portion of the patient's body with the implanted neurostimulator.

In any of the variations described herein, a high magnetic permeability material may include at least one slit that is configured to reduce formation of eddy currents in the high magnetic permeability material.

Also described herein are testers and chargers. For example, a handheld charger for charging a neurostimulator implanted within a portion of the patient's body may include: a C-shaped ferrite having a first end, a second end, and a gap between the first end and the second end, wherein the gap is adapted to be placed against the patient's skin; a coil wrapped around the ferrite; an amplifier configured to drive an electrical current through the coil to generate an electromagnetic field that extends through the ferrite and the gap; and a controller configured to modulate the electrical current driven through the coil.

Also described herein are methods of charging a microcontroller/microregulator (e.g., neurostimulator) implant as described herein. For example, a method for charging a neurostimulator implanted in a patient's neck may include: positioning a coil of a charger around the patient's neck, the charger having a covering over the coil comprising a high magnetic permeability material disposed on a portion of the covering; positioning the high magnetic permeability material to face towards the implant; passing a current through the coil; and generating an electromagnetic field that is concentrated towards the implanted neurostimulator.

Also described herein are wireless charging or recharging of an implantable neurostimulation device. The implantable neurostimulation device has been implanted about a patient's vagus nerve and is able to provide stimulation to the vagus nerve in a periodic fashion. The components for transferring energy to the implanted neurostimulation device are embedded in a pillow. The pillow recharger allows recharging of the implanted neurostimulation device while the patient sleeps or rests.

The pillow recharger includes at least one transmitter coil that is configured to generate electromagnetic waves. The transmitter coil or coils are configured to generate electromagnetic energy that oscillates within a threshold of the desired resonant frequency such that the transmitter coil(s) are able to transfer energy to the corresponding receiver coils within the implanted neurostimulation device. The power transmitter coil or coils may be in a figure eight configuration where the coils are circular, square, rectangular, and so forth. In some examples, the coil is one contiguous stretch of conductive material, but in others, there may be more than one discrete coil. If the surface of the pillow and the transmitter coil(s) are defined as being in an x/y plane, the current will run in an opposing fashion within the transmitter coil or coils. The electromagnetic field generated by the transmitter coil or coils will generally provide current that traverses up through the x/y plane along a z axis direction and drop down toward the opposing z axis direction through the other transmitter coil.

The pillow recharger may also include a physical backing that is able to support the transmitter coil or coils. The physical backing may also function to provide shielding to the transmitter coils such that nearby metallic objections do not interfere with the electromagnetic field generated. The backing may be made from a material with a high magnetic permeability, such as ferrite, which provides shielding by providing a low-reluctance return path for the magnetic field beneath the pillow. The backing may also be made of a conductive material, which provides shielding by the induction of eddy currents in the backing.

The pillow recharger also includes a power generator that is configured to power the at least one power transmitter coil or coils. The power generator may provide an initial signal of alternating current through an initial signal generator for bringing the transmitter coil or coils into an ON state.

The pillow recharger will include circuitry and controls for monitoring and controlling the interactions between the recharging pillow and the wireless energy receiver housed within the implanted neurostimulation device. The controls that allow the user to set the recharging sessions and other recharging parameters may be partially or completely external to the recharging pillow. It is also possible that the controls may also be entirely internal to the recharging pillow and be remotely controllable.

The recharging pillow may also include sensors that alert the user if the recharging pillow is malfunctioning or is operating outside the expected range for transmitting power to the receiving mechanism within the implanted neurotransmitter device. For example, the recharging pillow may include a temperature sensor that alerts the user, through some audio signal, that the surface temperature of the pillow is above a certain value. The recharging pillow may also include pressure and force sensors that will sound if the too much pressure or force is applied to the recharging pillow that may damage the internal circuitry.

In other variations, the recharging pillow may be used to inductively recharge an implanted neurostimulator. The recharging pillow may include a first transmitter coil, where the first transmitter coil is capable of generating electromagnetic waves. The recharging pillow may also include a second transmitter coil that is also able to generate electromagnetic waves. The region defined by the first and the second transmitter coil forms a wireless power transmission region for sending power to the wireless receiver within the implanted neurostimulator. The pillow recharger also includes a power generator that is configured to deliver current through the first transmitter coil in a clockwise direction and the second transmitter coil in a counterclockwise direction causing the first transmitter coil and the second transmitter coil to generate electromagnetic energy that inductively charges the implanted neurostimulator.

The pillow recharger will also include a cushioning, support structure around the transmitter coil regions and related circuitry. The cushioning supportive materials may include any suitable material by itself or in combination. Examples of suitable materials include but are not limited to cotton, polyester, gels, foam, water, liquids, natural materials or synthetic materials, and so forth.

Also described herein are methods of treating an inflammatory disease by sub-diaphragmatic stimulation of the vagus nerve, the method comprising implanting inserting a microstimulator at least partially around a sub-diaphragmatic vagus nerve and applying electrical stimulation from the microstimulator to the sub-diaphragmatic vagus nerve to inhibit inflammation.

Implanting may include positioning a nerve cuff over a sub-diaphragmatic vagus nerve of by longitudinally introducing the nerve cuff on the sub-diaphragmatic vagus nerve. Implanting may include positioning the microstimulator within the nerve cuff in electrical contact with the sub-diaphragmatic vagus nerve. Implanting may include placing a nerve cuff around the sub-diaphragmatic vagus nerve with a microstimulator held therein and sealing the microstimulator within the nerve cuff.

Any of these methods may also include inductively charging the microstimulator from a belt worn around an abdominal region of a patient into which the microstimulator has been implanted.

For example, a method of treating an inflammatory disease by sub-diaphragmatic stimulation of the vagus nerve may include: positioning a nerve cuff over a sub-diaphragmatic vagus nerve of a patient by longitudinally introducing the nerve cuff on the sub-diaphragmatic vagus nerve; positioning a microstimulator within the nerve cuff in electrical contact with the sub-diaphragmatic vagus nerve; sealing the microstimulator within the nerve cuff; applying electrical stimulation from the microstimulator to the sub-diaphragmatic vagus nerve to inhibit inflammation; and inductively charging the microstimulator from a belt worn around an abdominal region of the patient. The pillow-charging apparatuses described herein may be particularly well suited to charging implanted microstimulators that are implanted sub-diaphragmatically. Any of the pillow-charging apparatuses may be configured as mattress or mattress-covering devices that may be positioned at or below the patient's torso level when the patient is recumbent thereon.

Also described herein are batteryless and leadless microregulators for nerve stimulation. For example, a batteryless and leadless microregulator may include: a power receiving coil configured to inductively receive a power signal; a microprocessor powered by the electrical energy received by the power receiving coil; a modulator and a demodulator in electrical communication with the power receiving coil and the microprocessor for receiving and transmitting information from the power signal; at least one pair of electrodes configured to deliver electrical stimulation using the electrical energy received by the power receiving coil; and an overmold forming a nerve channel having a slit that provides access to the nerve channel, wherein the microprocessor is configured to apply energy to the at least one pair of electrodes only when the power signal is being received by the power receiving coil, further wherein the microprocessor and electrodes are not connected to a battery.

The energy applied by device may be conditioned by the microprocessor based on the information transmitted with the inductive power signal, which may be encoded by the power signal and demodulated by the microprocessor. The microprocessor may further condition the transmitted energy by waiting until the power achieves a threshold level (and in some cases, sustains this power level at or above a threshold level for a predetermined amount of time, e.g., 0.1 second, 0.5 seconds, 1 second, 2 seconds, 5 seconds, 10 seconds, 20 seconds, 30 seconds, 1 minute, etc.) before transmitting energy.

The power receiving coil, the microprocessor, the modulator, the demodulator, and at least a portion of the at least one pair of electrodes may be encapsulated by a liquid crystal polymer, wherein the liquid crystal polymer is encapsulated by the polymer or silicon overmold. The liquid crystal polymer may form a plurality of conduction windows on the at least one pair of electrodes that are aligned with the plurality of conduction windows in the silicon overmold. In some variations, the conduction windows are dispersed substantially around the entire circumference of the cuff portion.

Any of these apparatuses (devices, systems, etc.) may also include a non-volatile memory in communication with the microprocessor, wherein the microprocessor is programmed to log dose compliance in the non-volatile memory. Any of these apparatuses may also or alternatively include a plurality of shape memory metal struts configured to bias the cuff portion into the closed configuration. These apparatuses may include a thermal protection circuit with a thermistor in electrical communication with the power receiving coil, the thermal protection circuit configured to provide an open circuit when the thermistor measures a temperature that equals or exceeds a predetermined or set temperature. The predetermined or set temperature may be about 41.5 degrees Celsius. In some variations the thermistor is positioned proximate the power receiving coil. In some variations, the thermistor is positioned proximate one of the electrodes.

Any of these apparatuses may include a ferrite disposed within the power receiving coil.

The electrodes may be made of any appropriate material, including, e.g., made at least in part of platinum or a platinum alloy. The material may be selected and/or arranged to avoid interfering with the inductive powering and/or communication. In some variations the at least one pair of electrodes are made at least in part of a platinum-iridium alloy. The at least one pair of electrodes may be spring cut.

For example, a batteryless and leadless microregulator for nerve stimulation may include: a power receiving coil configured to inductively receive a power signal; a microprocessor powered by the electrical energy received by the power receiving coil; a modulator and a demodulator in electrical communication with the power receiving coil and the microprocessor for receiving and transmitting information from the power signal; at least one pair of electrodes configured to deliver electrical stimulation using the electrical energy received by the power receiving coil; and an overmold that encapsulates the power receiving coil, the microprocessor, the modulator, the demodulator, and at least a portion of the pair of electrodes, the overmold having a nerve channel and a slit that provides access to the nerve channel, wherein the overmold is configured to adopt an open configuration in which the slit is open to expose the at least one pair of electrodes within the nerve channel, and a closed configuration in which the slit is closed, wherein the microprocessor is configured to apply energy to the at least one pair of electrodes only when the power signal is being received by the power receiving coil, further wherein the microprocessor and electrodes are not connected to a battery.

Also described herein are methods of using batteryless and leadless microstimulators. For example, a method for stimulating a nerve may include: inductively applying energy to an implanted leadless and batteryless microregulator using an external inductive coil, the implanted leadless and batteryless microregulator having a nerve channel encircling the nerve and at least a pair of electrodes disposed within the nerve channel; and delivering an electrical stimulation to the nerve from the at least one pair of electrodes while inductively applying energy to the implanted leadless and batteryless microregulator, wherein the implanted leadless and batteryless microregulator is configured to condition the electrical stimulation based at least in part on a signal transmitted with the inductively applied energy.

The electrical stimulation may have an amplitude of up to 3 mA and a duration of up to 30 seconds. The electrical stimulation may be delivered as a plurality of sub-bursts, each sub-burst having a duration of about 1-5 seconds.

The method nerve may be any appropriate never or nerve bundle. For example, the nerve may be the vagus nerve, such as the vagus nerve in a cervical region of the neck. The nerve may be a sub-diaphragmatic portion of the vagus nerve. For example, the nerve may be a peripheral nerve.

BRIEF DESCRIPTION OF THE DRAWINGS

FIG. 2 is a front view depicting an implanted nerve cuff with strain relief.

FIG. 3 is a front view depicting an implanted nerve cuff with suture holes.

FIG. 4 is an open view depicting the nerve cuff with suture holes of FIG. 3.

FIG. 5 is a top view depicting a closing device for the implanted nerve cuff of FIG. 1A.

FIG. 10A shows an end view, FIG. 10B is a side perspective view, FIG. 10C is a side view, and FIG. 10D is a longitudinal section through the device attached to a nerve, showing internal features including a microstimulator.

FIG. 11A shows an end view, FIG. 11B is a side perspective view, FIG. 11C is a side view, and FIG. 11D is a longitudinal section through the device attached to a nerve, showing internal features including a microstimulator.

FIGS. 22A-22H illustrate steps for inserting a nerve cuff such as the nerve cuffs described herein.

FIG. 24D is a block diagram schematically illustrating the microstimulator and the charger.

FIG. 25 illustrates one variation of an external system programmer/controller wirelessly connected to a microstimulator.

FIGS. 27A-27D show top, side, side perspective and end views, respectively, of a ferrite resonator that may be used as part of the microstimulators described herein.

FIG. 38 is one example of a system including a microstimulator/microregulator that is implanted along with a POD, a wearable charger that may be modified herein, and software/prescription pad that may interface with the charger to modify activity of the microstimulator.

FIG. 42 is an example of a tester coupled to a cable or wirelessly coupled to a controller.

FIGS. 46A-46D illustrate different head designs that may be used.

FIG. 47 describes another example of a system including a microstimulator/microregulator that is implanted along with a POD, a wearable charger that may be modified herein, software/prescription pad for interfacing with the charger and implant, and a tester (surgical tester) including a probe (test probe).

FIG. 50A shows a side view of the long axis of the pillow recharger showing the electromagnetic field lines.

FIG. 50B shows a perspective view of the pillow recharger and the magnetic field lines emanating from the transmitter coil.

FIGS. 56A-56D schematically illustrate an example of a batteryless microstimulator (MS).

FIGS. 57A-57C schematically illustrate an example of a batteryless MS in which the PCB substrate is formed from a high temperature melting point LCP 5500, and is flexible and inert, so that it can be implanted around a nerve as described herein.

FIGS. 65A-65D schematically illustrate implantation of a batteryless S.'

FIGS. 66A-66C illustrate an example of a batteryless microstimluator (MS) configured to be bistable, so that it may be easily snapped onto a nerve by transitioning from a stable planar configuration to a stable longitudinally curved/curved configuration over the nerve, as illustrated.

FIGS. 68A-68E illustrates an insertion tool that may be used to implant a batteryless microstimluator apparatus as described herein, configured to retain the apparatus in an "open" configuration until placed over the never, then allowing it to relax into a stable "closed" configuration around the nerve.

DETAILED DESCRIPTION

Figure 1B:
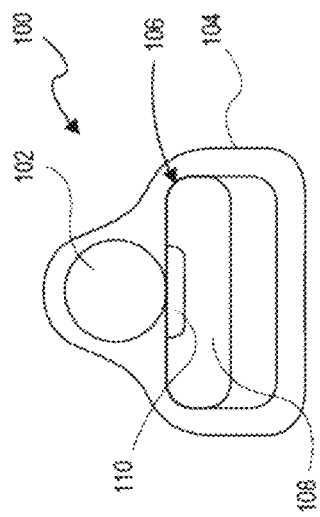
FIG. 1B is a top view depicting the implanted nerve cuff with stimulation device of FIG. 1A.

Described herein are methods and apparatuses (e.g., devices and systems) for vagus nerve stimulation to treat inflammation. Any of the apparatuses and methods described herein may be used with any vagus nerve stimulation (e.g., with any micro-stimulator), but may be adapted in particular for use in sub-diaphragmatic vagus nerve stimulation. In particular, the methods and apparatuses may be used to stimulate the sub-diaphragmatic vagus nerve to treat inflammation and/or inflammatory disorders such as hay fever, atherosclerosis, arthritis (e.g., rheumatoid, bursitis, gouty arthritis, polymyalgia rheumatic, etc.), asthma, autoimmune diseases, chronic inflammation, chronic prostatitis, glomerulonephritis, nephritis, inflammatory bowel diseases, pelvic inflammatory disease, reperfusion injury, transplant rejection, vasculitis, myocarditis, colitis, etc. The apparatus may be a microstimulator (also referred to herein as a "MS", "nerve stimulator", "microcontroller", "MC" or simply "implant") that is configured to deliver appropriate electrical stimulation to a nerve. The electrical stimulation can modulate the activity of the nerve and cause a wide variety of effects. For example, electrical stimulation of the vagus nerve can result in a reduction of inflammation through activation of the cholinergic anti-inflammatory pathway. The microstimulator may be applied by itself or within or as part of a nerve cuff (referred to herein as a "protection and orientation device" or POD). The microstimulator ("MR") or POD or combined MR/POD may be specifically adapted for use in the abdomen and placement sub-diaphragmatically. For example, the apparatus may be tethered or tetherable to prevent migration or "loss" of the apparatus within the abdomen. MS, POD or MS/POD may also be adapted for placement specifically on the sub-diaphragmatic region, including but not limited to the sub-diaphragmatic vagus Nerve.

When configured to sub-diaphragmatic vagus nerve stimulation, the apparatuses described herein may be preferred over carotid vagus nerve application. In such variations, a single implant (e.g., single leadless microstimulator, including those described herein) may be adapted for sub-diaphragmatic implantation. Such implants may be adapted for sub-diaphragmatic implantation by including one or more features including: a location and/or orientation emitter (configured to emit a wireless signal indicating implant location and orientation, particularly of an inductive coil(s) within the implant), multiple inductive coils for communication (including charging), a controller adapted to deliver a large simulation dose (e.g., a single pulse or bursts of pulses having between 6.5 and 20 V for a dose duration of between 0.1 second and 1000 seconds (e.g., between 0.3 s and 500 s, between 0.5 s and 100 s, etc.), followed by a low-power, "off" time during which the implant may not apply stimulation; this off time may be between 1 hour and 48 hours (e.g., between 2 hours and 48 hours, between 3 hours and 48 hours, between 4 hours and 36 hours, greater than 2 hours, greater than 3 hours, greater than 4 hours, etc.). The multiple inductive coils may be arranged as a biaxial or tri-axial array of coils. The coils may be arranged (e.g., wrapped, embedded, etc.) on an outer housing of the microstimulator. As will be described in greater detail below, any of these implants may include a magnetically permeable material. Any of these implants may also communicate with a charger which may be worn (e.g., around the abdomen, as a belt, sash, pant, bandolier, etc.) or configured for lying atop (e.g., pad, such as a mattress, pillow, etc.).

Either or both the implant and the charger may be configured to orient the inductive coils between the two devices. For example, the charger may be configured as a three-axis coil(s) so that a plurality of orientations may be used to charge and/or communication. The charger may actively determine which orientation is optimal based on communication with the implant, and may track and use the determined orientation. For example, concurrent or sequential signals (e.g., power) may be applied from each of a plurality of coils having different orientations, and a load detected from the implant reviewing and/or communicating with the charger may allow the charger to optimize (e.g., orient) the applied power to the coil(s) in the appropriate orientation. Any of the chargers described herein may radially cycle through fields from the inductive coil(s), so that the orientation of the applied field changes. Any of the chargers described herein may be tunable, including those configured as a flexible and/or wearable apparatus (e.g., belt), as the orientation of the apparatus, particularly in sub-diaphragmatic implants, may as this region may be mobile. In general, when performing sub-diaphragmatic stimulation, the applied stimulation may be greater than that previously described for cervical vagal stimulation. Typically between 10% and 150% (or more) greater intensity may be applied when performing sub-diaphragmatic stimulation compared to carotid stimulation. For example electrical stimulation may be applied at greater than 6.5 V (e.g., between 6.5 and 20V), although lower intensities (e.g., between 0.5 V and 6.5 V may be used). Typically the voltage does not need to be adjusted during a treatment course, but may be maximally applied during the entire treatment course.

In general, the methods and apparatuses described herein for sub-diaphragmatic stimulation may be used with (or as part of) a laparoscopic surgical approach to placing MR/POD, e.g., on the posterior sub-diaphragmatic vagus nerve. In some variations the methods and apparatuses may be used as part of a Natural orifice transluminal endoscopic surgery (NOTES) procedure.

Examples of microstimulators and apparatuses for holding them onto the sub-diaphragmatic vagus nerve (e.g., a protection and orientation or "POD" device, also referred to herein as a nerve cuff) for use in sub-diaphragmatic stimulation of the NCAP are described herein as well. The methods and apparatuses described herein that are specific to sub-diaphragmatic NCAP stimulation have, in preliminary work, shown many advantages over traditional cervical Vagal placement. For example, these methods and apparatuses typically have fewer adverse events caused by stimulation. Further, these methods and devices may be less safety and time critical, therefore not requiring emergency shutoff as often or as precisely as cervical vagus stimulation. In addition, fewer cardiac effects have been seen with sub-diaphragmatic placement, and no laryngeal adverse events. Finally, there may be a substantial reduction in undesirable muscle stimulation and resulting pain.

The methods and apparatuses described herein may also alleviate the requirement for titration of stimulation patterns, due to a large predicted therapy window that may be used with sub-diaphragmatic stimulation of the NCAP pathway. This may also prevent or minimize postoperative pain. Sub-diaphragmatic stimulation may also reduce the risk of hemorrhaging due to insertion of the implant. Finally, the resulting microstimulator devices may be made larger, allowing greater energy storage and requiring less frequent charging.

In practice, the microstimulator for use in sub-diaphragmatic NCAP stimulation may be inserted onto a nerve forming a portion of the NCAP pathway below the diaphragm by any appropriate method. In particular, it may be helpful to connect (and tether) a microstimulator onto the posterior sub-diaphragmatic vagus nerve.

For example, a device such as the ones described below, or adapted from these devices, may be inserted by first creating several small incisions (0.5-1.5 cm) in abdomen and insufflating the abdomen with carbon dioxide gas. Two or more trocars may be inserted for access and/or to illuminate the surgical site. It may be helpful to displace internal organs such as the liver with a retractor to expose the posterior sub-diaphragmatic vagus nerve. Once exposed, the nerve may be separated from the tissue so that a POD may be placed under nerve, e.g., by longitudinally introducing a POD on nerve. Once the POD is applied, the microstimulator (MR) may be introduced into the POD, e.g., by separating the seam of the POD. The MR may then be sealed into the POD. The MR and POD may be any of those shown and described in Part II, below, or adapted specifically for sub-diaphragmatic implantation and operation. For example, the MR/POD may be configured to be tethered or attached within the abdominal cavity to prevent migration that may alter the position and/or orientation of the apparatus. This may be a particularly acute issue for sub-diaphragmatic implantation compared to cervical implantation. For example, a POD and/or MR may include one or more clips, anchors, and/or filaments for anchoring/tethering the device such as a polymer filament holding component, or the like.

In general, the methods and apparatuses described herein may be adapted to address needs specific to the sub-diaphragmatic placement. For example, the nerve, e.g., the posterior sub-diaphragmatic vagus nerve, may be more difficult to access without damage to the nerve or surrounding tissue. Further, when inserting in this region of the body, particularly minimally invasively, the surgical tools and instruments may have a limited range of motion resulting in a loss of dexterity, and the region may allow only poor depth perception. Thus, it may be helpful to use a tool to manipulate the nerve without exerting too much force or trauma to the nerve (as it may be difficult to accurately judge the force exerted on the nerve in this location). Traditional surgical tools, such as a harmonic scalpel, may damage nerve, while blunt instrument that may be used to separate the nerve are known to cause chronic inflammation.

To address the implantation issues, the apparatus may be configured to provide stimulation (test stimulation) during implantation, and provide an alert to the surgeon when the nerve is triggered, indicating that the apparatus is properly positioned on the nerve. Nerve monitoring may also be performed, e.g., monitoring afferent stimulation of the vagus from a more proximal site, etc.

As mentioned above, another challenge to the sub-diaphragmatic implantation and stimulation of the NCAP is that this sub-diaphragmatic location may make it difficult to retain the MR and/or POD both during implantation and after implantation. Further, it may also be difficult for an implanted MR/POD to be located (e.g., for charging, etc.) post-implantation. In essence, the device may be "lost" in abdomen. As mentioned above, in any of these variations the use of POD and/or MR that is attached to tissue that is not in direct contact with the nerve may address the problem of wandering and/or lost implants, by anchoring or tethering the MR/POD in position. For example, a tether (e.g., a polymer filament holding component or device) may be used and/or integrated into the POD. In some variations a clip may be used to hold the device along the POD closing seam and can be pulled off after securing the device with POD. In some variations a tether may be anchored to saddle. This tether may be cut short or off after securing the device with POD, or it may be left in place.

Retrieval and/or repositioning of the apparatus may be enhanced by using a vacuum line that attaches to an end-cap and is removed or removable after securing the device with POD.

A detector may also be used either during or after implantation of the apparatus. For example, an electronic wand/probe may be configured to locates device electronically may be used to confirm the location/position and/or orientation of the apparatus. For example, a detector may include a multi-axis inductor in a sterile plastic shield that radiates power at resonant frequency and monitors the mutual inductance; this may provide feedback from the implant. As the mutual inductance increases, the device may signal to the operator.

Any of these methods may also include a retriever, such as an apparatus including a vacuum line that can be used to retrieve found device or device to be explanted.

When a non-invasive, rechargeable microstimulator is used, as described herein in some variations, the implant may be inductively charged. In contrast to the cervical NCAP stimulation previously described, sub-diaphragmatic NCAP stimulators (MR) maybe more difficult to charge based on their position deeper within the body. Thus the charging design for a charger of the implant in the abdomen may require more power and it may be difficult to locate the microregulator (MR) within the abdomen.

Figure 28:
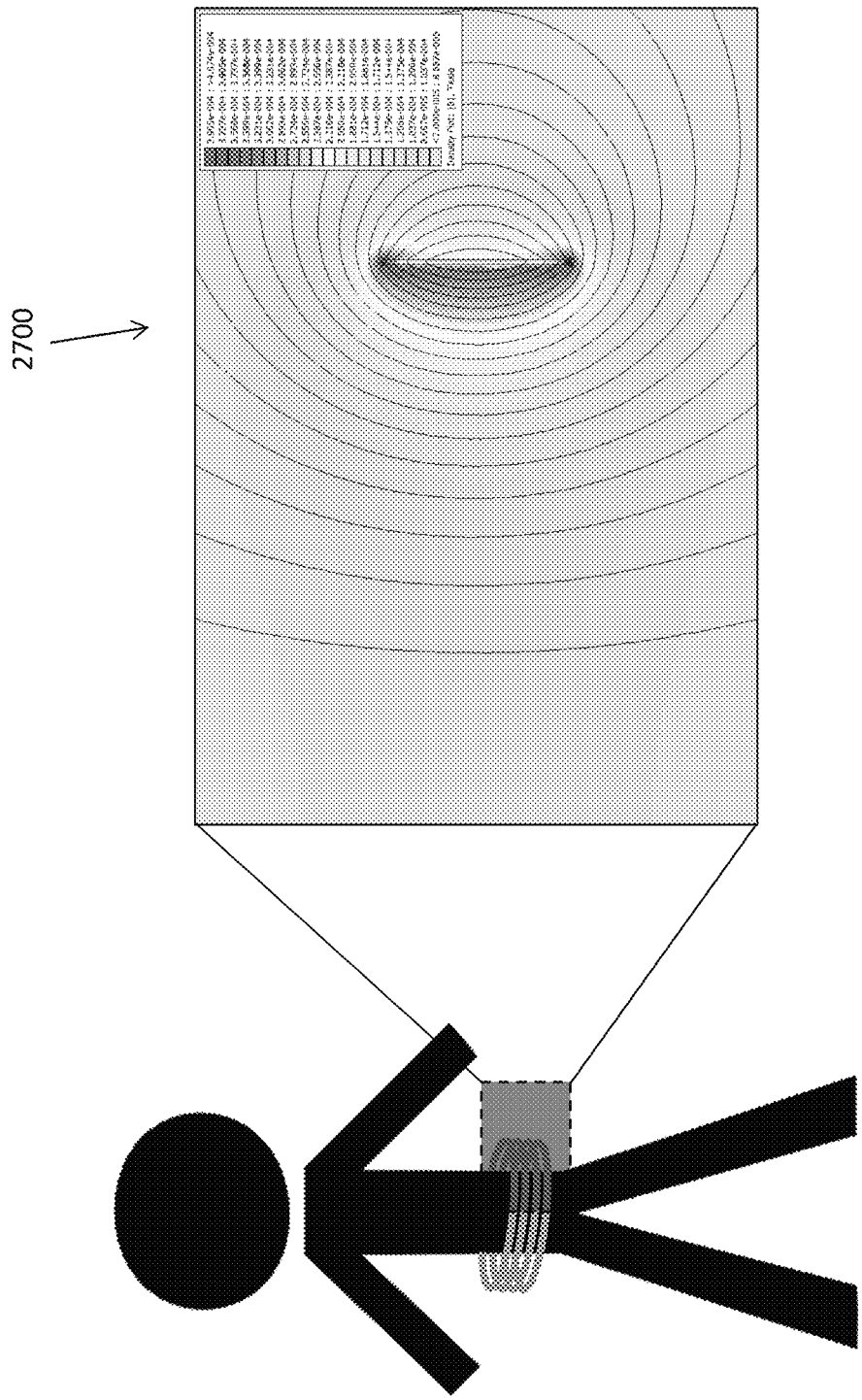
FIG. 28 illustrates one example of a belt-style charger that could be used to charge an abdominally-implanted MR as described herein.

For example, FIG. 28 illustrates an example of a charging apparatus configured as a belt that may be worn with a subject having an implanted sub-diaphragmatic apparatus. In this example, as shown in the model, the apparatus may be configured to produce a field of over 100 T throughout a cylindrical volume approximately 7.5" in height. This field may be sufficient to deliver the maximum power required by a microregulator/microstimulator (MR). In this example, the belt circumference is approximately 38" (though it may be more or less), the belt height is between 2 and 8 inches (e.g., in FIG. 28 the belt height is 4"). Any appropriate number of turns may be used. In the exemplary device shown in FIG. 28, the number of turns×current corresponds to 50 Amp turns. The conductor used in the exemplary device of FIG. 28 is a 10 AWG equivalent, such as a Litz wire or thin sheet.

In general, a low-resistance connection is required for each turn at the belt latch, e.g. double or triple connection per turn. Resistances of less than 0.2Ω, Q>200 and P<5 W can be achieved with this design. To account for different waist shapes, a number of sets of tuning capacitors could be available and selected either electronically or manually (e.g. by switch) during an initial fitting session or, if the switching is automatic, whenever the belt is worn.

In FIG. 28, the right side of the FIG. 2700 shows a density plot of the magnetic field intensity, in Tesla, showing that the field strength penetrating into the abdomen of the wearer to a depth sufficient to charge and/or communicate with an implanted (in a sub-diaphragmatic site) microcontroller/ microregulator (MR), e.g., between $4e^{-4}$ and $1.5e^{-4}$ T.

Neurostimulators and PODS

Figure 1C:
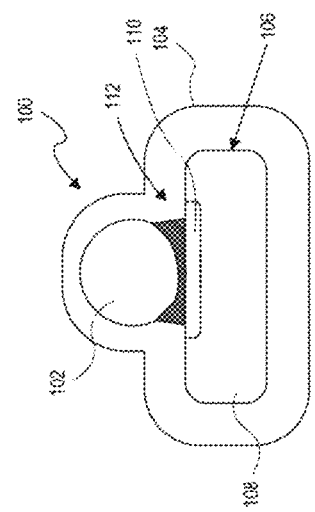
FIG. 1C is a top view depicting the implanted nerve cuff with stimulation device.
Figure 1A:
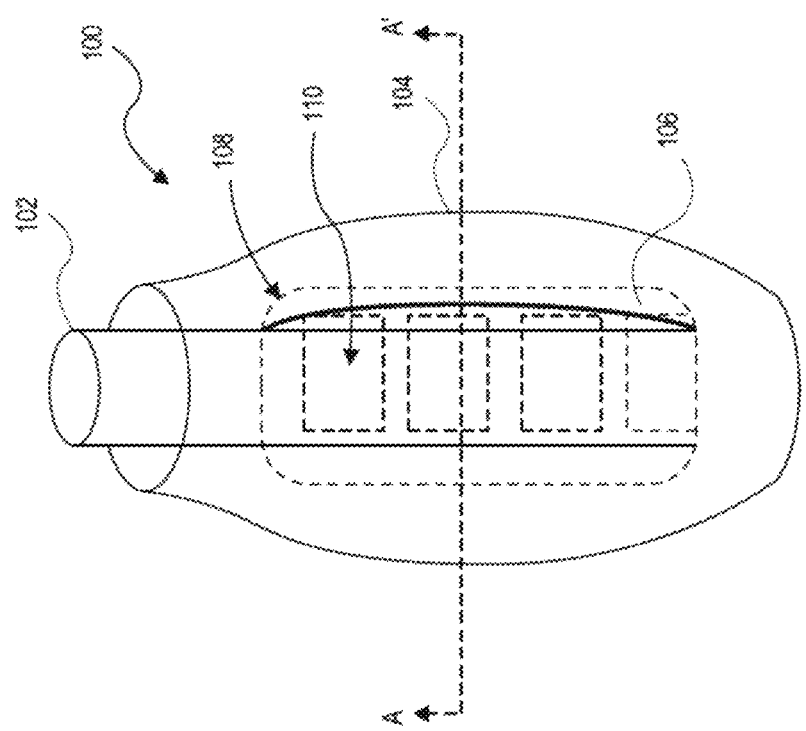
FIG. 1A is a perspective view depicting one variation of a nerve cuff with stimulation device implanted proximate a nerve.
Figure 24A:
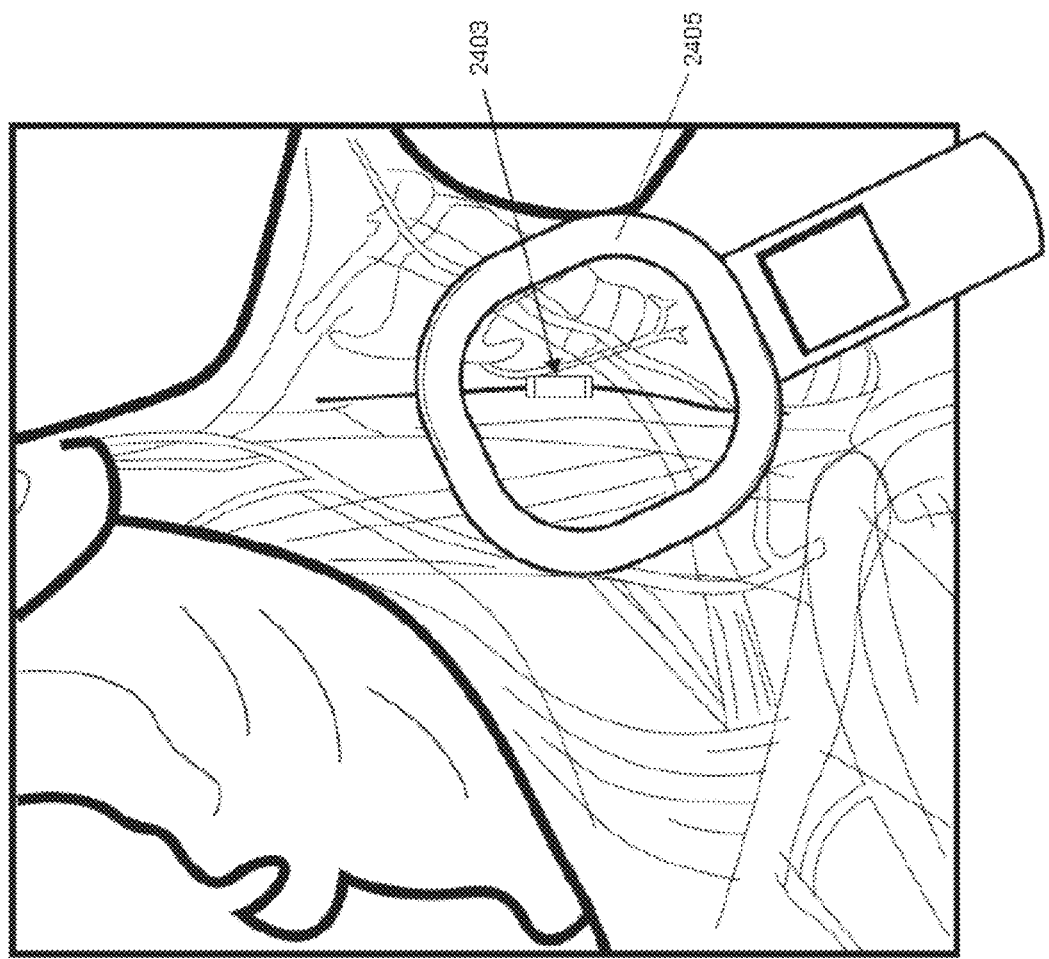
FIG. 24A shows one variation of a system for modulating chronic inflammation including a leadless microstimulator (shown connected to the vagus nerve) and an external charger/controller.
Figure 26A:
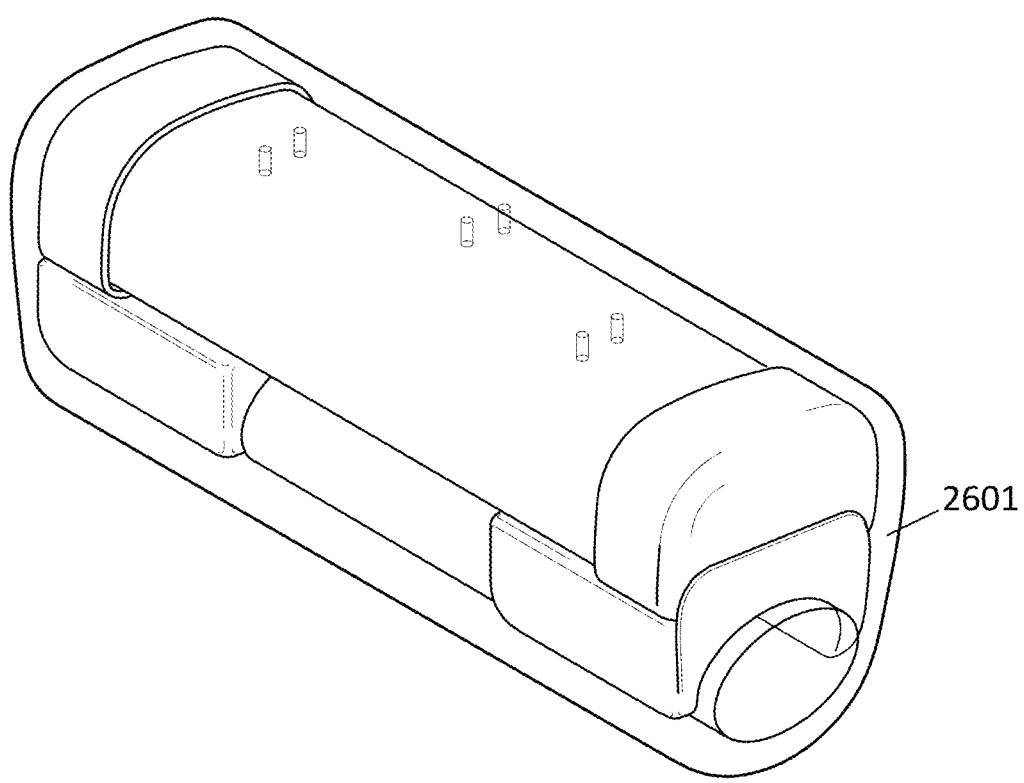
FIG. 26A shows one variation of a microstimulator in a POD configured to surround a nerve of the inflammatory reflex.
Figure 26B:
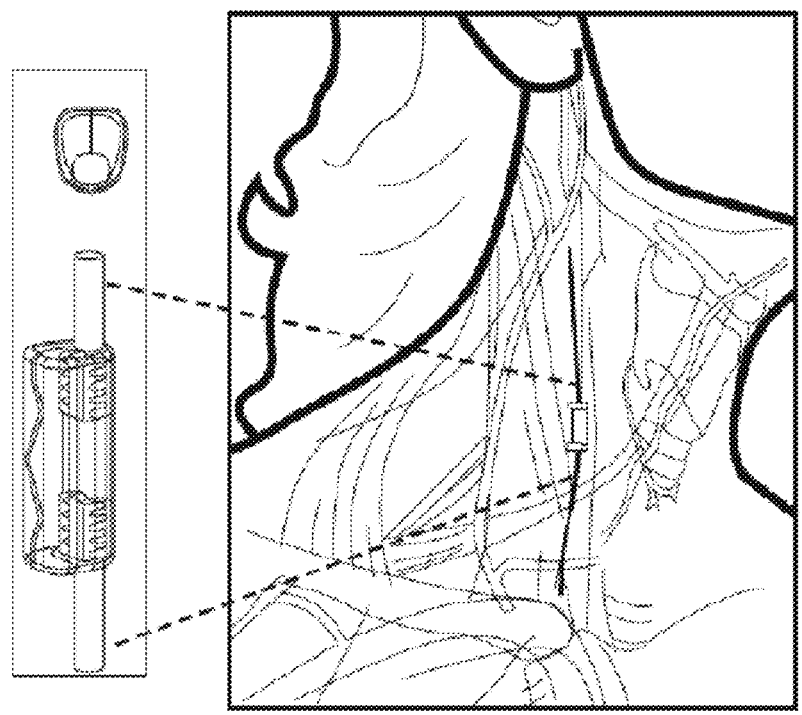
FIG. 26B shows an enlarged view of the microstimulator and POD.
Figure 26C:
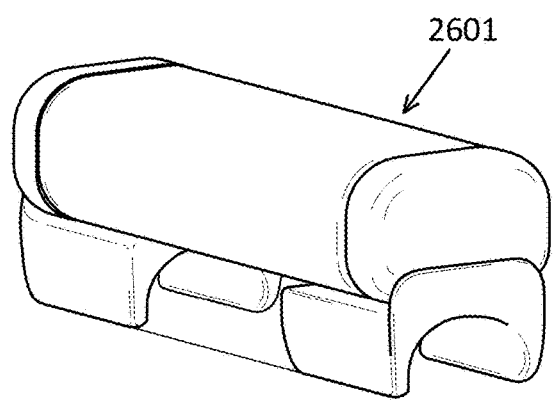
FIG. 26C shows another variation of a microstimulator.
Figure 26D:
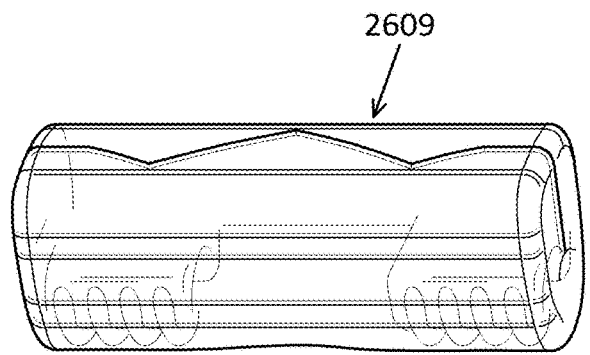
FIG. 26D shows the microstimulator of FIG. 26C within a POD.

Referring to FIG. 1A, one example of a nerve cuff 100 adapted for holding a stimulation device is coupled to a nerve 102. Although this cuff and microstimulator may be used for cervical vagus stimulation (as shown in FIGS. 24A, 25 and 26B), any of the apparatuses described herein may be adapted for use in the sub-diaphragmatic region. In FIG. 1A, the nerve 102 can comprise any nerve in the human body targeted for therapeutic treatment, such as, for example, the vagus nerve. Nerve cuff adapter 100 generally comprises an outer carrier or cuff 104 body that can comprise any of a variety of medical grade materials, such as, for example, Silastic™ brand silicone elastomers, or Tecothane™ polymer. Although this example is described (see below, FIGS. 24A, 25 and 26B) for attaching the cervical region of a vagus nerve, it may be adapted as described herein for use in a sub-diaphragmatic site, including in particular the posterior sub-diaphragmatic vagus nerve. For example, the PODS described herein and/or the MR may include additional clips, tethers or the like for assisting in securing the apparatus to the posterior sub-diaphragmatic vagus nerve.

In general, a nerve cuff including a cuff 104 body having (or forming) a pouch or pocket 106 for removably receiving an active, implantable stimulation device 108 having one or more integrated, leadless electrodes 110 on a surface of stimulation device 108 proximate nerve 102. As illustrated in FIGS. 1A and 1B, nerve cuff 100 wraps around nerve 102 such that electrodes 110 are positioned proximate nerve 102.

Contacts or electrodes 110 can be positioned directly against nerve 102, as illustrated in FIG. 1B, or in close proximity to nerve 102, as illustrated in FIG. 1C. Referring specifically to FIG. 1C, close proximity of electrodes 110 and nerve 102 will leave a gap or space 112 that may naturally be filled with fluid or connective tissue. In one embodiment of the invention, electrodes 110 and/or the inner surface of cuff body 104 can include optional steroid coatings to aid in reducing the local inflammatory response and high impedance tissue formation.

In one embodiment, the pocket 106 for containing the stimulation device 108 is defined by the open space between the nerve 102 and the inner surface of the cuff body 104. Stimulation device 108 can be passively retained within pocket 106 by the cuff body 104, or can be actively retained on cuff body with fastening means, such as, for example, sutures. In other embodiments, pocket 106 can comprise a pouch-like structure attached to cuff body 104 into which stimulation device 108 can be inserted. Stimulation device 108 can be passively retained within a pouch-like pocket by simply inserting the device 108 into the pocket or can be actively retained with fastening means. A pouch-like pocket can be positioned either in the interior or on the exterior of cuff body 104. Pouch-like pocket 106 and/or cuff body 104 can include access openings to allow electrodes to be positioned directly proximate or adjacent to nerve 102.

Figure 9A:
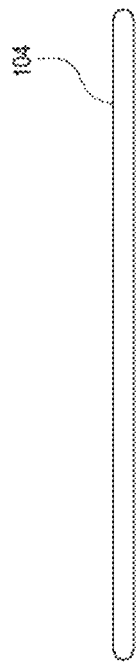
FIGS. 9A and 9B show side views through a section of the cuff body wall, indicating uniform and varying thicknesses, respectively.
Figure 9B:

Cuff body 104 can have a constant thickness or a varying thickness as depicted in FIGS. 9A and 9B. The thickness of cuff body 104 can be determined to reduce the palpable profile of the device once the stimulation device is inserted. In one embodiment, the thickness of cuff body can range from about 1 to about 30 mils, or from about 5 to about 20 mils. In one embodiment shown in FIG. 9B, cuff 104 can have a greater thickness at a top and bottom portion of the cuff and a smaller thickness in a middle portion where the stimulation device is contained.

A key obstacle to overcome with implanting stimulation devices proximate nerves or nerve bundles is attaching a rigid structure that makes up the stimulation device along a fragile nerve in soft tissue. In one embodiment of the invention, this issue is resolved by encasing nerve 102 and device 108 in a cuff body 104 that comprises a low durometer material (e.g., Silastic™ or Tecothane™) as described above, that conforms around nerve 102. Further, as illustrated in FIG. 2, cuff body 104 can comprise strain reliefs 114 on its ends that reduce or prevent extreme torsional rotation and keep nerve 102 from kinking. Strain reliefs 114 can coil around nerve 102, and are trimmable to a desired size, such as the size of nerve 102. Further, strain relief 114 can be tapered. In some variations, the lateral ends of the nerve cuff, forming the channel into which the nerve may be place, are tapered and have a tapering thickness, providing some amount of support for the nerve. In some variations, the channel through the nerve cuff in which the nerve may sit, is reinforced to prevent or limit axial loading (e.g., crushing) of the nerve or associated vascular structures when the nerve is within the cuff.

Given the design or architecture of cuff body 104, any vertical movement of cuff body 104 on nerve 102 is not critical to electrical performance, but can result in friction between device 108 and nerve 102 that could potentially damage nerve 102. For that reason, device 108 should readily move up and down nerve 102 without significant friction while being sufficiently fixated to nerve 102 so that eventually connective tissue can form and aid in holding device 108 in place. The challenge is stabilizing device 108 so that it can be further biologically stabilized by connective tissue within several weeks.

Nerve cuff 100 should not be rigidly stabilized to surrounding muscle or fascia that will shift relative to the nerve. Therefore, referring to FIGS. 3 and 4, nerve cuff 100 can further comprise connection devices, such as suture holes or suture tabs, for coupling and stabilizing cuff body 104 with device 108 to at least one of the nerve bundle or nerve 102, and the surrounding sheath that contains nerve 102. In one embodiment of the invention, for example, as shown in FIG. 3, cuff body 104 can comprise suture holes 116 that can be used with sutures to couple cuff 104 body with device 108 to the surrounding nerve sheath. In an alternative embodiment of the invention, shown in FIG. 4, suture tabs 118 with suture holes 116 extend from one or both sides of cuff body 104.

Several stabilizing mechanisms can be used, including suture tabs and holes, staples, ties, surgical adhesives, bands, hook and loop fasteners, and any of a variety of coupling mechanisms. FIGS. 3 and 4, for example, illustrates suture tabs and holes that can be fixed to the surrounding sheath with either absorbable sutures for soft tissue or sutures demanding rigid fixation.

FIG. 5 illustrates sutures 120 that clamp or secure cuff body 104 with device 108 to a surgeon-elected tension. Sutures 120 can be tightened or loosened depending on the level of desired stability and anatomical concerns. As shown in FIG. 5, a gap 122 can be present so long as cuff adapter 100 is sufficiently secured to nerve 102, with a limit set to a nerve diameter to prevent compression of the vasculature within nerve 102. Surgical adhesives (not shown) can be used in combination with sutures 120 on surrounding tissues that move in unison with the neural tissue.

Muscle movement against cuff adapter 100 can also transfer undesired stresses on nerve 102. Therefore, in an embodiment of the invention, low friction surfaces and/or hydrophilic coatings can be incorporated on one or more surfaces of cuff body 104 to provide further mechanisms reducing or preventing adjacent tissues from upsetting the stability of nerve cuff 100.

Figure 6:
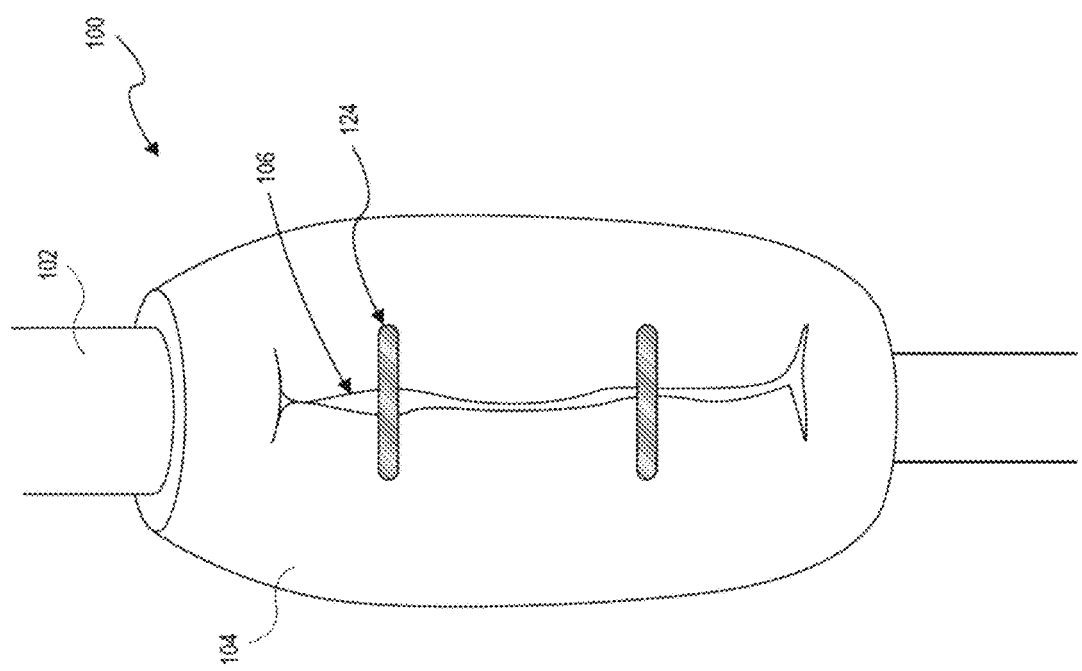
FIG. 6 is a perspective view depicting marsupializaton of the stimulation device within a pocket of the nerve cuff of FIG. 1A.

FIG. 6 illustrates a nerve cuff 100 with a stimulator device removably or marsupially secured within pocket or pouch 106 of cuff body 104. By the use of recloseable pouch 106, active stimulator device 108 can be removed or replaced from cuff body 104 without threatening or endangering the surrounding anatomical structures and tissues. Device 108 can be secured within cuff body 104 by any of a variety of securing devices 124, such as, for example, sutures, staples, ties, zippers, hook and loop fasteners, snaps, buttons, and combinations thereof. Sutures 124 are shown in FIG. 6. Releasing sutures 124 allows access to pouch 106 for removal or replacement of device 108. Not unlike typical cuff style leads, a capsule of connective tissue can naturally encapsulate nerve cuff 100 over time. Therefore, it will most likely be necessary to palpate device 108 to locate device 108 and cut through the connective tissue capsule to access sutures 124 and device. The removable/replaceable feature of nerve cuff 100 is advantageous over other cuff style leads because such leads cannot be removed due to entanglement with the target nerve and critical vasculature.

As discussed supra, compression of nerve 102 must be carefully controlled. Excess compression on nerve 102 can lead to devascularization and resulting death of the neural tissue. Compression can be controlled by over-sizing or rightsizing nerve cuff 100, so that when pocket sutures 124 are maximally tightened, the nerve diameter is not reduced less that the measured diameter. Cuffs formed from Silastic™ or Tecothane™ materials are relatively low cost, and therefore several sizes can be provided to the surgeon performing the implantation of nerve cuff 100 to better avoid nerve compression.

Figure 7A:
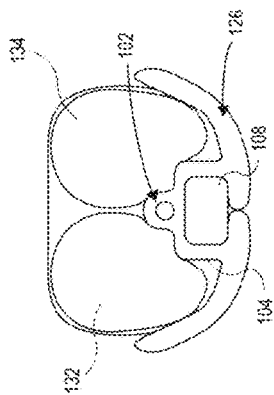
FIG. 7A is a top view depicting a nerve cuff having a conforming shield.
Figure 7B:
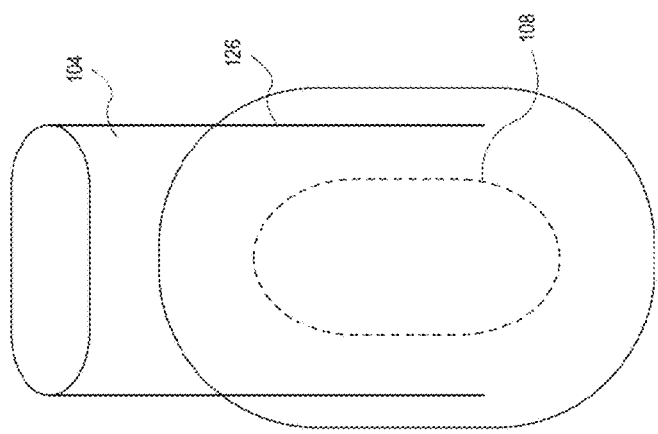
FIG. 7B is a front view of the nerve cuff of FIG. 7A.

Miniature stimulators, such as device, are still large enough to be felt and palpated by patients as are state-of-the-art commercial cuff systems. Referring to FIGS. 7A and 7B, to avoid such palpation, nerve cuff 100 can further comprise a protecting shield 126 conforming to the shape of the anatomical structures, such as in the carotid sheath. In this embodiment, nerve cuff 100 is secured around the vagus nerve, while isolating device 108 from contact with both the internal jugular vein (IJV) 132, and common carotid artery 134. Shield 126 then further isolates device 108 from other surrounding tissues. It is critical to minimize the profile of the entire cuff adapter 100 while maintaining the compliance of such materials as Silastic™ or Tecothane™. In one embodiment of the invention, protective shield 126 is formed from a PET material, such as Dacron®, optionally coated with Silastic™ or Tecothane™ forming a thin and compliant structure that will allow for tissue separation when required.

Figure 8A:
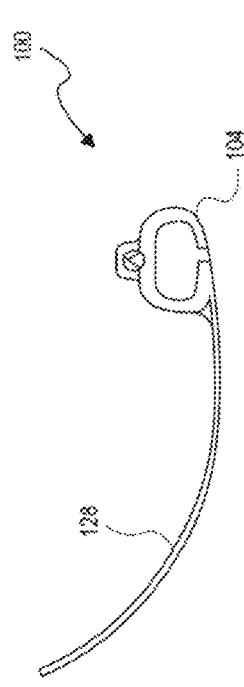
FIG. 8A is a top view depicting an open nerve cuff.
Figure 8B:
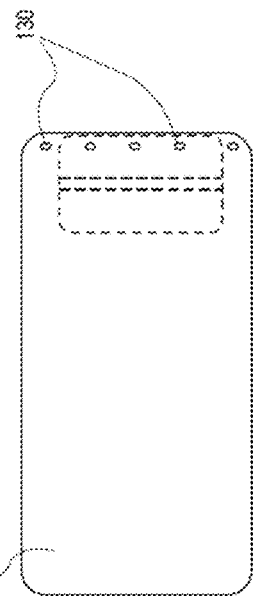
FIG. 8B is a front view of the nerve cuff of FIG. 8A.
Figure 8C:
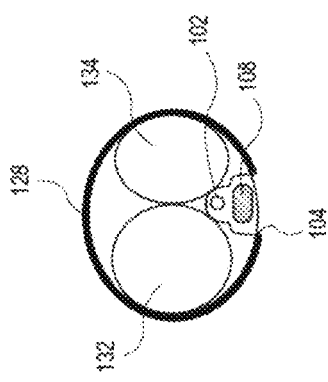
FIG. 8C is a top view depicting the nerve cuff of FIG. 8A in a closed configuration.

When a nerve does not provide sufficient structural strength to support nerve cuff adapter 100, collateral structures can be included in or on cuff body 104. Because of a high degree of anatomical variance such a scheme must demand the skill of the surgeon to utilize a highly customizable solution. FIG. 8A illustrates a variable size nerve cuff 100 with a wrappable retainer portion 128 extending from cuff body 104. As shown in FIG. 8C, cuff body 104 is secured around nerve 102, while retainer portion 128 is secured around the sheath or other surrounding anatomical structures, such as the IJV 132 and/or carotid artery 134. As shown in FIG. 8B, wrappable retainer portion 128 can include securing devices 130, such as suture holes, for securing the entire nerve cuff 100 around the desired anatomical structures. This configuration allows for access to device 108 through pocket 106 as in previous embodiments, while adapting to a multitude of anatomical variations to obtain the desired stability of nerve cuff 100 on nerve 102.

FIGS. 10A-10D illustrate a variation of a nerve cuff that includes a cuff body forming a channel (into which a nerve may be fitted) and an slit formed along the length of the nerve cuff body. In this example, the nerve cuff body also includes a pocket region within the cuff body positioned above the nerve channel. The top of the body (opposite from the nerve channel) includes a long slit 1003 along its length forming on opening. The cuff body may be along the slit by pulling apart the edges, which may form one or more flaps. In the example shown in FIG. 10A, the slit may be split open to expose the inside of the nerve cuff and allow the nerve to be positioned within the internal channel, so that the cuff is positioned around the nerve. The same split may be used to insert the microcontroller as well. In some variations a separate opening (slit or flap) may be used to access the pocket or pouch for the microcontroller.

Figure 10A:
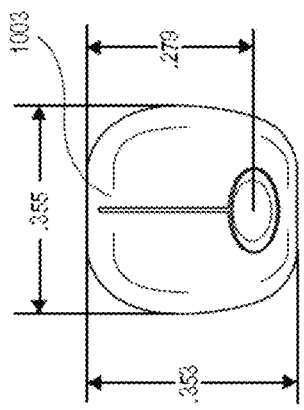
FIGS. 10A-10D illustrate one variation of a nerve cuff as described herein.
Figure 10B:
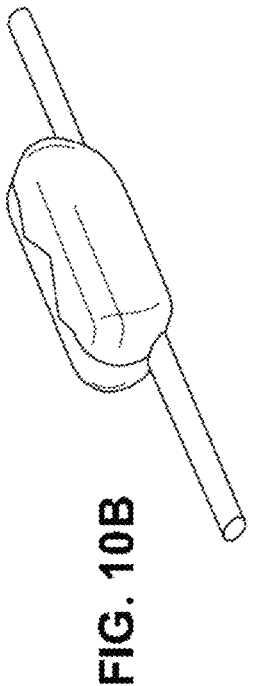
Figure 10C:
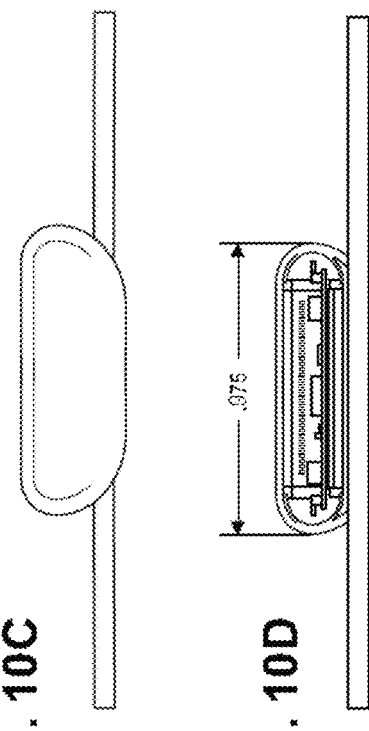
Figure 10D:
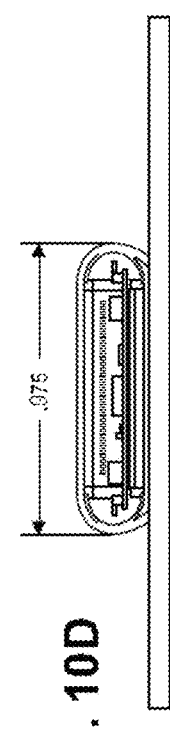

FIG. 10B shows a perspective view of the nerve cuff holding a microcontroller after it has been inserted onto a nerve (e.g., the vagus nerve). FIG. 10C shows a side view of the same. FIG. 10D shows a section though the view of FIG. 10C, illustrating then nerve within the channel formed through the nerve cuff, and a microstimulator held snugly within the nerve cuff so that the microstimulator is in electrical communication with the nerve via a shared surface between the two. In some variations, as discussed below, the microstimulator is held in a separate, possibly isolated, compartment and electrical contact with the nerve is made by one or more internal leads that couple the microstimulator with the nerve through an internal contact.

The exemplary cuff shown in FIGS. 10A-10D has a conformal configuration, in which the wall thickness is relatively constant, as can be seen from the sectional view in FIG. 10D. In contrast, FIGS. 11A-11D illustrate a variation of a nerve cuff in which the wall thickness varies along the perimeter. This non-uniform thickness may effectively cushion the device relative to the surrounding tissue, even as the patient moves or palpitates the region. This may have the added benefit of preventing impingement of the nerve. Similarly, the variable thickness may enable smooth transitions and help conform the cuff to the surrounding anatomy.

Figure 11A:
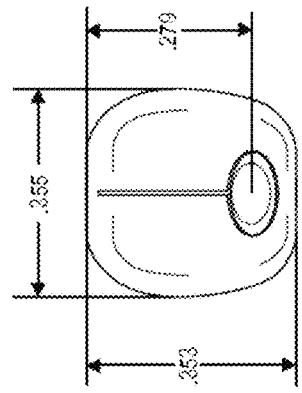
FIGS. 11A-11D illustrate another variation of a nerve cuff.
Figure 11B:
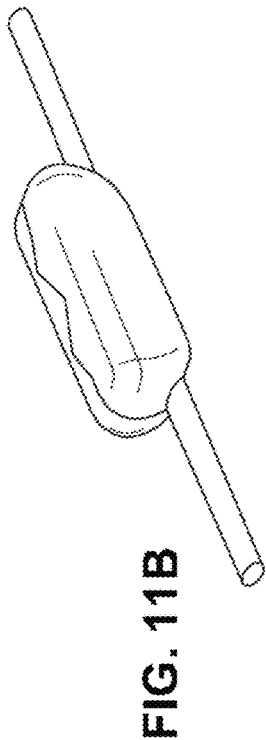
Figure 11C:
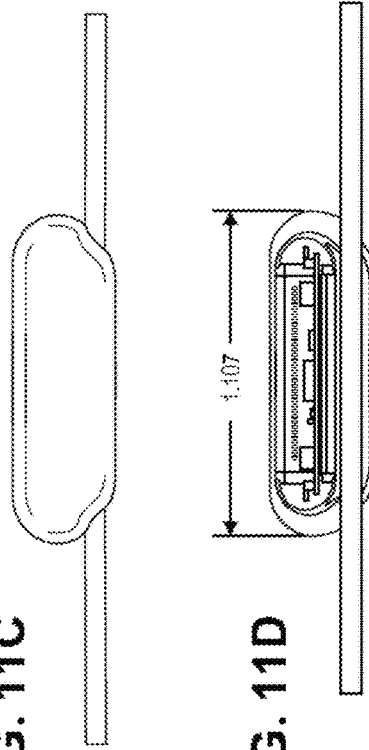

For Example, FIG. 11A shows an end view (with exemplary dimensions illustrated). It should be noted that in any of the figures or examples provided herein, the dimensions shown or described are for illustration only. In practice the dimensions may be +/− some percentage of the values shown (e.g., +/−5%, 10%, 15%, 20%, 25%, 30%, 40%, 50%, etc.). The section through the device shown in FIG. 11D illustrates the non-uniform thickness of the walls.

Both nerve cuff variations shown in FIGS. 10A-10D and FIGS. 11A-11D are substantially rounded or conforming, and have non-traumatic (or atraumatic) outer surfaces. As mentioned, this relatively smooth outer surface may enhance comfort and limit encapsulation of the nerve cuff within the tissue.

Figure 11D:
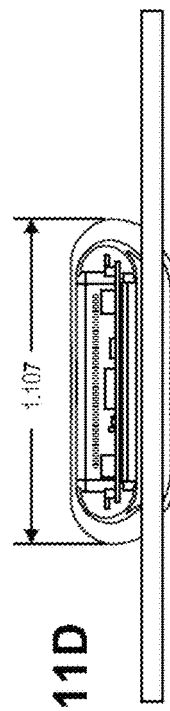
Figure 13B:
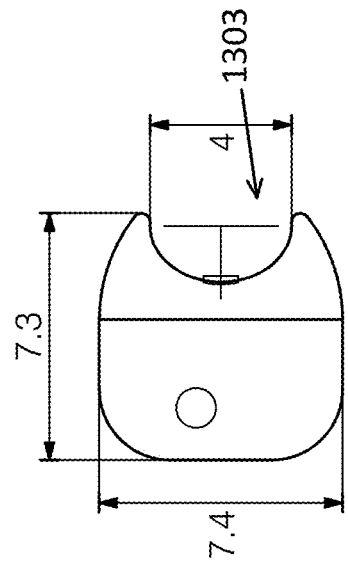
FIGS. 13B and 13C are end and bottom views, respectively, of the microstimulator shown in FIG. 13A.
Figure 13C:
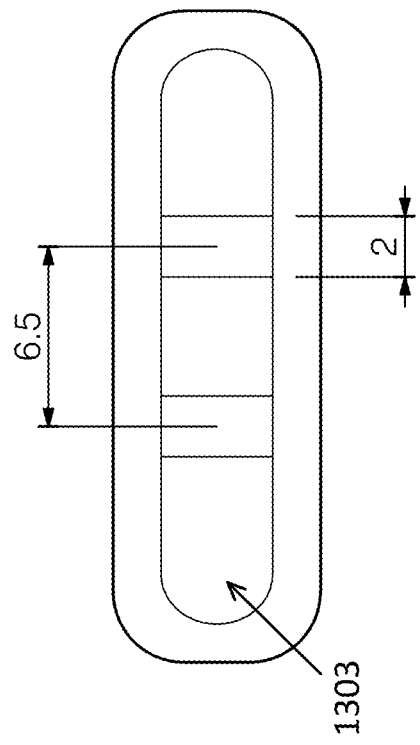
Figure 12:
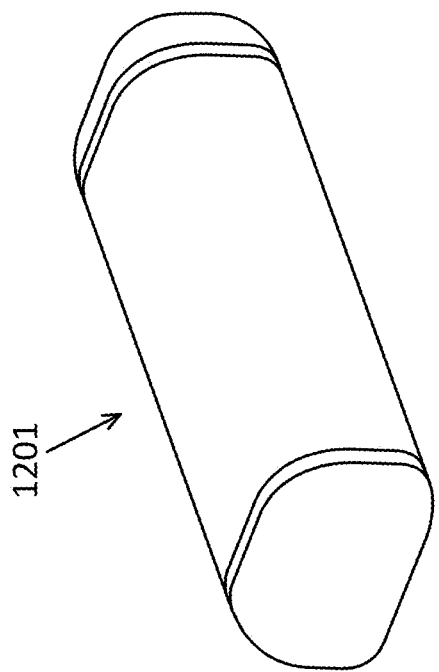
FIG. 12 shows one variation of a microstimulator that may be used in a nerve cuff as described herein.
Figure 13A:
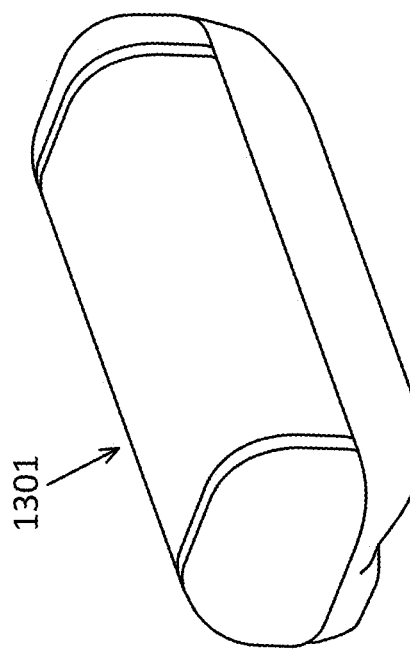
FIG. 13A shows a perspective view of another variation of a microstimulator.

As can be seen from FIGS. 10D and 11D, the microstimulator typically rests above (in the reference plane of the figure) the length of the nerve when inserted into the nerve cuff. In some variations, the microstimulator includes a contoured outer surface onto which one or more contacts (for contacting the nerve or an internal conductor within the nerve cuff) are positioned. For example, FIG. 12 illustrates one variation of a microstimulator 1201. In this example, the microstimulator includes one or more contacts on its outer surface with which to provide stimulation to a nerve. FIG. 13A shows another variation of a microstimulator 1301 in which the outer surface (the bottom in FIG. 13A) is curved to help form a channel surrounding the nerve when the microstimulator is inserted into the nerve cuff. FIG. 13B shows an end view, illustrating the channel concavity 1303 extending along the length of the microstimulator, and FIG. 13C shows a bottom view, looking down onto the channel region. In practice, the microstimulator shown may be placed within the nerve cuff and be held in position at least partially around the nerve. Thus, the microstimulator may help protect the nerve, which may lie within this channel. As mentioned above, and described in greater detail below, it is not necessary that the nerve lie against the contacts, as current may be conducted to the nerve from within the nerve cuff, which may be insulated sufficiently to prevent excessive leak or spillover of the current even when the cuff is oversized and only loosely surrounds the nerve. Furthermore, the nerve cuff may include one or more internal contacts allowing the current from the microstimulator to be distributed to the nerve via one or more internal contacts or leads, including circumferentially around the nerve.

Figure 14A:
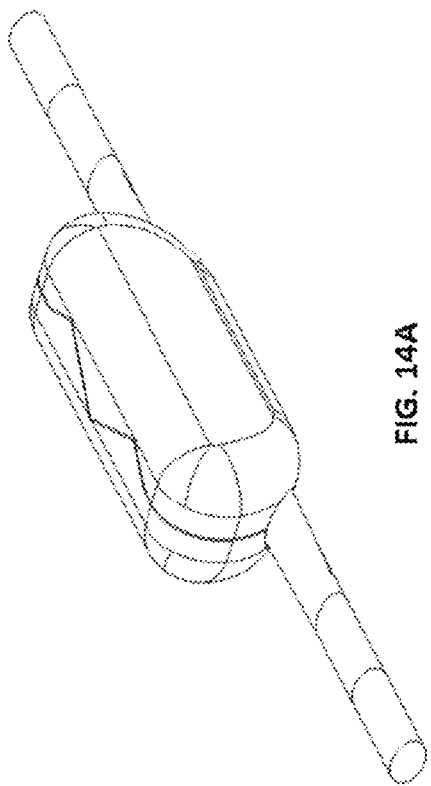
FIGS. 14A and 14B illustrate side and end views, respectively of another variation of a nerve cuff.
Figure 14B:
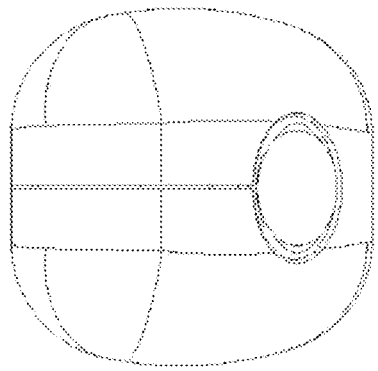
Figure 16:
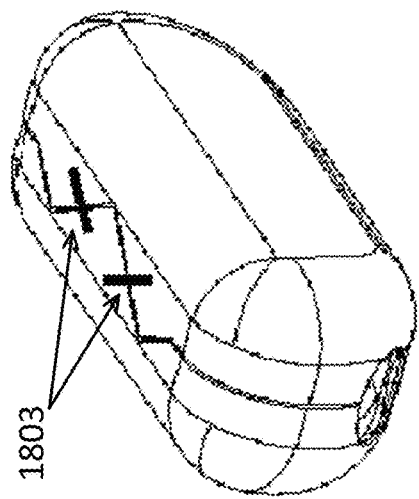
FIG. 16 is an internal end view of a microstimulator similar to the ones shown in FIGS. 14A-15D.

FIGS. 14A and 14B show another variation of a nerve cuff. In this example, the slit forming the opening is positioned on the upper surface (opposite to the nerve channel) along the length of the device. The slit is formed in an interlocking pattern. In FIG. 14A, the slit forms a zig-zag pattern, although other interlocking patterns may be used. For example, a sinusoidal or square-wave pattern may be used. The interlocking pattern may distribute the strain of closing the cuff around the nerve and microstimulator, and may make it easier to close the cuff once it has been positioned and the microstimulator has been inserted. FIG. 14B shows an end view of the same cuff shown in FIG. 14A.

Figure 15A:
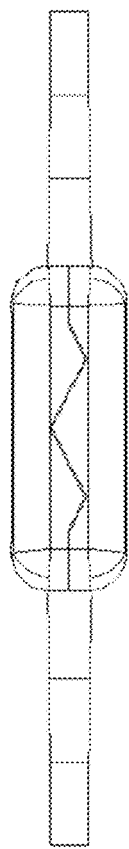
FIGS. 15A-15C show top, side and sectional views, respectively of a nerve cuff such as the one shown in FIG. 14A, attached to a nerve.
Figure 15B:
Figure 15C:
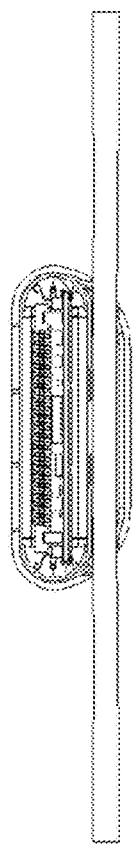
Figure 15D:
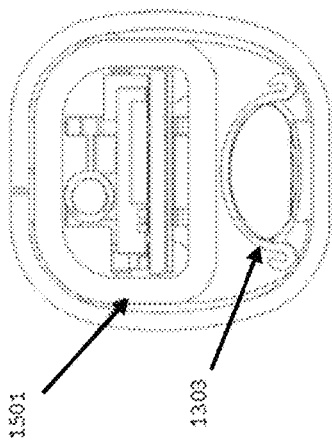
FIG. 15D is a section though the middle of a nerve cuff with a microstimulator secured there.

FIGS. 15A-15C show a similar cuff to the one shown in FIG. 14A from top and side views, connected to a nerve. In these example, the nerve extends through the internal channel and out the openings (which may be oval shaped, as shown in FIG. 14B) at either end. In FIG. 15C, a section through the length of the device shows that the microstimulator is positioned in the pouch (cavity) above the nerve. The microstimulator may be held in place by the walls of the cuff. A conforming microstimulator (such as the one shown in FIGS. 13A-13C) may be used, as illustrated in the cross-sectional view shown in FIG. 15D. The contacts 1503 of the conforming microstimulator are positioned on the bottom of the device.

Figure 17:
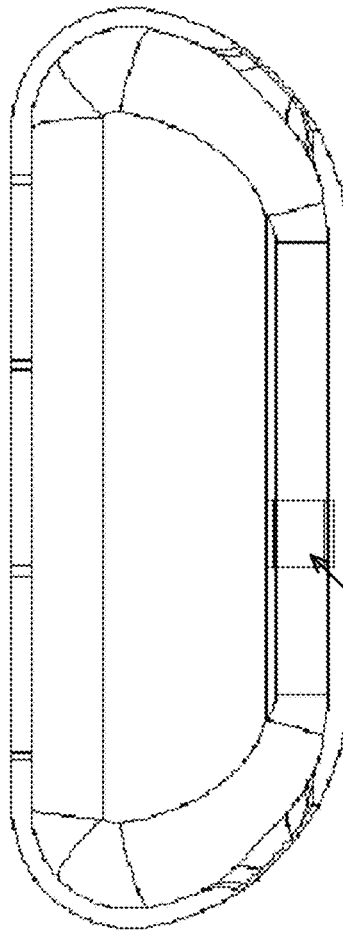
FIG. 17 is a sectional view showing the inside of another variation of a nerve cuff.

As mentioned briefly above, in some variations of the nerve cuff, the inner surface of the cuff body includes one or more internal contacts configured to couple with the microstimulator held within the pouch, and transmit any applied energy to the nerve (or receive energy from the nerve) positioned within the channel through the nerve cuff. The internal lead may be positioned so that it applies current to the underside (along the bottom region of the channel), or around the sides of the nerve as it sits within the channel. In some variations the internal conductor or lead is configured around the channel so that the nerve may be circumferentially stimulated, optimizing the applied stimulation. FIG. 17 is a long section though a nerve cuff, showing the inside of the cuff, and illustrates a variation of a nerve cuff having an internal lead 1703 that may apply stimulation to the underside of the nerve. This internal lead may be formed of any biocompatible conductive material, including medals, conductive plastics, or the likes. The internal lead may include exposed electrode surfaces 1703 for making contact with the nerve. Electrodes may be active contacts, also formed of any appropriate conductive material (e.g., metals, conductive polymers, braided materials, etc.). In some variations, the internal lead is coated or treated to help enhance the transfer of energy between the microstimulator and the nerve. Circumferential stimulation or conduction around the lead may reduce the impedances and assure uniform cross-sectional stimulation of the nerve bundle.

Figure 19:
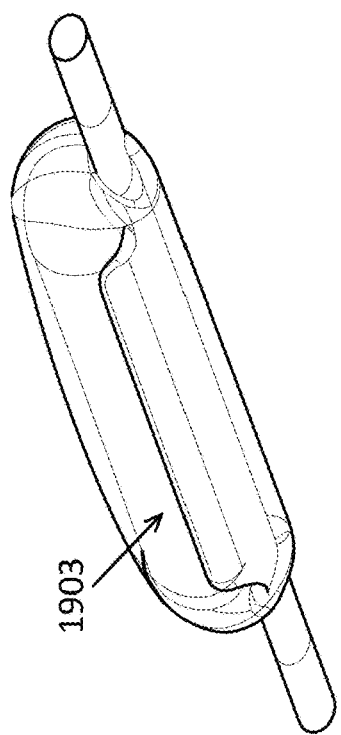
FIG. 19 is a side perspective view of a side-opening nerve cuff.

FIG. 19 shows another variation of a nerve cuff as described herein. In this example, the nerve cuff includes slit 1903 along one side of the device, adjacent to the nerve channel, which can be opened (e.g., by pulling apart the flaps or sides of the cuff) to expose nerve channel and the pocket for the microstimulator.

Figure 18:
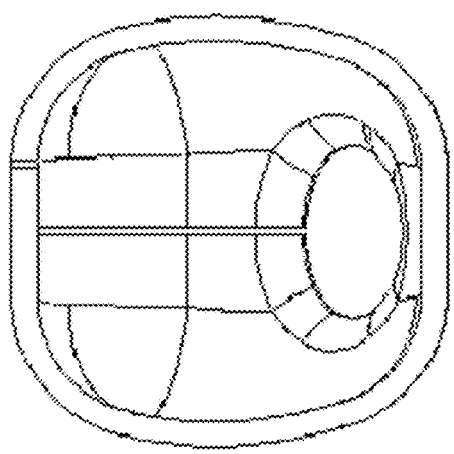
FIG. 18 is a side perspective view of the top-opening nerve cuff shown in FIG. 17.

Many of the nerve cuff variations described herein may be opened and positioned around the nerve, for example, by splitting them open along a slit or hinge region. The device may be configured so that they have sufficient resiliency to close themselves, or remain closed if the edges of the slit region are brought together. Thus, the device may have a shape memory property that encourages them to close. In some variations, as already mentioned, it may be useful to hold them closed, at least temporarily, once they have been positioned over a nerve and the microstimulator has been positioned within the pocket. Thus, the device may include one or more closure elements. For example, the device may include a suture hole or passage for suturing the device closed. In some variations the nerve cuff includes a button or other fastener element. In some variations, as illustrated in FIGS. 6 and 18, the device may be sutured close with a dissolvable suture. A few weeks or months after insertion, the nerve cuff may be encapsulated or engulfed by the surrounding tissue, and will be held closed by this encapsulation. Thus, the dissolvable sutures merely keep the cuff closed for initial anchoring before biointegration and encapsulation occurs.

Figure 21:
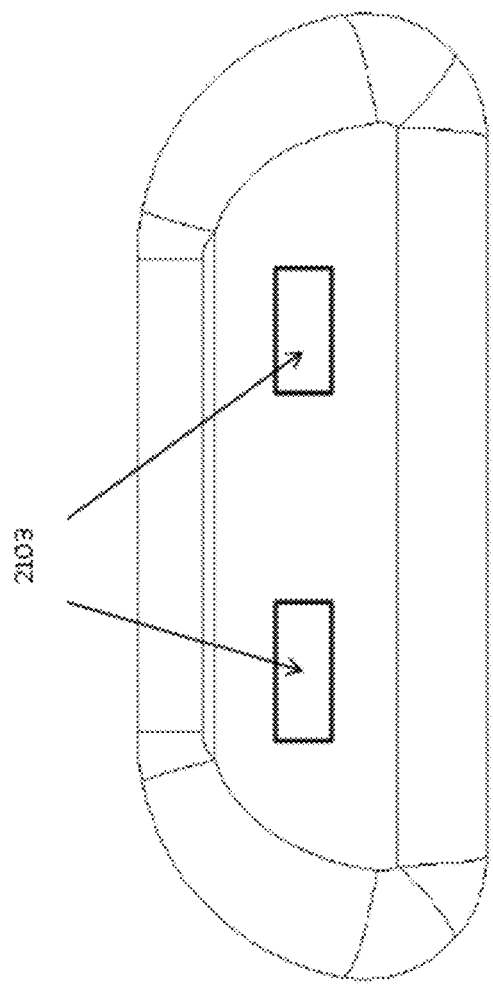
FIG. 21 is a side view of another variation of a nerve cuff.

Any of the nerve cuffs described herein may also include one or more external leads or contacts facing the outside of the nerve cuff body, which may be used to stimulate tissues outside of the nerve cuff, and not just the nerve within the channel through the cuff. FIG. 21 illustrates one variation of a nerve cuff having external leads. In this example, the nerve cuff includes two external contacts 2103 that are connected (through the wall of the nerve cuff body) to the microstimulator held within the nerve cuff pocket. Such external leads may be used for sensing in addition to (or instead of) stimulation. For example, these electrical contacts may be used to sense other physiological events such as muscle stimulation and/or cardiac function. These signals can be applied to aid synchronization of target nerve stimulation to minimize artifacts of target stimulation. Such signals may be too faint for reliable remote sensing, however the position of the microstimulator (insulated within the housing of the nerve cuff) may allow accurate and reliable sensing.

Figure 20:
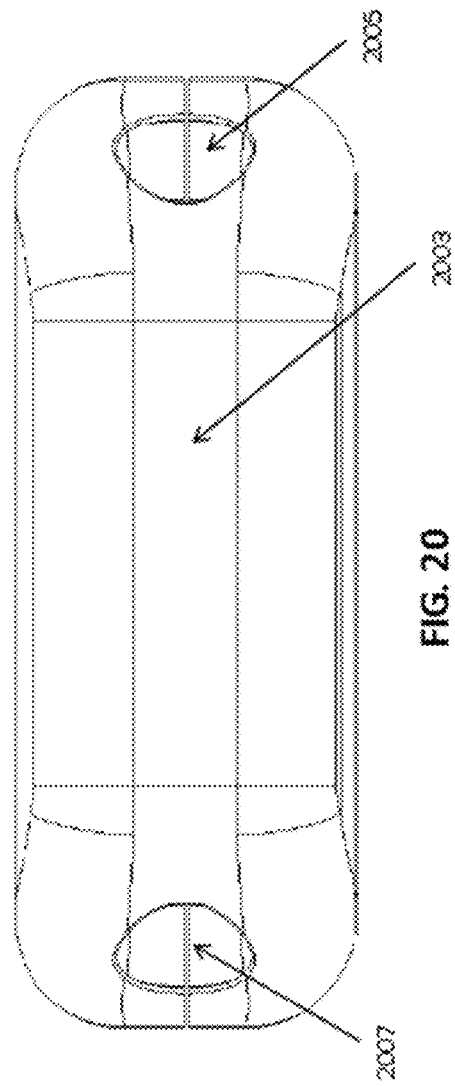
FIG. 20 is a transparent view of the bottom of a nerve cuff, showing the nerve channel.

A nerve may sit within a supported channel through the nerve cuff. As illustrated in FIG. 20, the channel 2003 may be formed having generally smooth sides, so as to prevent damage to the nerve and associated tissues. In some variations the nerve channel though the cuff is reinforced to prevent the cuff from pinching the device or from overtightening the device when closed over the nerve. Supports may be formed of a different material forming the nerve cuff body, or from thickened regions of the same material. Although multiple sizes of nerve cuff may be used (e.g., small, medium, large), in some variations, an oversized nerve cuff may be used, because the insulated cuff body will prevent leak of current from the microstimulator to surrounding tissues.

In general, the nerve cuff body may be electrically insulating, preventing leakage of charge from the microstimulator during operation. In some variations the nerve cuff includes shielding or insulation sufficient to electrically insulate the microstimulator within the nerve cuff body. Shielding material may particularly include electrically insulative materials, including polymeric insulators.

Figure 23:
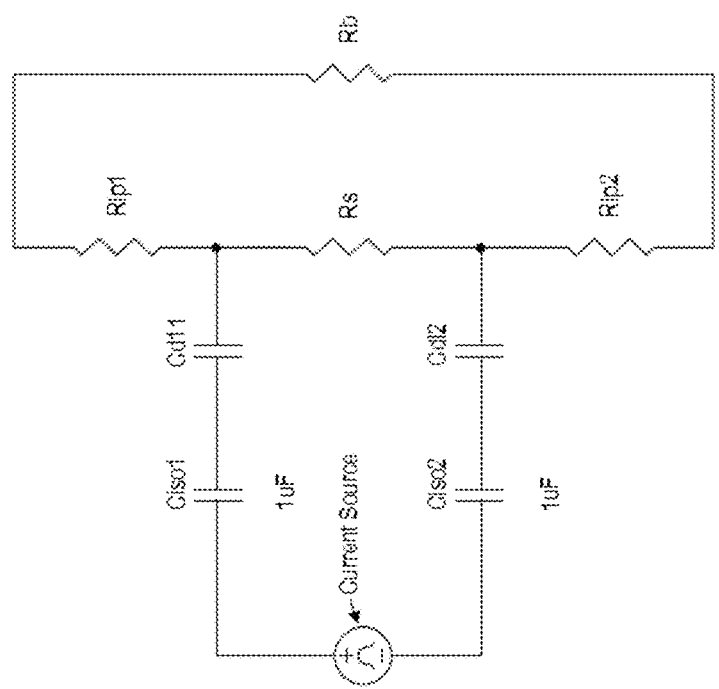
FIG. 23 shows an equivalent circuit modeling current loss when the nerve cuff is only loosely arranged over the nerve.

It may be shown mathematically using an equivalent circuit of the microstimulator, as shown in FIG. 23, that the current from a microstimulator is not appreciably passed out of even a loosely applied nerve cuff. This allows for the use of oversized nerve cuffs, rather than requiring rigorous sizing, or risking constricting the nerve.

For example, assuming a nerve with a cross section of $N_{area}$ is surrounded by a column of fluid $F_{area}$ enclosed by the nerve cuff, where contacts on the inside the microstimulator are spaced $E_{spacing}$ apart (center to center) and have a width $E_{width}$ and circle around the column of fluid and nerve $E_{degrees}$, it can be shown that the current will leak out the ends through a distance between the center of the electrode and the end of the nerve cuff that is defined by a distance $D_{guard}$.

The electrical model (illustrated in FIG. 23) consists of a current source that drives through DC isolation capacitors ($C_{iso2}$ optional), through the capacitance of each electrode ($C_{dl1}$ and $C_{dl2}$). From the electrodes, the current passes through either path $R_S$ or $R_{lp1}+R_b+R_{lp2}$. Whereas a portion of the current passing through $R_S$ provides useful work and the current passing through $R_{lp1}+R_b+R_{lp2}$ passes outside of the device and may cause undesirable effects.

If the nerve has a tight fit, then all the current passing through $R_S$ would contribute towards stimulation, but only a portion of the current can activate the nerve in the case of a loose fit. Based on this model, it can be shown that (assuming that the nerve and fluid columns form an ellipse defined by the major and minor axis a and b, and the pulse width is short and capacitances are large) just the real impedance and efficiency can be estimated.

The electrode surface area is determined to estimate the complex portion of the impedance:

$$F_{area} = \pi * a_F * b_F \text{ and } N_{area} = \pi * a_N * b_N.$$

Assuming the impedance of the cuff contained fluid and nerve has a similar conductance ρ and electrodes are spaced at $E_{spacing}$ then the real resistance of the conduction volume is: $R_{working}=E_{spacing}*\rho/F_{area}$, where the wasted resistance that should be maximized is calculated by:

$R_{wasted}=2*D_{guard}*\rho/F_{area}+R_{bulk}$, where $R_{bulk}$ is defined as the free field resistance between the two ends of the cuff.

So the efficiency (η) of the real current delivered in the POD is $R_{wasted}/(R_{working}+R_{wasted})$, and for the case of an undersized nerve assuming the conductivity of tissue and the fluid column is about equivalent then the stimulation efficiency is defined as $\eta_I=\eta*N_{area}/F_{area}$.

In operation, any of the devices described herein may be positioned around the nerve, and the microstimulator inserted into the nerve cuff, in any appropriate manner. FIGS. 22A-22H illustrate one variation of a method for applying the nerve cuff around a nerve and inserting a microstimulator. In this example, the patient is prepared for application of the nerve cuff around the cervical vagus nerve to hold a microstimulator device securely relative to the nerve (FIG. 22A). An incision is then made in the skin (≈3 cm) along Lange's crease between the Facial Vein and the Omohyoid muscle (FIG. 22B), and the Sternocleidomastoid is retracted away to gain access to the carotid sheath (FIG. 22C). The IJV is then reflected and ≤2 cm of the vagus is dissected from the carotid wall. As already discussed, this procedure may be modified or adapted for use specifically in the sub-diaphragmatic vagus nerve (e.g., the posterior sub-diaphragmatic vagus nerve).

In some variations, a sizing tool may be used to measure the vagus (e.g., diameter) to select an appropriate microstimulator and cuff (e.g., small, medium, large). In some variations of the method, as described above, an oversized cuff may be used. The nerve cuff is then placed under the nerve with the opening into the nerve cuff facing the surgeon (FIG. 22D), allowing access to the nerve and the pocket for holding the microstimulator. The microstimulator can then be inserted inside cuff (FIG. 22E) while assuring that the microstimulator contacts capture the vagus, or communicate with any internal contacts/leads. The nerve cuff may then be sutured shut (FIG. 22F). In some variations, the microstimulator may then be tested (FIG. 22G) to confirm that the device is working and coupled to the nerve. For example, a surgical tester device, covered in a sterile plastic cover, may be used to activate the microstimulator and perform system integrity and impedance checks, and shut the microstimulator off. If necessary the procedure may be repeated to correctly position and connect the microstimulator. Once this is completed and verified, the incision may be closed (FIG. 22H).

Systems for electrically stimulating one or more nerves to treat chronic inflammation may include an implantable, wireless microstimulator such as those described herein and an external charging device (which may be referred to as a charging wand, charger, or energizer). In some variations the system also includes a controller such as a "prescription pad" that helps control and regulate the dose delivered by the system. The microstimulator may be secured in position using a securing device (which may be referred to as a "POD") to hold the microstimulator in position around or adjacent to a nerve. These microstimulators are designed and adapted for treatment of chronic inflammation, and may be configured specifically for such use. Thus, an implantable microstimulator may be small, and adapted for the low duty-cycle stimulation to modulate inflammation. For example, the implantable microstimulator may hold a relatively small amount of power over weeks or even months and discharge it at a rate sufficient to modulate the anti-inflammatory pathway without significantly depressing heart rate or triggering any number of unwanted effects from the vagus nerve or other neural connections. Any of the nerves of the inflammatory reflex, including the vagus nerve, may be treated as described herein using the systems described.

For example, FIG. 24A illustrates one variation of a system for treating chronic inflammation that includes a microstimulator contained in POD that is mounted on cervical vagus nerve and charged a programmed by an external charger/programmer unit. This variation of a system includes a microstimulator 2403 that has been implanted to contact the vagus nerve as shown. The implant may be programmed, controlled and/or charged by a charger/controller 2405 device. In this variation the charger/controller is a loop with a wand region.

Figure 24B:
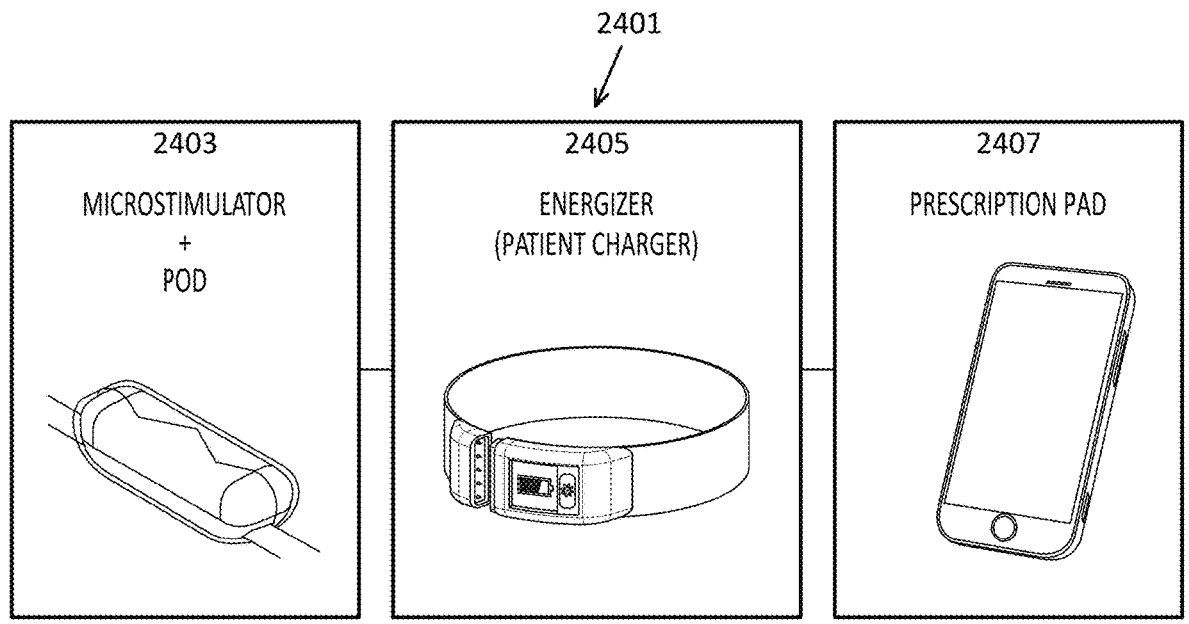
FIG. 24B shows another variation of a system for modulating chronic inflammation, including a microstimulator, charger ("energizer"), and system programmer/controller ("prescription pad").

FIG. 24B shows another variation of a system for treating chronic inflammation that also includes an implantable microstimulator 2403 (shown inserted into a POD to hold it in position relative to a nerve) and a charging device ("energizer" 2405) configured as a collar to be worn around the subject's neck and charge the implant. Optionally, the system may include a prescription pad 2407 which may be a separate dedicated device or part of a mobile or other handheld device (e.g., an application to run on a handheld device).

Figure 24C:
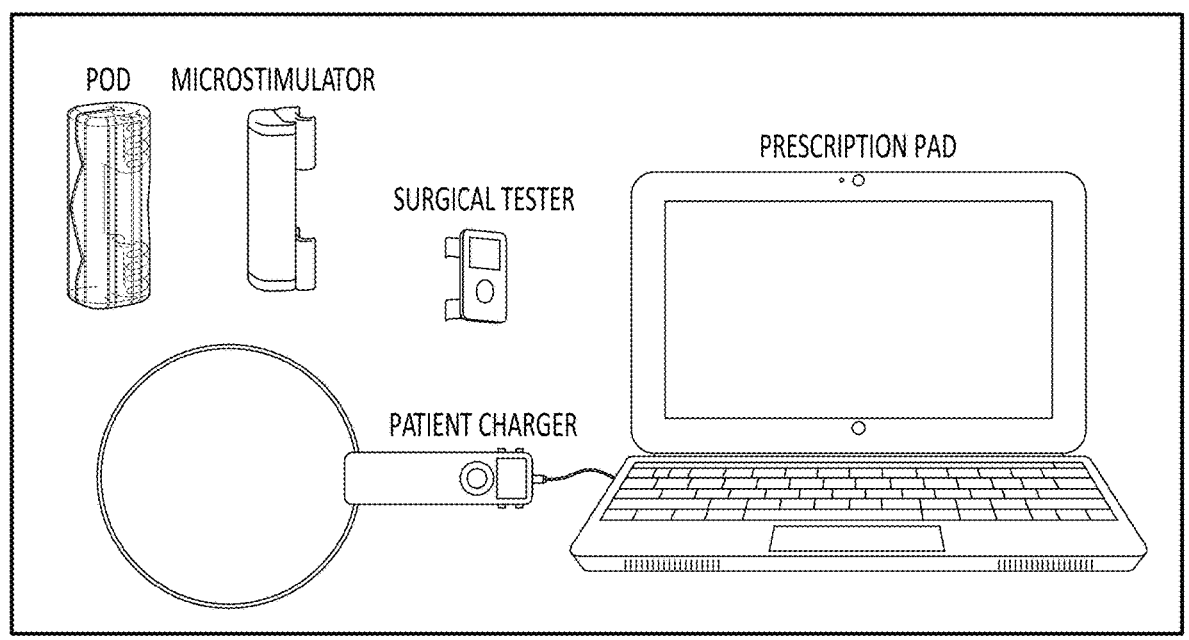
FIG. 24C shows another variations of a system for modulating chronic inflammation, including a microstimulator, a securing device (POD) for securing the leadless stimulator to the nerve, an external charger, a system programmer/controller ("prescription pad") and an optional surgical tester.

FIG. 24C shows another variation of a system for treating chronic inflammation. The systems described herein may also be referred to as systems for the neural stimulation of the cholinergic anti-inflammatory pathway (NCAP). These systems may be configured as chronic implantable systems. In some variations, the systems are configured to treat acutely (e.g., acute may 8 hours or less), sub-acutely (expected to occur for fewer than 30 days), or chronically (expected to occur for more than 30 days).

In general, the systems described herein may be configured to apply electrical stimulation at a minimum level necessary to modulate the inflammatory reflex (e.g., modulating cytokine release) characterized by the Chronaxie and rheobase. Chronaxie typically refers to the minimum time over which an electric current double the strength of the rheobase needs to be applied in order to stimulate the neuron. Rheobase is the minimal electrical current of infinite duration that results in an action potential. As used herein, cytokines refer to a category of signaling proteins and glycoproteins that, like hormones and neurotransmitters, are used extensively in cellular communication.

The NCAP Systems described herein are typically intended for the treatment of chronic inflammation through the use of implanted neural stimulation devices (microstimulators) to affect the Neural Stimulation of the Cholinergic Anti-inflammatory Pathway (NCAP) as a potential therapeutic intervention for rheumatologic and other inflammation-mediated diseases and disorders. Neurostimulation of the Cholinergic Anti-inflammatory Pathway (NCAP) has been shown to modulate inflammation. Thus, the treatment and management of symptoms manifested from the onset of disease (e.g., inflammatory disease) is based upon the concept of modulating the Cholinergic Anti-inflammatory Pathway. The NCAP pathway normally maintains precise restraint of the circulating immune cells. As used herein, the CAP is a reflex that utilizes cholinergic nerve signals traveling via the vagus nerve between the brain, chemoreceptors, and the reticuloendothelial system (e.g., spleen, liver). Local release of pro-inflammatory cytokines (e.g., tumor necrosis factor or TNF) from resident immune cells is inhibited by the efferent, or indirectly by afferent vagus nerve signals. NCAP causes important changes in the function and microenvironment of the spleen, liver and other reticuloendothelial organs. Leukocytes which circulate systemically become "educated" as they traverse the liver and spleen are thereby functionally down regulated by the affected environment of the reticuloendothelial system. This effect can potentially occur even in the absence of an inflammatory condition.

Under this model, remote inflammation is then dampened by down-regulated cytokine levels. Stimulation of the vagus nerve with a specific regiment of electrical pulses regulates production of pro-inflammatory cytokines. In-turn, the down regulation of these cytokines may reduce localized inflammation in joints and other organs of patients with autoimmune and inflammatory disorders.

The NCAP System includes a neurostimulator that may trigger the CAP by stimulating the cervical vagus nerve. The NCAP System issues a timed burst of current controlled pulses with sufficient amplitude to trigger the CAP at a particular interval. These two parameters, Dose Amplitude and Dose Interval, may be used by a clinician to adjust the device. For example, the clinician may set the Dose Amplitude by modifying the current level. The Dose Interval may be set by changing the duration between Doses (e.g. 12, 24, 48 hours).

In some variations, dose amplitude may be set to within the Therapy Window. The Therapy window is defined as the lower limit of current necessary to trigger the CAP, and the upper limit is the level at which the Patient feels uncomfortable. The lower limit is called the Threshold (T), and the uncomfortable level is called Upper Comfort Level (UCL).

Dose Amplitude thresholds are nonlinearly dependent upon Current (I), Pulse width (PW), Pulse Frequency (PF), and Burst Duration (BD). Amplitude is primarily set by charge (Q), that is Current (I)×Pulse width (PW). In neurostimulation applications current has the most linear relationship when determining thresholds and working within the therapy window. Therefore, the clinician may modify Dose Amplitude by modifying current. The other parameters are held to experimentally determined defaults. Pulse width is selected to be narrow enough to minimize muscle recruitment and wide enough to be well above the chronaxie of the targeted neurons. Stimulus duration and pulse frequency was determined experimentally in Preclinical work.

Dose Interval may be specific for particular diseases and the intensity of diseases experienced by a patient. Our initial research has indicated that the cervical portion of the vagus nerve may be an ideal anatomic location for delivery of stimulation. The nerve runs through the carotid sheath parallel to the internal jugular vein and carotid artery. At this location, excitation thresholds for the vagus are low, and the nerve is surgically accessible. We have not found any significant difference in biomarker modulation (e.g., modulation of cytokines) between right and left. Even though the right vagus is thought to have lower thresholds than the left in triggering cardiac dysrythmias, the thresholds necessary for NCAP are much lower than those expected to cause such dysrythmias. Therefore a device delivering NCAP can safely be applied to either the right or left vagus.

We have also found, surprisingly, that the Therapy Window is maximized on the cervical vagus through the use of a bipolar cuff electrode design. Key parameters of the cuff may be: spacing and shielding of the contacts. For example, the contact points or bands may be spaced 1-2 diameters of the vagus nerve apart, and it may be helpful to shield current from these contacts from other nearby structures susceptible to inadvertent triggering. The cuff may be further optimized by using bands which are as long and wide as possible to reduce neurostimulator power requirements.

Thus, any variations of the systems described herein (e.g., the NCAP system) may be implemented with a Cuff, Lead and Implantable Pulse Generation (IPG), or a Leadless Cuff. The preferred implementation is a leadless cuff implemented by a microstimulator with integral electrode contacts in intimate contact with the nerve and contained within a Protection and Orientation Device (POD). This is illustrated in FIGS. 26A and 26B. The POD 2601 may form a current shield, hold the microstimulator into place against the vagus nerve, and extend the microstimulator integral contacts with integral contacts in the POD itself. The POD is typically a polymer shell that encapsulates a microstimulator implant and that allows a nerve to run through the interior against the shell wall parallel to the length of the microstimulator implant. Within the shell of the POD, the microstimulator implant remains fixed against the vagus nerve so the electrodes remain in contact with the nerve. The POD anchors the implant in place and prevents the implant from rotating or separating from the nerve, as well as maintaining contact between the electrodes and the nerve and preserving the orientation as necessary for efficient external charging of the microstimulator battery.

Referring back to FIG. 24C, the system may include an implantable microstimulator contained in a POD, a Patient Charger, and a prescription pad that may be used by the clinician to set dosage parameters for the patient. This system may evaluate the efficacy, safety, and usability of an NCAP technology for chronic treatment of clinical patients. The system can employ a Prescription Pad (external controller) that may include the range of treatment options.

As described in more detail in Ser. No. 12/874,171, titled "PRESCRIPTION PAD FOR TREATMENT OF INFLAMMATORY DISORDERS", filed on Sep. 1, 2010, Publication No. US-2011-0054569-A1, previously incorporated by reference in its entirety, the Prescription Pad may incorporate workflows in a simplified interface and provide data collection facilities that can be transferred to an external database utilizing commercially robust and compliant methods and procedures. In use, the system may be recommended for use by a clinician after assessing a patient; the clinician may determine that treatment of chronic inflammation is warranted. The clinician may then refer the patient to an interventional doctor to implant the microstimulator. Thereafter then clinician (or another clinician) may monitor the patient and adjust the device via a wireless programmer (e.g. prescription pad). The clinician may be trained in the diagnosis and treatment procedures for autoimmune and inflammatory disorders; the interventional placement of the system may be performed by a surgeon trained in the implantation of active neurostimulation devices, with a sufficient depth of knowledge and experience regarding cervical and vagal anatomy, experienced in performing surgical dissections in and around the carotid sheath.

The system may output signals, including diagnostics, historical treatment schedules, or the like. The clinician may adjust the device during flares and/or during routine visits. Examples of implantation of the microstimulator were provided in Ser. No. 12/874,171, titled "PRESCRIPTION PAD FOR TREATMENT OF INFLAMMATORY DISORDERS", filed on Sep. 1, 2010, Publication No. US-2011-0054569-A1. For example, the implant may be inserted by making an incision in the skin (e.g., ~3 cm) along Lange's crease between the Facial Vein and the Omohyoid muscle, reflecting the Sternocleidomastoid and gaining access to the carotid sheath. The IJV may be displaced, and the vagus may be dissected from the carotid wall (≤2 cm). A sizing tool may be used to measure the vagus, and an appropriate Microstimulator and POD Kit (small, medium, large) may be selected. The POD may then be inserted under nerve with the POD opening facing the surgeon, so that the microstimulator can be inserted inside POD so that the microstimulator contacts capture the vagus. The POD may then be sutured shut. In some variations a Surgical Tester may be used to activate the microstimulator and perform system integrity and impedance checks, and shut the microstimulator off, during or after the implantation. In other variations the surgical tester may be unnecessary, as described in greater detail below.

A physician may use the Patient Charger to activate the microstimulator, perform integrity checks, and assure sufficient battery reserve exists. Electrodes may be conditioned with sub-threshold current and impedances may be measured. A Physician may charge the microstimulator. In some variations a separate charger (e.g., an "energizer") may be used by the patient directly, separate from the controller the physician may use. Alternatively, the patient controller may include controls for operation by a physician; the system may lock out non-physicians (e.g., those not having a key, code, or other security pass) from operating or modifying the controls.

In general, a physician may establish safe dosage levels. The physician may slowly increment current level to establish a maximum limit (Upper Comfort Limit). This current level may be used to set the Dosage Level. The exact procedure may be determined during this clinical phase.

The Physician may also specify dosing parameters that specify dosage levels and dosage intervals. The device may contain several concurrent dosing programs which may be used to acclimate the patient to stimulus, gradually increase dosage until efficacy is achieved, reset tachyphylaxis, or deal with unique patient situations.

In some variations, the Prescription Pad may be configured to handle multiple patients and may index their data by the microstimulator Serial Number. For example, a Prescription Pad may handle up to 100,000 patients and 10,000 records per patient, and may store the data in its local memory and may be backed up on an external database. In some variations, during each charging session, accumulated even log contents will be uploaded to the Patient Charger for later transfer to Prescription Pad. The data may or may not be cleared from the microstimulator. For example, FIG. 25 shows the addition of a prescription pad 203 wirelessly connected to the charger/programmer 207.

The microstimulators described herein are configured for implantation and stimulation of the cholinergic anti-inflammatory pathway, and especially the vagus nerve. In particular the microstimulators described herein are configured for implantation in the cervical region of the vagus nerve to provide extremely low duty-cycle stimulation sufficient to modulate inflammation. These microstimulators may be adapted for this purpose by including one or more of the following characteristics, which are described in greater detail herein: the conductive capsule ends of the microstimulator may be routed to separate electrodes; the conductive capsule ends may be made from resistive titanium alloy to reduce magnetic field absorption; the electrodes may be positioned in a polymer saddle; the device includes a suspension (e.g., components may be suspended by metal clips) to safeguard the electronics from mechanical forces and shock; the device may include an H-bridge current source with capacitor isolation on both leads; the device may include a built in temperature sensor that stops energy absorption from any RF source by detuning the resonator; the device may include a built-in overvoltage sensor to stop energy absorption from any RF source by detuning resonator; the system may include DACs that are used to calibrate silicon for battery charging and protection; the system may include DACs that are used to calibrate silicon for precision timing rather than relying on crystal oscillator; the system may include a load stabilizer that maintains constant load so that inductive system can communicate efficiently; the system may include current limiters to prevent a current rush so that the microstimulator will power up smoothly from resonator power source; the system may extract a clock from carrier OR from internal clock; the device may use an ultra-low power accurate RC oscillator that uses stable temperature in body, DAC calibration, and clock adjustment during charging process; the device may use a solid state LIPON battery that allows fast recharge, supports many cycles, cannot explode, and is easy to charge with constant voltage; and the device may include a resonator that uses low frequency material designed not to absorb energy by high frequency sources such as MRI and Diathermy devices.

Many of these improvements permit the device to have an extremely small footprint and power consumption, while still effectively modulating the vagus nerve.

FIG. 26A is a perspective drawing of the Pod containing the microstimulator. Sutures (not shown) are intended to be bridged across one to three sets of holes. Electrodes integrated into the pod are not shown but would extend as bands originating and ending on the two outer pairs of suture holes.

Figure 26E:
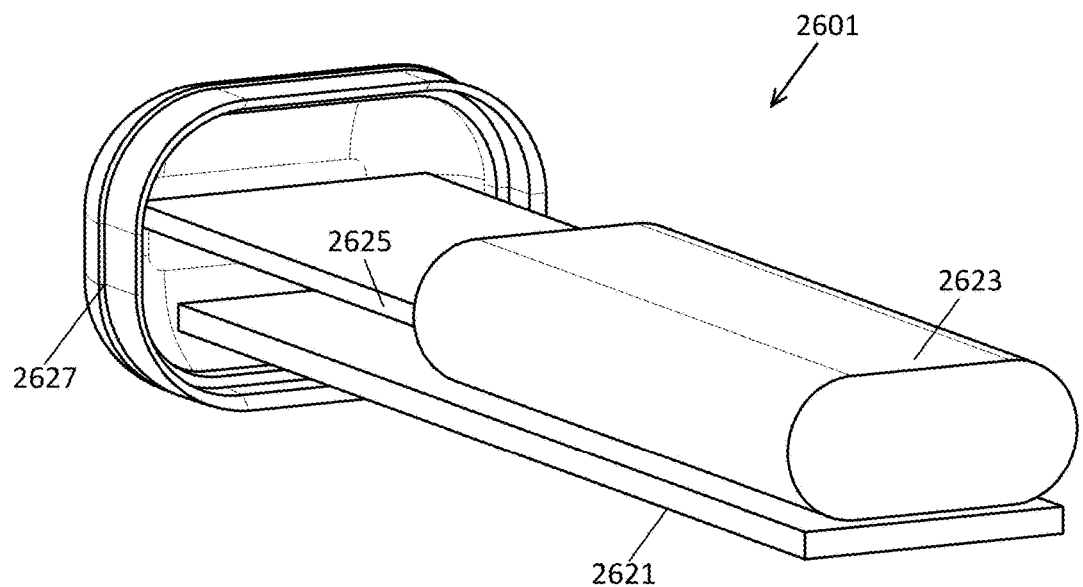
FIG. 26E shows another variation of the microstimulator.
Figure 26F:
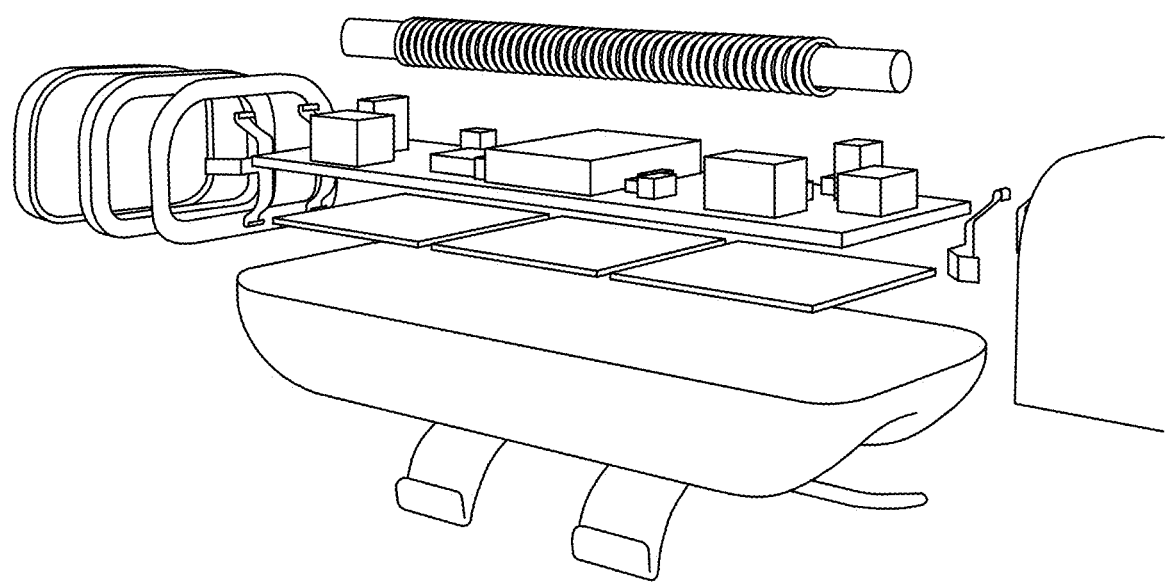
FIG. 26F illustrates another variation of a microstimulator as described herein.

In some variations, including those described above, the microstimulator consists of a ceramic body with hermetically sealed titanium-niobium ends and integral platinum-iridium electrodes attached. The microstimulator may be designed to fit within a POD 2609, as shown in FIGS. 26A-26D. As described above, the POD is a biocompatible polymer with integrated electrodes that may help the microstimulator to function as a leadless cuff electrode. In some variations, such as the variation shown in FIG. 26E, contained within the hermetic space of the microstimulator 2601 is an electronic assembly that contains a rechargeable battery 2621, solenoid antenna 2623, hybrid circuit 2625 and electrode contacts (Ti Alloy braze ring and end cap) 2627 at each end to make contact with the titanium/platinum case ends.

As mentioned above, some of the device variations described herein may be used with a POD to secure the implant (e.g., the leadless/wireless microstimulator implant) in position within the cervical region of the vagus nerve so that the device may be programmed and recharged by the charger/programmer (e.g., "energizer"). For example, FIG. 28 shows a schematic diagram of a POD containing a microstimulator. The cross section in FIG. 4 shows the ceramic tube containing electronic assembly that includes the hybrid, battery and coil. The rigid or semi-rigid contacts are mounted on the tube and surround the oval vagus nerve. The POD surrounds the entire device and includes a metal conductor that makes electrical contact with the microstimulator contacts and electrically surrounds the nerve.

Microstimulator Parameters

In some variations, the microstimulator may have a bipolar stimulation current source that produce as stimulation dose with the characteristics shown in table 1, below. In some variation, the system may be configured to allow adjustment of the "Advanced Parameters" listed below; in some variations the parameters may be configured so that they are predetermined or pre-set. In some variations, the Advanced Parameters are not adjustable (or shown) to the clinician. All parameters listed in Table 1 are ±5% unless specified otherwise.

TABLE 1

Microstimulator parameters

| Property | Value | Default |
|---|---|---|
| Dosage Amplitude (DA) | 0-5,000 µA in 25 µA steps (or high intensity simulation, between 0.1 mA and 20 mA, e.g., between 1 mA and 15 mA, between 2 mA and 10 mA) | 0 |
| Intervals | Minute, Hour, Day, Week, Month | Day |
| Number of Doses per Interval | N = 60 Maximum | 1 |
| Advanced Parameters | | |
| Pulse width Range (PW) | 100-1,000 µS in 50 µS increments | 200 |
| Stimulus Duration (SD) | 0.5-1000 seconds per dose | 60 |
| Pulse Frequency (PF) | 1-50 Hz | 10 |
| Stimulus Voltage (SV) | ±3.3 or ±5.5 ±1 Volts high stimulation: between 6 and 20 Volts | Automatically set by software |
| Constant Current Output | ±15% over supported range of load impedances (200-2000Ω) | |
| Specific Dose Time | Set a specific time between 12:00 am-12:00 am in one minute increments for each Dose Issue | Driven by default table (TBD) |
| Number of Sequential Dosing Programs | 4 maximum | 1 |

The Dosage Interval is defined as the time between Stimulation Doses. In some variations, to support more advanced dosing scenarios, up to four 'programs' can run sequentially. Each program has a start date and time and will run until the next program starts. Dosing may be suspended while the Prescription Pad is in Programming Mode. Dosing may typically continue as normal while charging. Programs may be loaded into one of four available slots and can be tested before they start running. Low, Typical, and High Dose schedules may be provided. A continuous application schedule may be available by charging every day, or at some other predetermined charging interval. For example, Table 2 illustrates exemplary properties for low, typical and high dose charging intervals:

TABLE 2 low typical and high dose charging intervals

| Property | Value |
|---|---|
| Low Dose Days Charge Interval | 30 days max: 250 µA, 200 µS, 60 s, 24 hr., 10 Hz, ±3.3 V |
| Typical Dose Charge Interval | 30 days max: 1,000 µA, 200 µS, 120 s, 24 hr., 10 Hz, ±3.3 V |
| High Dose Charge Interval | 3.5 days max: 5,000 µA, 500 µS, 240 s, 24 hr., 20 Hz, ±5.5 V, |

The system may also be configured to limit the leakage and maximum and minimum charge densities, to protect the patient, as shown in Table 3:

TABLE 3 safety parameters

| Property | Value |
|---|---|
| Hardware DC Leakage Protection | <50 nA |

TABLE 3-continued safety parameters

| Property | Value |
| --- | --- |
| Maximum Charge Density | 30 µC/cm²/phase |
| Maximum Current Density | 30 mA/cm² |

In some variations, the system may also be configured to allow the following functions (listed in Table 4, below):

TABLE 4

Additional functions of the microstimulator and/or controller(s)

| Function | Details |
| --- | --- |
| Charging | Replenish Battery |
| Battery Check | Determine charge level |
| System Check | Self-Diagnostics |
| Relative Temperature | Temperature difference from baseline |
| Program Management | Read/Write/Modify a dosage parameter programs |
| Program Up/Download | Transfer entire dosage parameter programs |
| Electrode Impedances | Bipolar Impedance (Complex) |
| Signal Strength | Strength of the charging signal to assist the patient in aligning the external Charge to the implanted Microstimulator. |
| Patient Parameters | Patient Information |
| Patient History | Limited programming and exception data |
| Implant Time/Zone | GMT + Time zone, 1 minute resolution, updated by Charger each charge session |
| Firmware Reload | Boot loader allows complete firmware reload |
| Emergency Stop | Disable dosing programs and complete power down system until Prescription Pad connected |

In some embodiments, a modified nerve cuff and electrode can be secured around the sub-diaphragmatic vagus nerve and the electrical stimulation can be delivered to the vagus nerve. For example, when using the nerve cuffs described herein, the slit on the nerve cuff can be opened to allow access to a channel for receiving the nerve. The nerve can be placed within the channel, and the slit can then be closed to secure the nerve within the channel of the nerve cuff.

A nerve cuff can include an electrode for sensing electrical signals, such as action potentials, to measure nerve activity of the nerve attached to the nerve cuff. Alternatively or additionally, as described above, remote sensors can be placed away from the nerve cuff at remote locations to sense electrical activity in nerves or nerve locations described herein. In some embodiments, the remote locations may be closer to the source of pain, such as near or at the extremities and joints.

Microstimulator Configurations

In order to improve the efficiency of power transfer from the charger to the microstimulator, various modifications can be made to the microstimulator. For example, the size of the receiving antenna within the microstimulator can be increased without increasing the size, and particularly the diameter, of the microstimulator. As described above, the receiving antenna can be made of a receiving coil that is wrapped around a magnetic core, as shown in FIGS. 26F and 27A-27D. One way of increasing the power transfer efficiency is to increase the diameter of the coil and/or the magnetic core.

Figure 29:
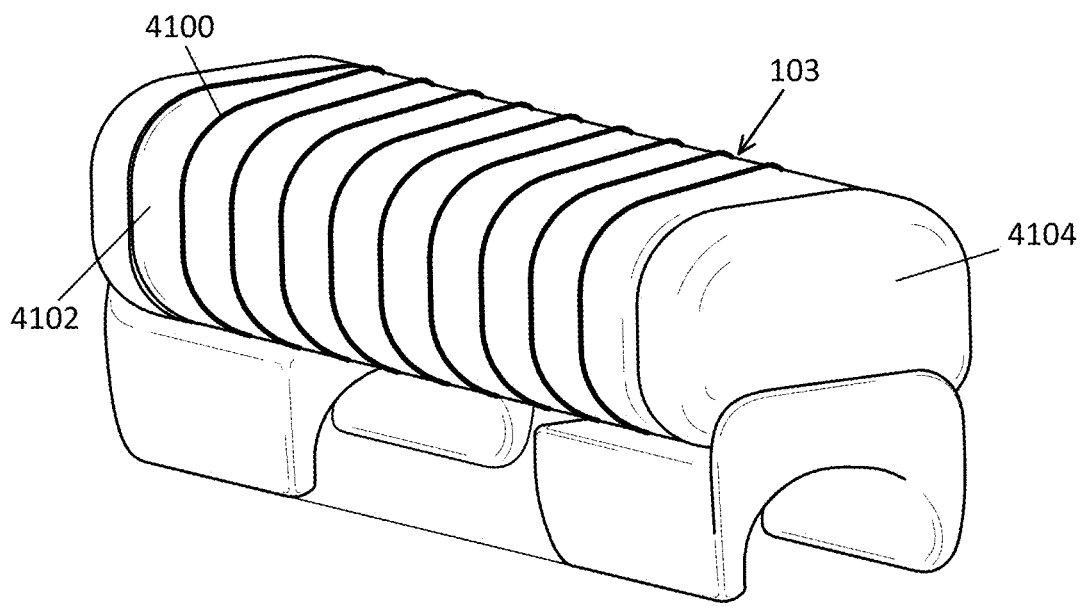
FIG. 29 shows a microstimulator with a housing made of a high magnetic permeability material and a coil wrapped around the housing.

For example, in some embodiments, the receiving coil and magnetic core of the antenna can be incorporated into the housing of the microstimulator 103, as illustrated in FIG. 29. In some embodiments, the coil 4100 can be wrapped around a housing 4102 made of a high magnetic permeability material, such as a ferrite or Mu-metal. The end caps 4104 can also be made of a high magnetic permeability material. By making the housing 4102 and end caps 4104 out of a high magnetic permeability material, the housing 4102 and end caps 4104 can function as a large magnetic core for the coil 4100. To protect the coil on the housing, the coil may be covered with a coating or sheath. In some embodiments, the protective coating or sheath can also be made of a high magnetic permeability material.

Examples of high magnetic permeability materials include ferrites, ferrite polymer composites, ferrite filled polymers, ferrite loaded rubber, and a ferrite tape. Other relatively high magnetic permeability materials that may be used include Mu-metal, iron, steel, and various metal alloys. In some embodiments, the high magnetic permeability materials have a relatively high intrinsic magnetic permeability that is greater than 10, 100, 1000, 10,000, or 100,000 times the magnetic permeability of a vacuum.

Figure 30:
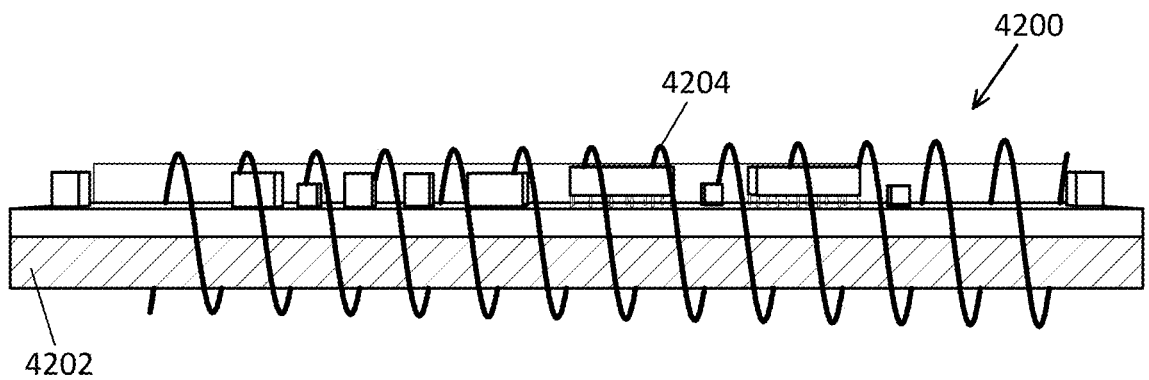
FIG. 30 illustrates a PCB with a high magnetic permeability material integrated and a coil wrapped around the PCB.

In some embodiments, as illustrated in FIG. 30, the printed circuit board (PCB) 4200 can be made of, or be made in part of, or incorporate a high magnetic permeability material 4202, and the coil 4204 can be wrapped around the PCB 4200. For example, a high magnetic permeability rod or plate can be added to or integrated with the PCB. In some embodiments, the high magnetic permeability material can extend to and be in contact with the end caps, which can also be made of a high magnetic permeability material. In particular, the high magnetic permeability material of the core may extend to and be in contact with the end caps when the end caps are made of a high permeability material. In some variations, if the end caps are metallic but not high-permeability, the core may stop short of the end caps to limit their shielding effect.

Figure 31:
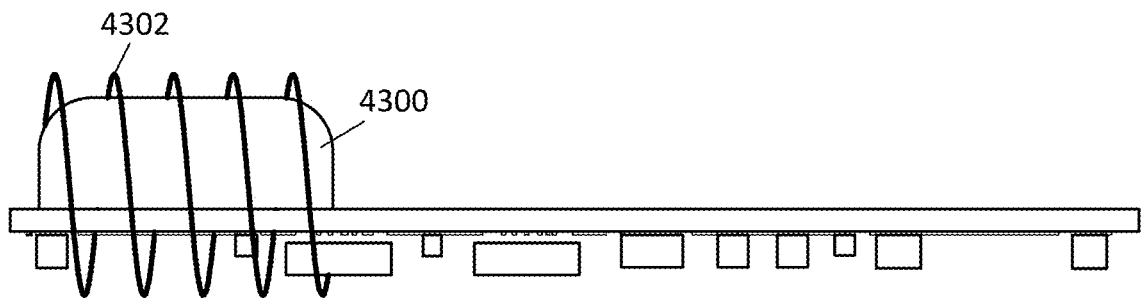
FIG. 31 illustrates a battery encased with a high magnetic permeability material and wrapped with a coil.

In other embodiments, as shown in FIG. 31, the battery 4300 can be formed of or encased in a high magnetic permeability material, and the coil 4302 can be wrapped around the battery 4300.

Figure 32A:
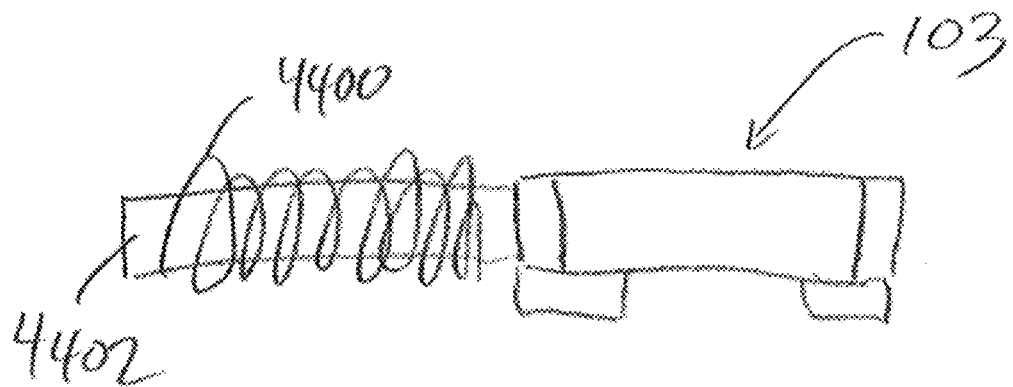
FIGS. 32A and 32B illustrate a magnetic core and coil antenna that is located outside the microstimulator.
Figure 32B:
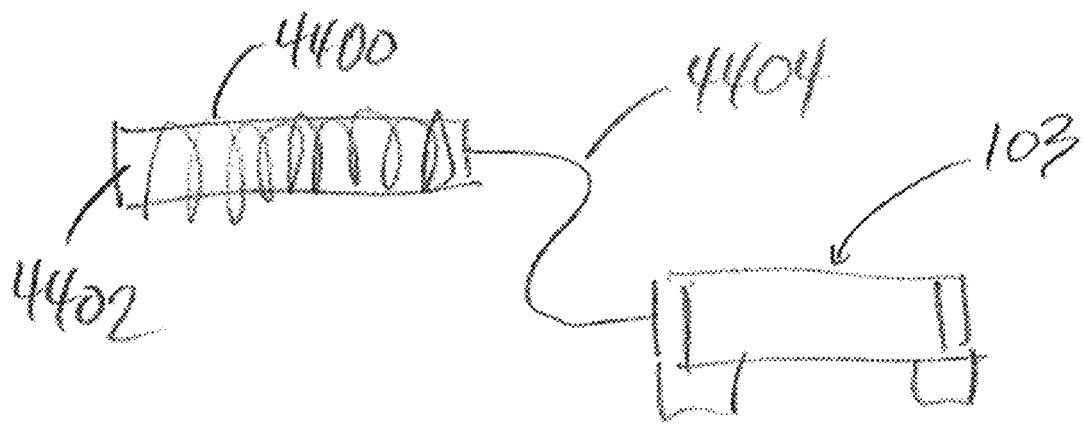

In some embodiments, as shown in FIGS. 32A and 32B, the coil 4400 and magnetic core 4402 can be located outside the housing of the microstimulator 103. For example, the magnetic core 4402 can be a cylinder made of a high magnetic permeability material with a coil 4400 wrapped around it. As shown FIG. 32A, in some embodiments, the magnetic core 4402 can be attached to one end of the housing of the microstimulator 103 such that the magnetic core 4402 and microstimulator 103 lie end to end along the same axis. As shown in FIG. 32B, in some embodiments, the magnetic core 4402 and wrapped coil 4400 can be separate from the microstimulator 103 and instead be electrically connected together using a wire 4404. Separating the magnetic core and coil from the rest of the microstimulator allows the antenna to be placed closer to the skin or under the skin and may make charging easier and more efficient. This can be particularly useful when the implant is embedded deep within the patient, such as implantation within the torso, which can make inductive charging more challenging.

In some embodiments, the magnetic core has approximately the same diameter as the microstimulator. In other embodiments, the magnetic core can have a cross-section that is smaller than the cross-section of the microstimulator, such as about ¼, ⅓, ½, or ¾ the diameter of the microstimulator. In other embodiments, the magnetic core can have a cross-section that is larger than the diameter of the microstimulator, such as about 1.5, 2, 2.5, or 3 times the diameter of the microstimulator. In some embodiments, the magnetic core can have a cross-section that is similar in size and shape with the cross-section of the microstimulator.

In any of the embodiments disclosed herein, the high magnetic permeability material can have one or more slits to reduce eddy currents. In particular, if a conductive material is used for the high magnetic permeability material. Ferrite is an insulator, however if a conductive material (e.g. mu-metal, steel, amorphous/nanocrystalline magnetic alloy) is used, eddy currents can be reduced by breaking the current path, including introducing a gap or space. Depending on the geometry, this may be achieved by cutting slits, laminating thin layers of material, or using a powdered material in an insulating binder.

Charger

In some embodiments, the magnetic properties of the charger, and in particular, the housing surrounding the charger, may be modified to shape the field emitted by the charger for inductively charging the implant. In general, charging of the implant (e.g., inductively charging) may depend in part on the orientation and positon of the implant relative to the charging field. The methods and apparatuses described herein may improve the relationship between the inductive field and the implant. For example, the charger, which may be a wearable charger such a collar, necklace, or the like, or it may be hand-held charger, may be configured (and/or the charging portion of the implant may be configured) to raise the inductance and thus the quality factor (Q), potentially providing a greater power transfer between the applied charging field and the implant.

For example, the charger housing may include a material having a high magnetic field permeability, such as a ferromagnetic ceramic material (ferrite), ferrite-filled polymer, ferrite-embedded polymer, alloys of iron and nickel (e.g., commercially sold as Mumetal and Permalloy) and the like. These high-magnetic-permeability materials may concentrate and direct the magnetic field up from the charger (when worn on the neck, for example) towards the implant, and may help target the field in the neck and for reception by the implanted microcontroller.

For example, the microcontroller may be implanted so that it is generally oriented up and to the right, as shown in FIG. 24B. Thus, a charger (configured as a wearable collar) may be configured by the use of a high-magnetic field permeability material to direct the field up from the charger (e.g., collar) toward the implant. The higher (denser) field may also be shifted the right (patient's right) as well.

By steering the field, e.g., up from the collar, the collar may be more comfortably worn around the base of the person's neck. This reduces the importance of placing the charger closer (e.g., directly over and/or adjacent to) the implant, which may be located up to several inches above the base of the neck, as show on in FIG. 24B. Further, the orientation of the field may be adapted using the high magnetic permeability material so that it is oriented appropriately to charge the implant.

Figure 33B:
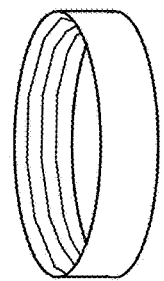
FIGS. 33A and 33B illustrate the magnetic field generated by an embodiment of a collar type charger without the addition of a high magnetic permeability material.
Figure 34B:
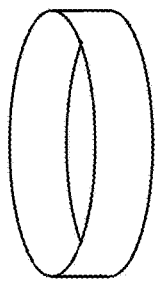
FIGS. 34A and 34B illustrate the magnetic field generated by an embodiment of a collar type charger with the addition of a high magnetic permeability material.
Figure 33A:
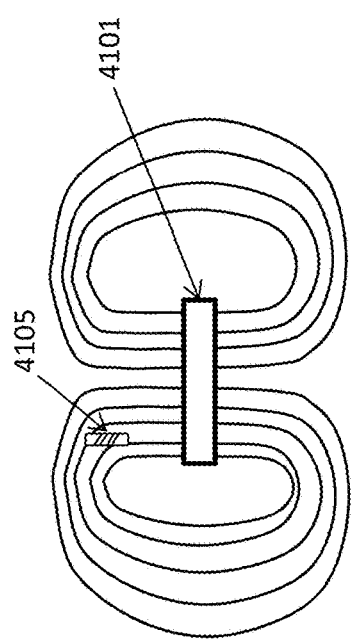
Figure 34A:
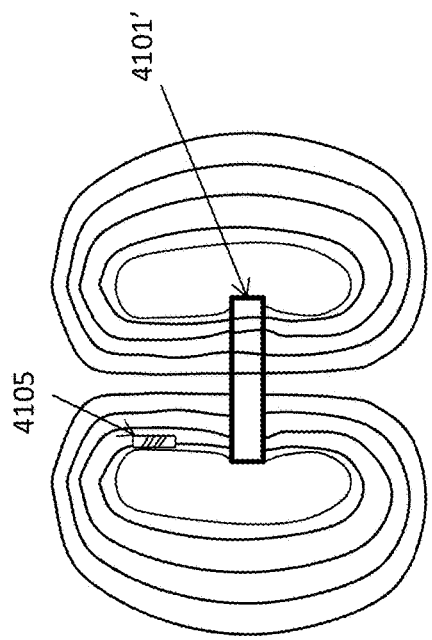

In some variations, a high magnetic permeability material is included around the transmitting coil of the charger to concentrate and shape or direct the magnetic field through the transmitting coil and towards the receiving coil in the neurostimulator. FIGS. 33A and 33B illustrate a magnetic field generated by a charger 4101 without the additional a high magnetic permeability material. An exemplary implant 4105 is shown up (above) and to one side of the charger. FIGS. 34A and 34B illustrate the magnetic field generated by a charger with the high magnetic permeability material added and arranged to concentrate and direct the magnetic field towards the neurostimulator. As mentioned, by concentrating the magnetic field (and/or orienting it) through the receiving coil of the implanted neurostimulator by using the high magnetic permeability material, the inductance, and therefore Q-factor of the coil can be raised, and therefore a higher power transfer rate can be achieved increasing energy transfer efficiency.

Examples of high magnetic permeability materials include ferrites, ferrite polymer composites, ferrite filled polymers, ferrite loaded rubber, and a ferrite tape. Other high magnetic permeability materials that may be used include Mu-metal, iron, steel, and various metal alloys. In some embodiments, the high magnetic permeability materials have a relatively magnetic permeability that is greater than 10, 100, 1000, 10,000 or 100,000 times the magnetic permeability of a vacuum.

In some embodiments as described above, the charger can include a transmitting coil that is worn around the neck in order to charge a neurostimulator that is positioned on the cervical portion of the vagus nerve. If the patient is sitting or standing during the charging process, the charger may end up resting on the lower portion of the neck while the neurostimulator is implanted in a higher portion of the neck. The transmitting coil in the charger can generate an electromagnetic field with field lines that run through the loop. A high magnetic permeability material can be added around the transmitting coil to concentrate and direct the field lines towards the neurostimulator. For example, the high magnetic permeability material can be added to the upper inner surface of covering around the transmitting coil in order to concentrate and direct the field lines upwards and inwards towards a neurostimulator located in the neck and above transmitting coil. In other embodiments, the high magnetic permeability material can be added just to the inner surface of the covering that faces the skin, or the high magnetic permeability material can be incorporated into the entire covering.

Figure 37A:
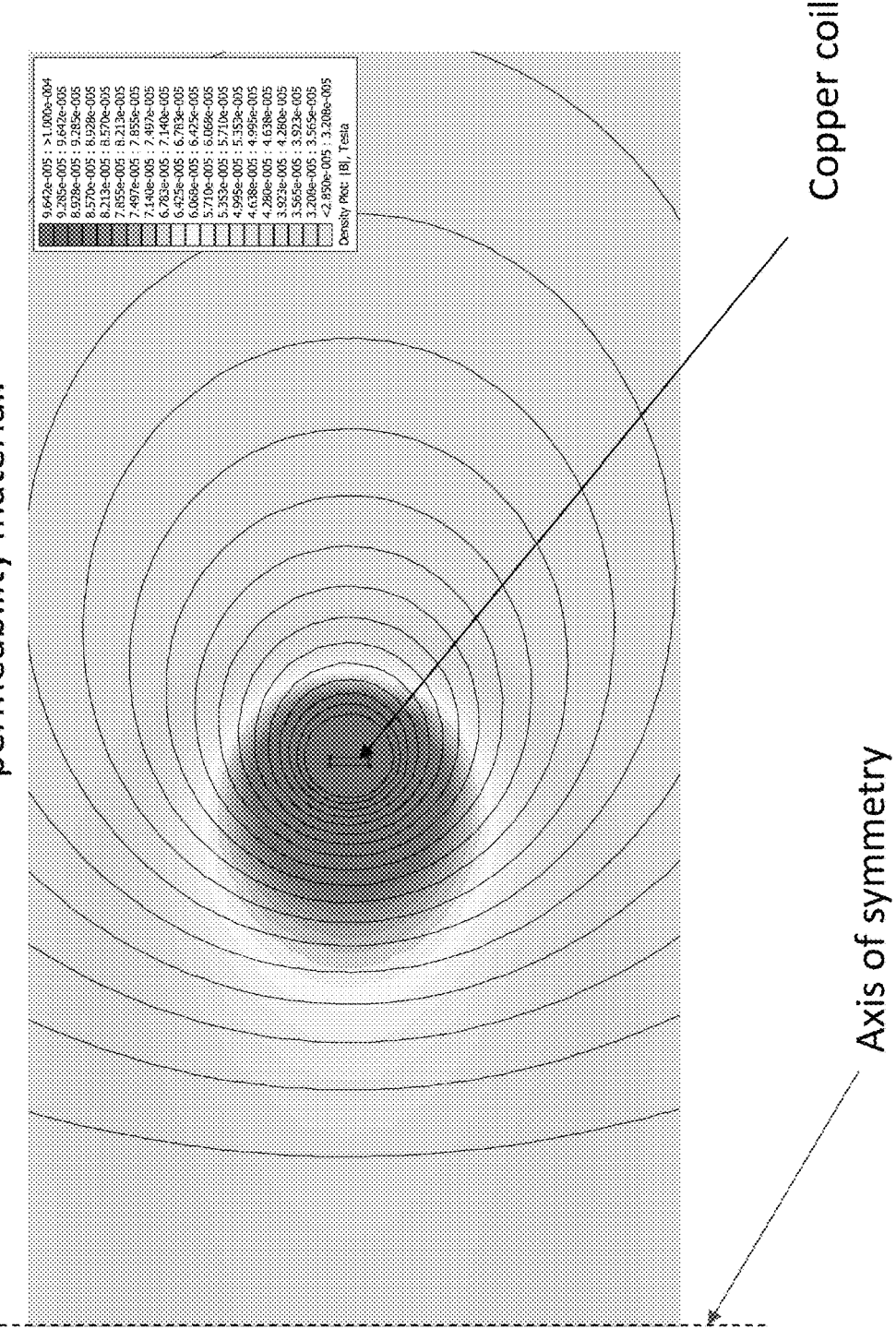
FIG. 37A is a heat map showing the relative magnetic field density (\B\, Tesla) for a section through one example of a charger device (e.g., collar) without using a high magnetic permeability material.
Figure 37B:
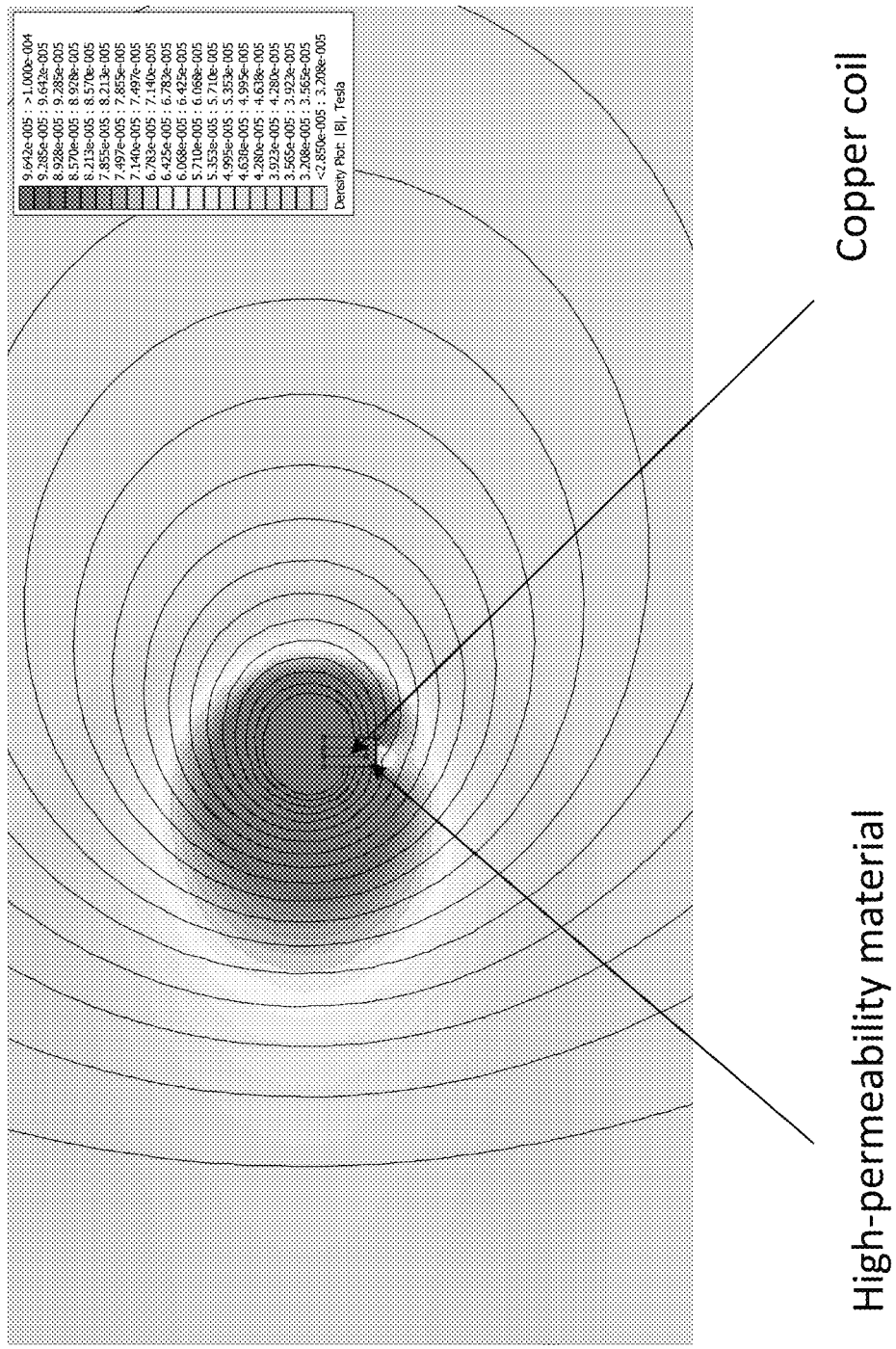
FIG. 37B is a heat map similar to the one shown in FIG. 37A in which the charger device includes a high magnetic permeability material forming a "U" around the magnetic coil of the charger, shifting the magnetic field upward, relative to the example shown in FIG. 37A.
Figure 37C:
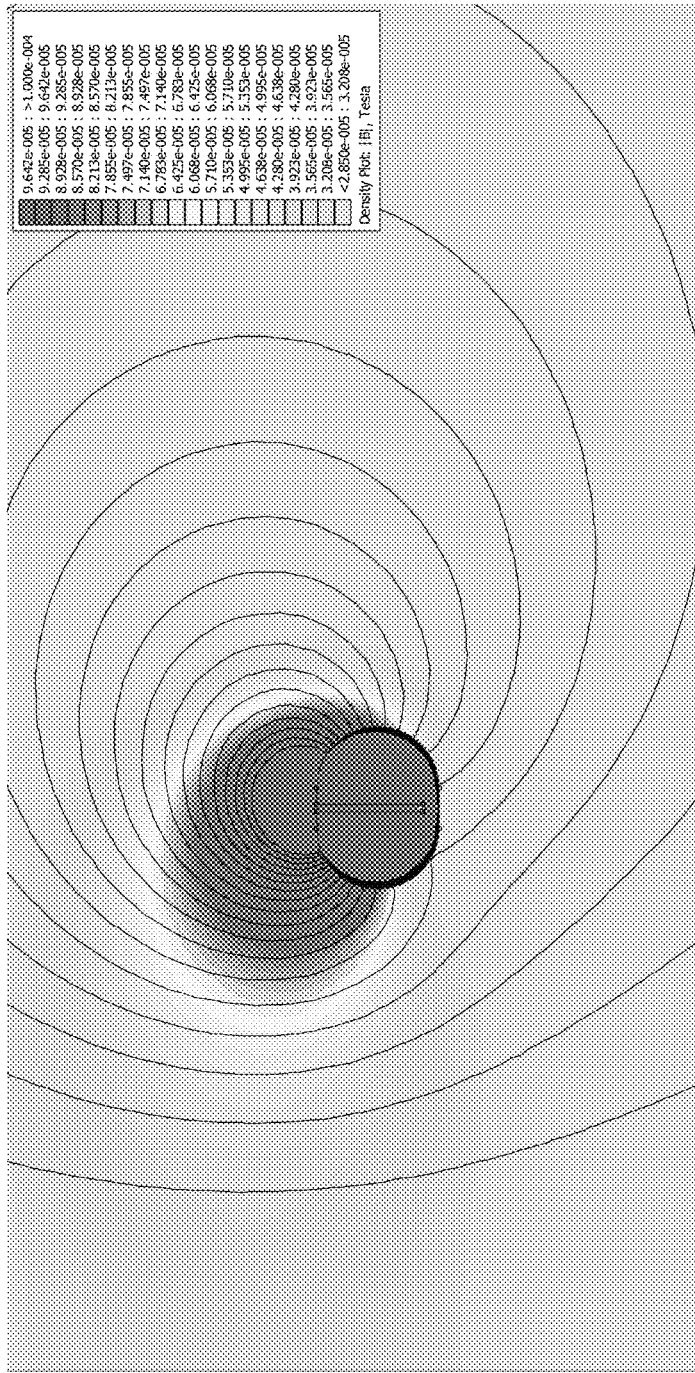
FIG. 37C is another example of a charger device using a larger quantity of ferrite material, producing an even more pronounced shifting effect.

For example, FIGS. 37A-37C illustrate the effects of a high magnetic permeability material added to one variation of a charger device. In FIG. 37A, the charging device is shown without any high magnetic permeability material shaping the field. The view shows an asymmetric view of a charger (configured as a collar) emitting a magnetic field that has a density of between >1e-4 Tesla and a 2.85e-5 Tesla. The field is emitted by a copper coil within the charger. FIG. 37B shows the effect of a high-permeability material which is formed into a U-shape around the copper coil. In this example, the magnetic field density is shifted upward axially (e.g., toward the subject's head, when worn around the neck). In this example, the magnetic permeability material is applied in a U shape, i.e. inside, outside and below the coil (or any one or more of these). Only the portion that is below the coil contributes to the axial asymmetry; inner and outer surfaces will raise inductance and Q, but do not have a "focusing" effect. FIG. 37C shows another example using a magnetic material, in which a larger amount of ferrite is used, producing a more pronounced shifting of the magnetic field density.

In other embodiments, the implant to be charged may be located in a different position with respect to the charger. For example, the implant may be located within the plane encircled by the transmitting coil of the charger. In this configuration, the high magnetic permeability material may be placed on the inside surface of the covering that faces the skin to concentrate the magnetic field inwards towards the implant. More generally stated, the high magnetic permeability material can be positioned around the transmitting coil partially on one or more sides of the coil. The implant may be above, below, or in line with the transmitting coil.

Thus, the charger may include a high magnetic field material on or within the charging housing, including in particularly on an inner face of all or a portion of the charger (e.g., on the inner, skin-facing surface when worn), on a top portion (e.g., where the top portion is closest to the patient's head when the charger is worn) or alternatively on a bottom portion (opposite the patient's head when the charger is worn). The high magnetic field material form a part of the outer housing of the charger, or it may be applied onto the outer housing. The high magnetic field material may be applied all the way around the charger or just around a portion of the charger.

For example, in some embodiments, the high magnetic permeability material can be integrated directly and permanently into the covering around the transmitting coil. In other embodiments, the high magnetic permeability material can be reversibly attached to the charger. For example, the high magnetic permeability material can be incorporated into an elastic sleeve that can be reversibly disposed over the charger and adjusted such that the high magnetic permeability material is correctly positioned, i.e., facing the implant. In other embodiments, the high magnetic permeability material can have a side covered with an adhesive so that the material can be adhered to the charger. In other embodiments, the high magnetic permeability material can have a latch or clamp or other fastener that can be used to reversibly attach the material to the covering around the transmitting coil.

Figure 35:
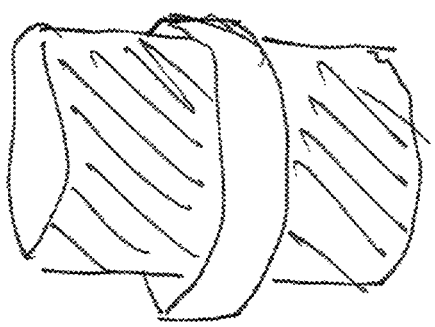
FIG. 35 illustrates an embodiment of a sleeve made of a high magnetic permeability material that can be used to enhance the magnetic field generated by a charger.

In some embodiments, the high magnetic permeability material can be disposed around the patient's neck in a separate device, such as a sleeve, liner or collar, and the charger can be placed over the high magnetic permeability material device, as shown in FIG. 35. For example, a sleeve, liner or collar made of a high magnetic permeability material can be placed over the patient's neck and over the implant position. The charger can then be placed around the sleeve, liner, or collar.

In some embodiments, where a conductive high-permeability material is used, in order to reduce eddy currents which reduce the efficiency of power transfer, the high magnetic permeability material (and/or in some variations the charger itself) can have one or more gaps or openings (e.g., slits). Alternatively, the high magnetic permeability material can be fabricated in a plurality of strips, slices, particles, grains, or powder that can then be incorporated into the covering or sleeve. Gaps in the high magnetic field material may spread out and/or re-orient the magnetic field over a region.

The systems described above can also be used to charge neurostimulators implanted in other parts of the body, such as the torso or limbs. The size of the charger can be made to fit around the body part, such as the torso, leg, or arm, and a high magnetic permeability material can be added as described herein to increase the efficiency of the power transfer.

Hand Held Charger

Figure 36:
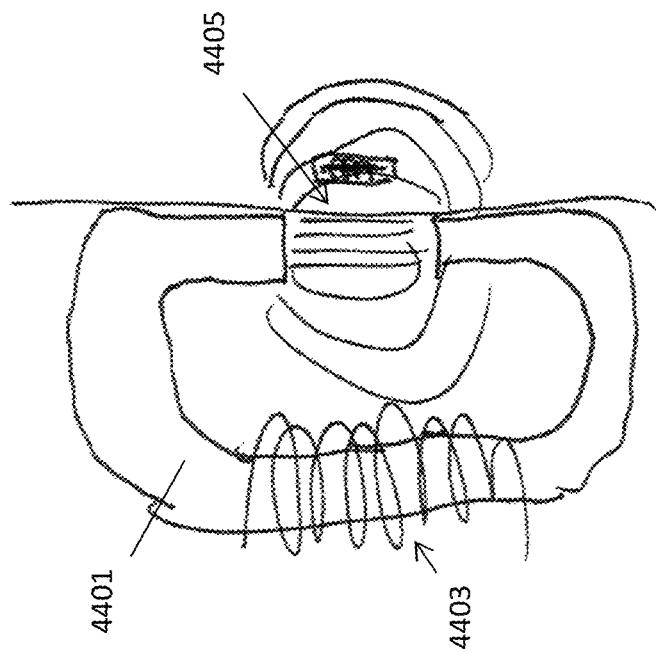
FIG. 36 illustrates an embodiment of a handheld charger.

In some embodiments, the charger can be a hand held device with a high magnetic permeability material, such as a ferrite core, having a gap 4405 between two ends, as shown in FIG. 36. For example, the high magnetic permeability core 4401 (e.g., ferrite core) can include gap or opening (e.g., forming a C-shaped structure). A coil 4403 can be wrapped around the core to generate a magnetic field that extends through the ferrite and across the gap. To use the charger, the gap between the ends of the ferrite can be placed against the patient's skin at the location wherein the neurostimulation is located under, and the orientation of the ferrite is adjusted such that the field lines that extend across the gap are oriented parallel to the receiving coil in the neurostimulator. In some embodiments, the gap between the ends of the ferrite core is between about 1 to 3 times the length of the receiving coil/antenna in the neurostimulator.

In general the size of the gap may be one to several time the length of the neurostimulator (e.g., between 0.8× to 3× the length of the neurotransmitter). For example, the size of the gap may be at least the length of the neurostimulator coil. The larger the gap, the longer the range of the charger.

Tester

Also described herein are tester apparatuses (testers) that may be used to monitor/test the implantable microregulator/microstimulator before, during or after implantation.

A surgical tester may be similar to a handheld charger as described above. For example, a charger may consist of a cylindrical ferrite core with copper windings. The core may be one to several times the length of the neurostimulator may be positioned adjacent and parallel to the neurostimulator to interact with the neurostimulator.

A tester apparatus may be used to test the microregulator/microstimulator (MR), as described in FIG. 38. For example, a tester may be used to detect failures that occurred during implantation. The tester may be used to interact with the implant prior to insertion without contacting the apparatus (without interfering with the sterile field), and may be used communicate with the implant during or after implantation. The tester device may be used to precondition the microstimulator (MS or MR) while in the sterile packaging or in the sterile field of the surgical theater. The tester device may also be used to test and/or write implant date or other data into the microstimulator in situ before surgical site closure. Verified error indicator signaling may be used to back up the implant. The tester may be disposable, and may be used without an additional device (e.g., controller or prescription pad). The tester may also be used to test devices before implantation (e.g., at the factory, etc.)

Figure 39A:
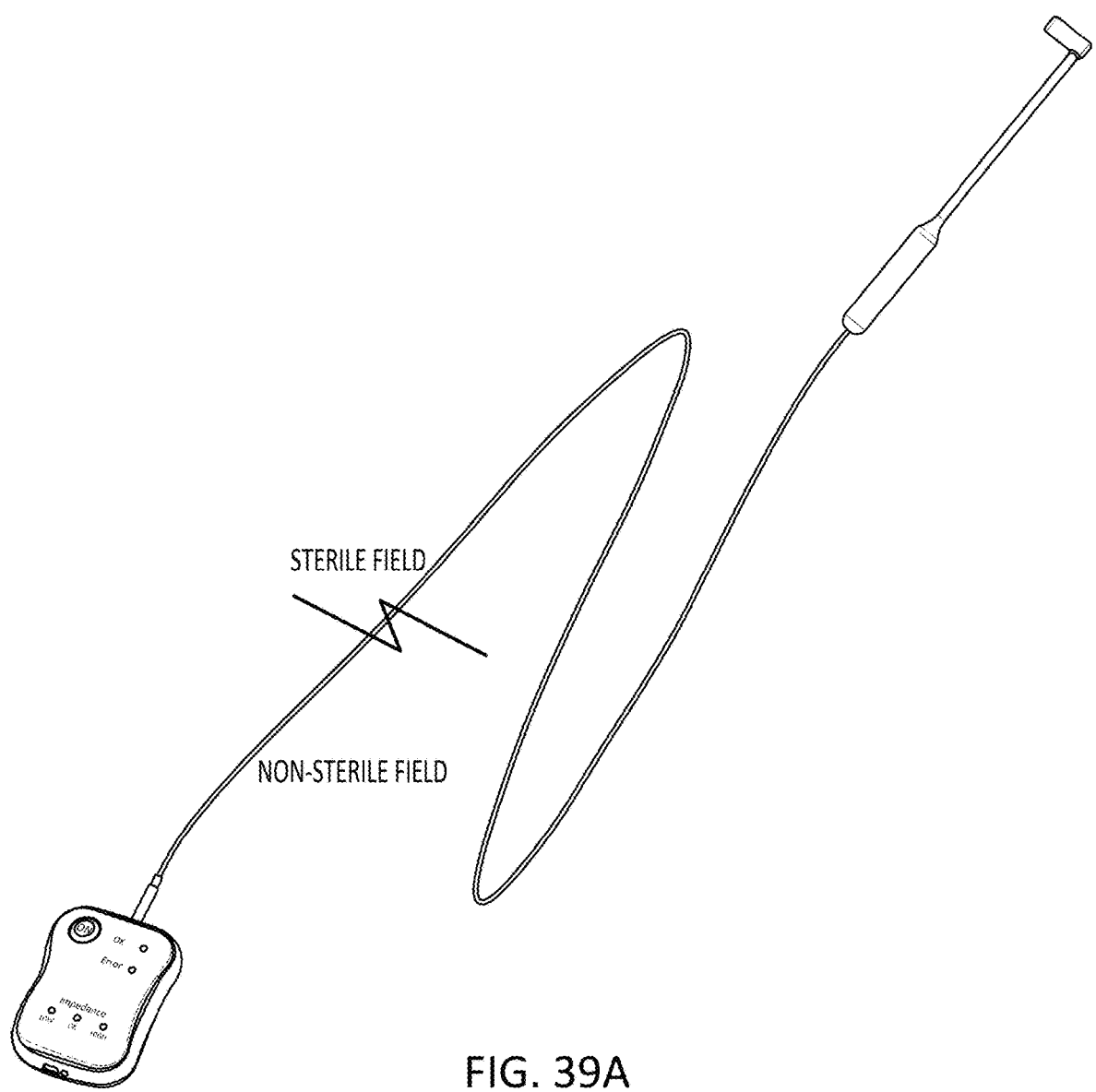
FIGS. 39A and 39B show one example of a surgical tester including a test probe portion (FIG. 39B) that may be used with/after implantation to confirm operation of the implant.
Figure 39B:
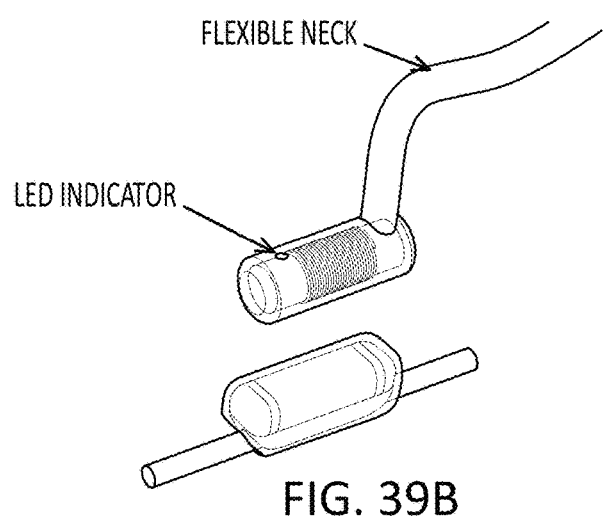

FIGS. 39A and 39B illustrate using a tester for in situ verification, during/after implantation of the MR, including across the sterile boundary. The implant may be used to initialize the MR (e.g., writing time/date, programming information, etc.). The distal end of the tester is shown in FIG. 39B.

Figure 40:
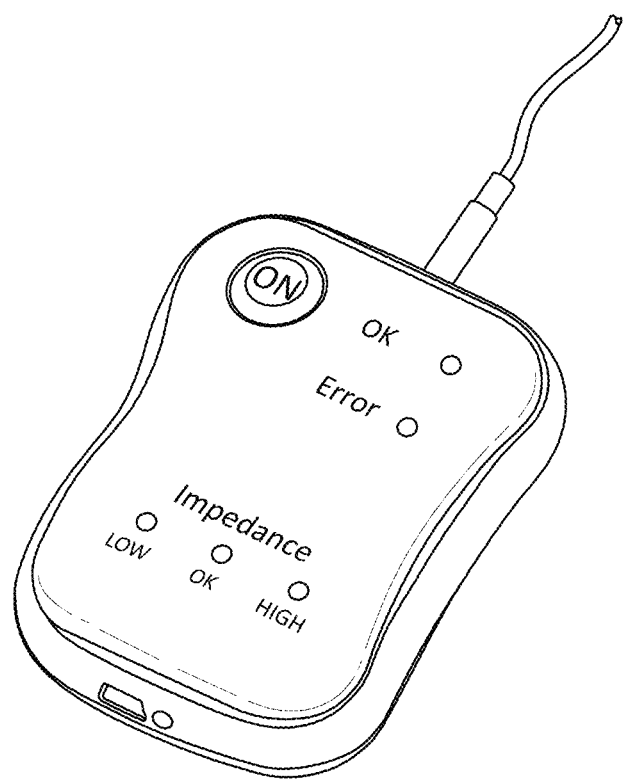
FIG. 40 illustrate one example of a tester (including a test probe) for an implant (microregulator/microstimulator).

FIG. 40 shows a view of the controller portion of an exemplary tester, including indicator lights (e.g., "OK", "Error", "Impedance (Low/OK/High), "On", etc.). The "On" button toggles the device on/off, the OK indicator may flash briefly and a busser may beep every second. As the probe locks to the microstimulator, the "OK" may flash and/or the device may buzz, beep, vibrate, etc. When the diagnostics are complete, the OK light may become solid and a long buzz may be triggered. An error output may be triggered to indicate a confirmed error (and signaling the technician/physician to go to the backup). When the probe is attached, the execution date of diagnostic may be logged into the implant and used as the implantation date by the controller (e.g., prescription pad).

Figure 41:
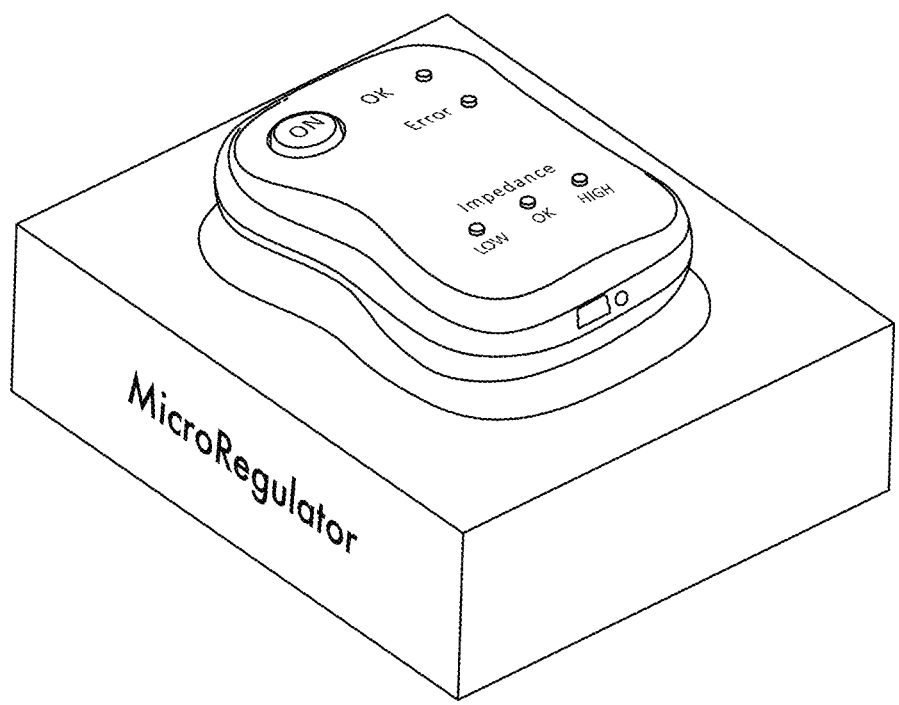
FIG. 41 shows a device interfacing with a microregulator within the sterile packaging of the microregulator.

A tester may include a probe (having a head) that is connected, e.g., via a cable, to a processor that controls (via inputs, e.g., user inputs such as buttons, switches, etc.) operation of the apparatus. For example, the tester may include outputs (e.g., LEDs, screen, etc.) showing the output mode(s) of the apparatus. For example, an apparatus may include overall status indicators (OK/error) and one or more indicators specific to the operational status (e.g., impedance—low, med, high, etc.). As shown in FIG. 41, the tester may be used before implantation to prepare the MR for insertion (e.g., charging, programming, verifying operation). The tester may also interface with the control software (e.g., smartphone, pad, tablet, etc.) as described above and shown in FIG. 42. For example, the tester may be charged with a USB cable/medical grad wall-wart. The time/date and firmware may be updated using the controller (e.g., prescription pad). However, the device may be used even without the control software of the prescription when necessary (e.g., to indicate device is functional and charged, e.g., ready for implantation, etc.).

Figure 43A:
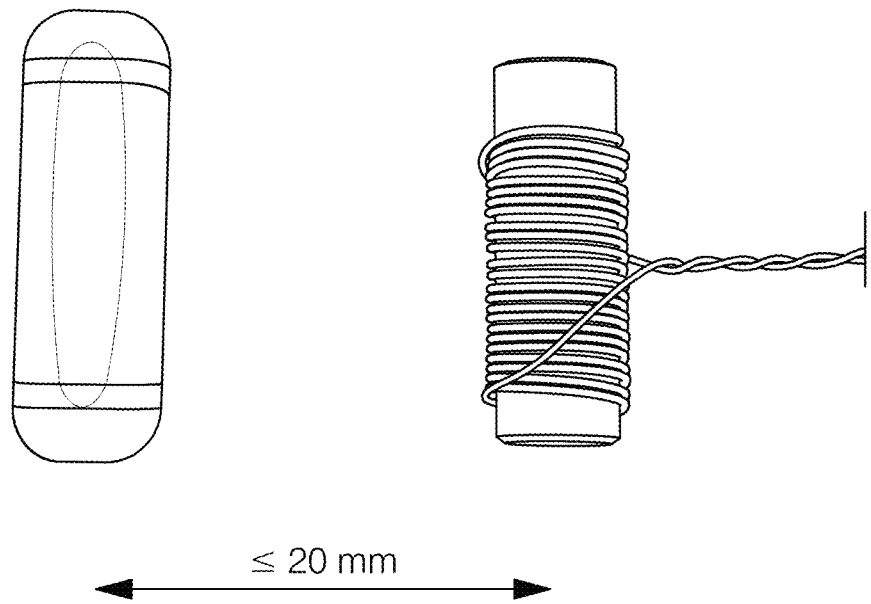
FIGS. 43A and 43B illustrate operation of a tester (mockup shown in FIG. 43A, model shown in FIG. 43B).
Figure 43B:
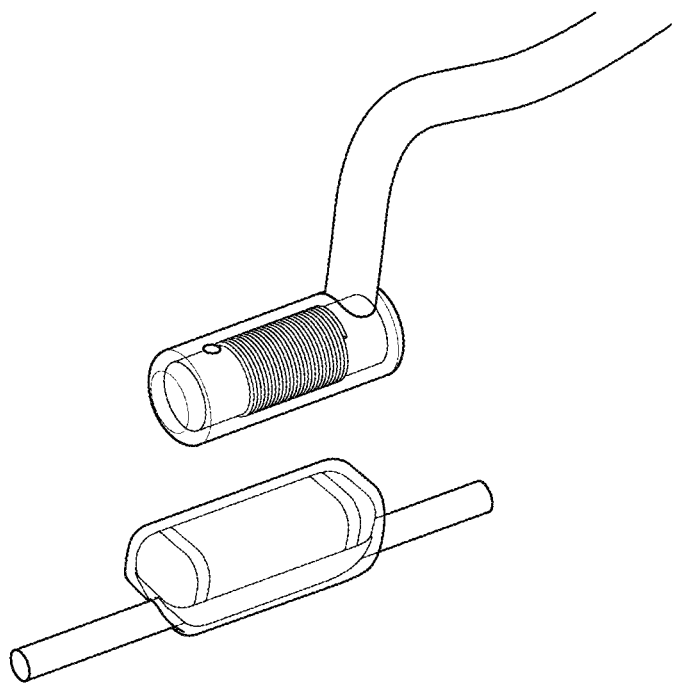

FIGS. 43A-43B illustrates the magnetic (coil) of one variation of an apparatus in which the coil is within 20 mm of the implant to communicate with the implant. In this example, the tool head encompasses the magnetic coil; the axis of the magnetic coil in the tester may be aligned with the magnetic coil (sensing coil) in the implant. In this example the head of the probe includes an LED that may indicate appropriate proximity and/or alignment.

Figure 44A:
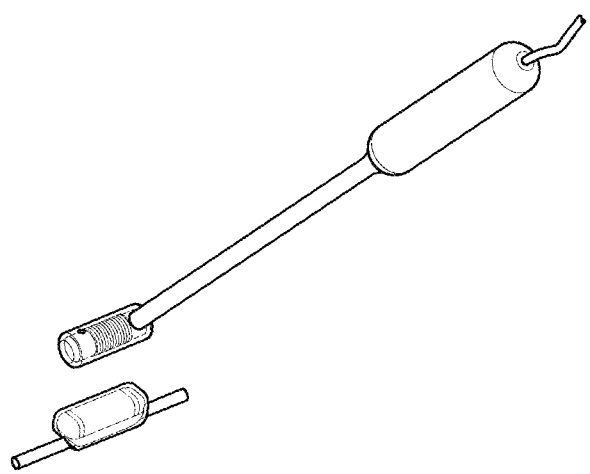
FIGS. 44A-44C illustrate an example of a tester having a flexible neck.
Figure 44B:
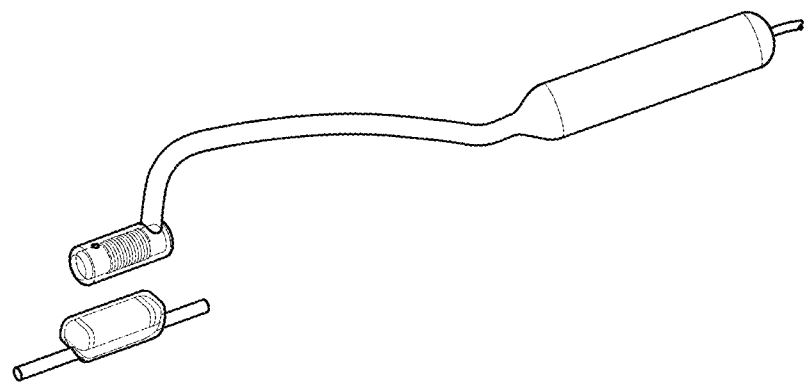
Figure 44C:
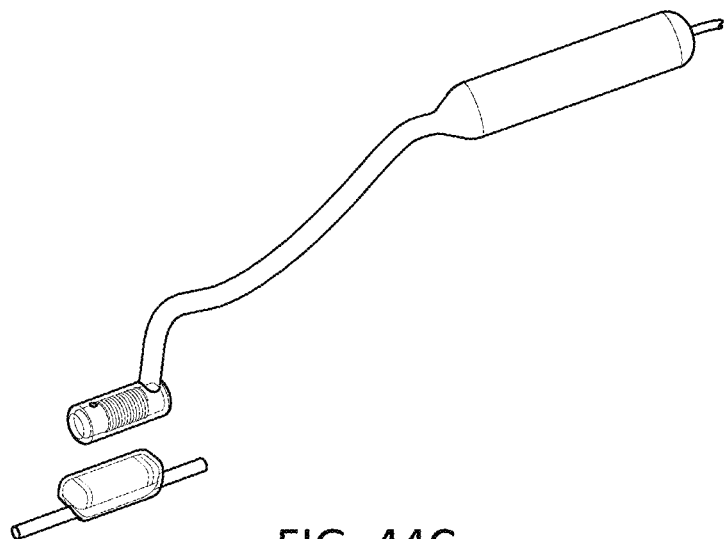
Figure 45:
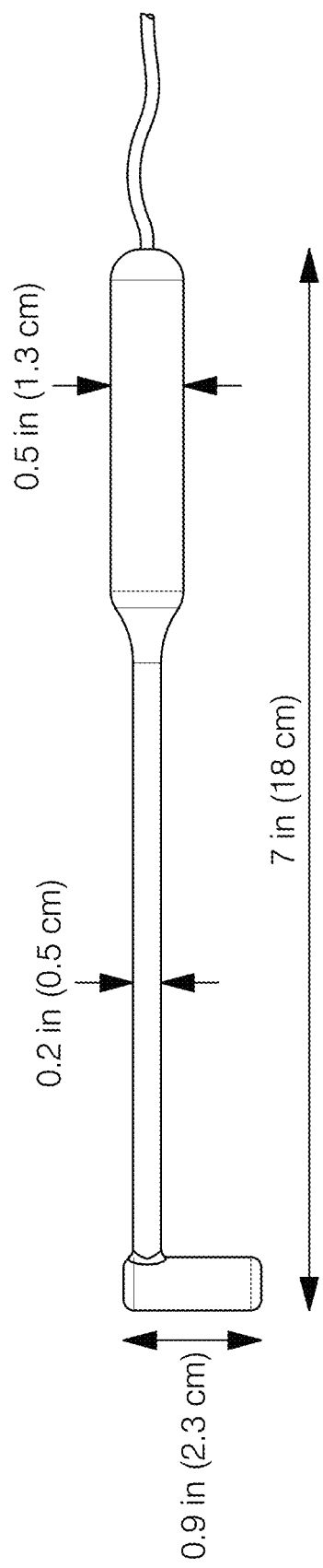
FIG. 45 is an example of the probe (distal end) region of a tester; the probe has a proximal handle and a distal head.

The tester may include a neck that is flexible but may hold its shape (as shown in FIGS. 44A-44C). FIG. 45 illustrates an example of a tester (probe portion) including exemplary dimensions/sizing that may be used.

FIGS. 46A-46D illustrates examples of different sized heads (the upper view is a side view, and the bottom shows a bottom view). The surgical tester may interface (e.g., by cable or wirelessly) with a smartphone, tablet, or the like. Thus, any of the systems described herein may include a tester, as shown in FIG. 47.

Also described herein are non-wearable recharging devices and systems that can be used to wirelessly transmit power to a non-stationary wireless receiver contained within an implantable neurostimulation device. As just described, a recharging system may include a necklace, belt, sash or collar type coil that a patient could wear for recharging the implanted neurostimulation device. Recharging devices may also be configured as pads, mattresses, or the like, so that a patient may reline on them for recharging. For example, any of these devices (shown below as 'pillow' devices may be configured as a pad or chair for lying/sitting on. The implantable neurostimulator device may be recharged while the patient is resting or sleeping.

Figure 48:
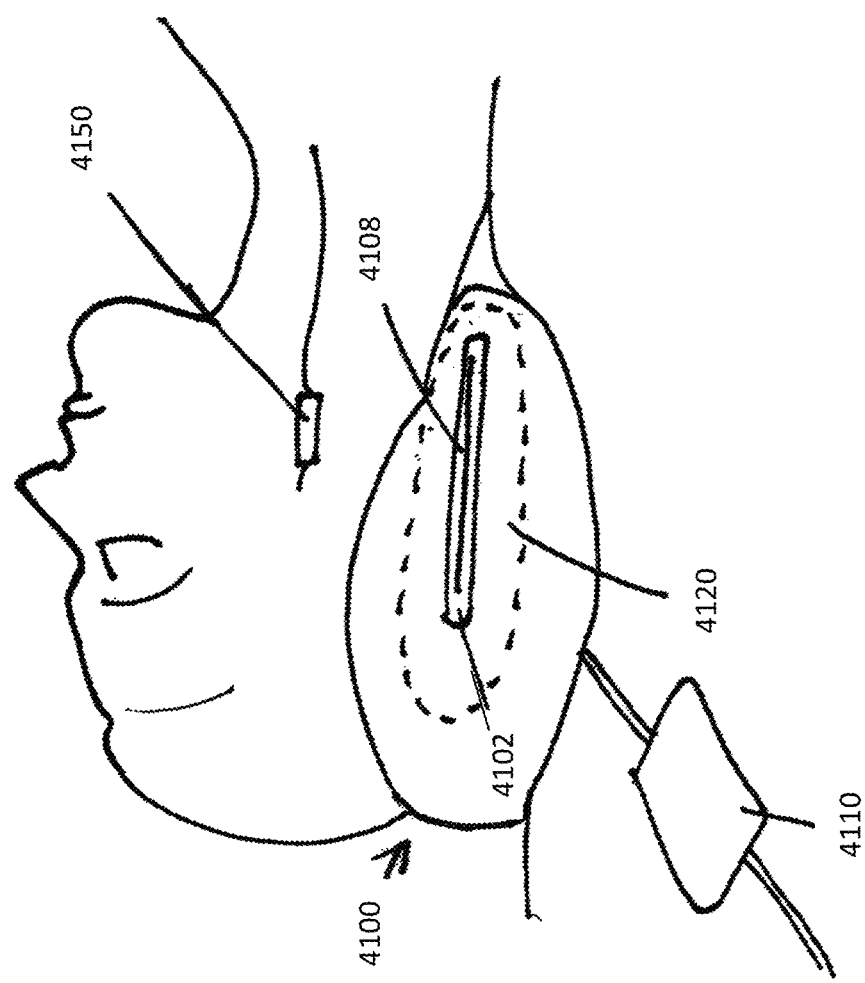
FIG. 48 shows a patient having an implantable neurostimulation device lying on the recharging pillow.

FIG. 48 shows a side view of a pillow recharger 4100. The pillow recharger 4100 includes a transmitter module 4102 that includes a transmitter coil 4104. The transmitter module 4102 may include a backing or support for the transmitter coil. The transmitter module may also include other circuitry that connects it to an external power source. The pillow recharger 4100 may also include an external controller module 4110 that allows the patient to set various parameters for recharging. Also shown in FIG. 48 is a possible position of a wireless power receiver 4150 within an implantable neurostimulator device.

The pillow recharger includes a transmitter that is able to provide a relatively uniform electromagnetic field within a given region such that the receiver module in the implantable neurostimulation device, which may include a receiving antenna made of a coil wrapped around a magnetic core, will be exposed to approximately the same amount of energy regardless of the positioning of the patient's head and neck relative to the recharging pillow. To inductively charge the neurostimulator, the transmitter generates an electromagnetic field with field lines that are approximately parallel with the axis of the coil of the receiving antenna, which allows the field lines to extend through the loops of the coils. In other embodiments, the electromagnetic field may not be relatively uniform.

Figure 49A:
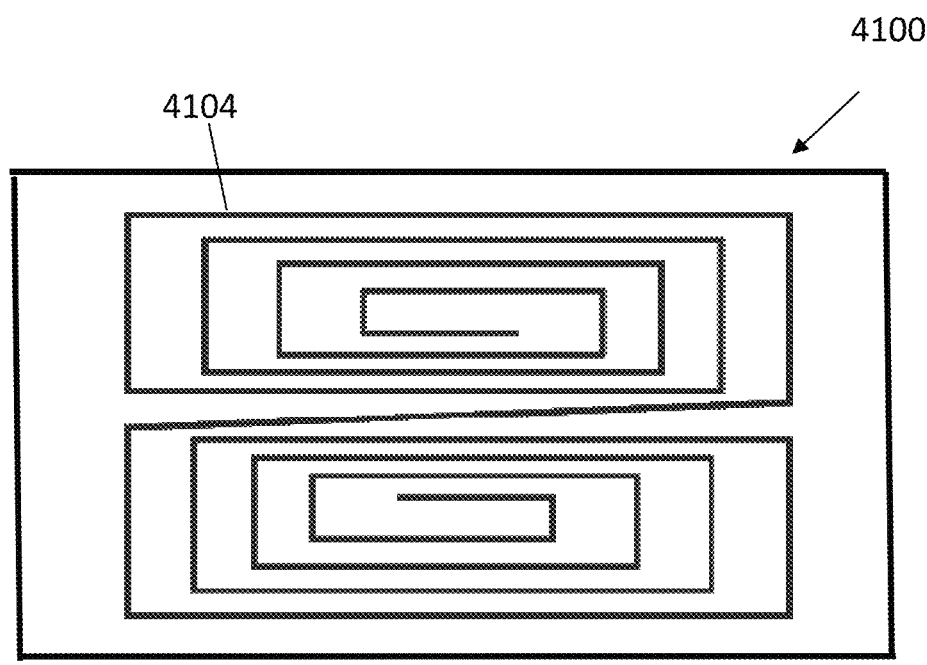
FIG. 49A shows the recharging pillow with an external controller and one possible transmitter coil arrangement.
Figure 49B:
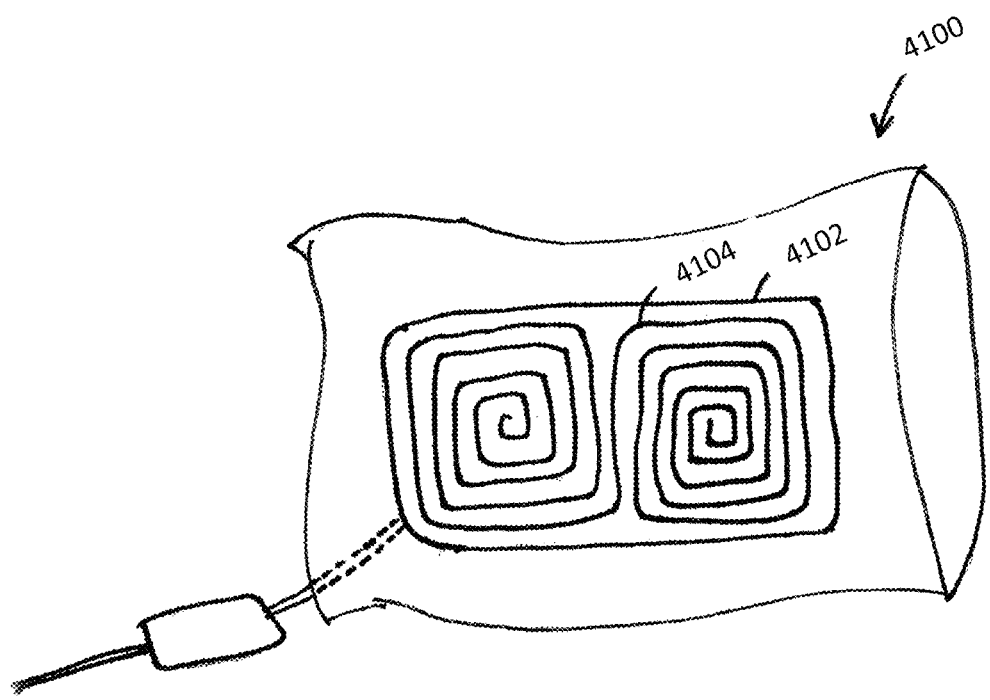
FIG. 49B shows a different transmitter coil arrangement within the recharging pillow.
Figure 51:
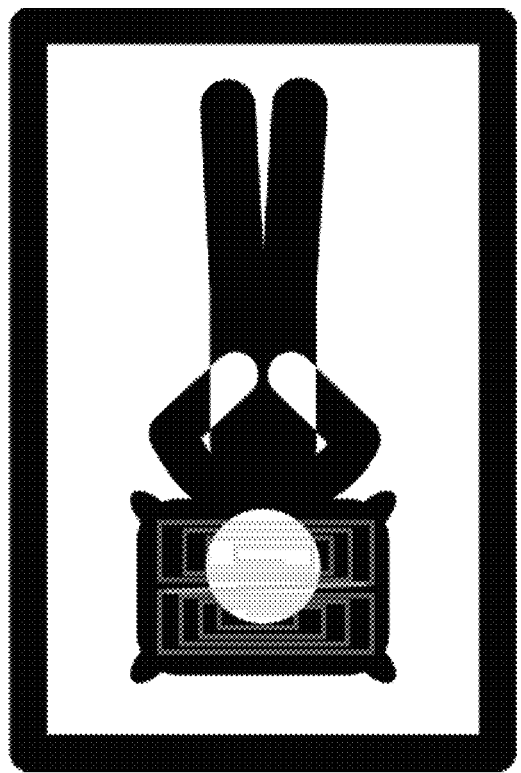
FIG. 51 show a person lying on the recharging pillow and the field lines emanating from the recharging pillow.

Turning to FIGS. 49A and 49B, are exemplary configurations of the transmitter module 4102 contained within the pillow recharger 4100 is shown. The transmitter module 4102 includes the transmitter coil 4104. As shown, the transmitter coil 4104 is a contiguous length of wire that loops into two concentric coils within a transmitter region of the pillow charger carving out an essentially figure eight configuration. The current runs through the two coils in opposite directions, in the sense that the current runs in a counterclockwise direction in one coil and a clockwise direction in the other coil, in order to generate the proper magnetic field. While the coils shown in FIGS. 49A and 49B are rectangular and square in shape, it is conceivable that the figure eight transmitter coils are circular, oval, polygonal, or other any other suitable shape. Further as shown, the coils are evenly spaced, but in other configurations, the coils may be spaced apart at varying degrees (e.g. 0.1 cm, 0.5 cm, 1 cm, and so forth). In general, each coil produces an electromagnetic field that goes up along a z-axis (if we define the transmitter coil being generally within the x and y axes) through the coil on one side of the figure eight and down through the other side of the other coil, with horizontal field lines in the x-y plane in between, as shown in FIGS. 50A and 50B, described further below. The electromagnetic field generated by the transmitter coil 4104 has field lines that extend through the coil of the receiving antenna. For example, when the microstimulator is attached to the vagus nerve in the neck, the coil of the receiving antenna has an axis that is aligned with the vagus nerve. Therefore, the transmitter coils can be arranged to generate field lines in the xy plane that extend along the caudal-rostral axis of the patient's body. FIGS. 49A and 51, for example, illustrate an example of a coil configuration that generates such field lines. More generally, the two transmitter coils can be arranged along the same axis as the coil for the receiving antenna of the microstimulator. For example, FIG. 49B illustrates two coils arranged along medial-lateral axis, and therefore would be suitable for charging a coil oriented along the medial-lateral axis. Alternatively, the pillow can be turned 90 degrees or some other amount to change the orientation of the two transmitter coils with respect to the patient's body and align the transmitter coils with the receiving coil of the implant.

In other non-limiting variations, there may be two separate coils that produce a resultant electromagnetic field that goes up along one direction of the z-axis and then arcs down and goes in the opposite direction of the z-axis and has a horizontal component that extends between the two coils. As described above, this can be achieved by running the current in opposite directions for each coil (clockwise in one coil and counterclockwise in the other coil). In yet other examples, there may be multiple transmitter coils that are able to provide the desired resulting electromagnetic field patterns as described earlier. In some variations, it may also be possible to detect which of these sets of coils is most strongly coupled to the receiving antenna, and run current through only that set of coils.

Finally, while in both FIGS. 49A and 49B, the transmitter coils are shown centered within the recharging pillow, it may also be possible to have transmitter coils that are not centered within the pillow dimensions. For example, the transmitter coils may be positioned to be closer to the receiving antenna when the patient lies on the pillow in a natural manner.

The transmitter coil 4104 may also be supported with a backing or support for maintaining the shape of the transmitter coil. While the backing may be of any suitable material, it may be advantageous to select a material that can aid in maintaining a near uniform field distribution over the transmission coils. Thus, materials like aluminum or any other suitable electromagnetic reflective material or materials may be desirable. The backing may be a solid sheet of material or materials or the backing may include holes or perforations. The spacing of the transmitter loops may be adjusted to achieve nearly uniform field distribution over the figure eight coils. In some examples, the transmitter coil backing may include protrusions or couplers to better maintain the shape of the transmitter coils.

As previously alluded to, the transmitter coil is part of a resonant circuit tuned to a particular frequency or may allow for some tuning to maximize the energy transfer between the external wireless transmitter and the implanted receiver coil. Because the transmitter coil may be affected by its surroundings that in turn may alter its resonant frequency, such as when the implantable receiver coil is moved closer or farther away in proximity, in some instances, shielding using a highly magnetically permeable and/or conductive material may be employed. A shielding material, such as a ferrite sheet, or a sheet made of another high magnetic permeability material, that may be part of a support structure for the transmitter coils may offer greater energy transfer properties in addition to shielding from potentially interruptive materials in the vicinity of the recharging pillow.

The wireless power transmitter 4102 may also include a power generator and related circuitry for providing power to the transmitter coil.

When the implantable neurostimulator requires charging, the included wireless receiver may transmit a signal to the wireless power transmitter that would initiate an initiating signal which turns the power generator on. The power generator now can supply energy (drive signal) to create an alternating magnetic field that oscillates within a threshold of the desired resonant frequency. The resonant frequency may be tuned by adjusting the coil spacing and dimensions. In some variations, tuning may be achieved by adjusting the capacitance in the LC circuit, e.g. by switching in additional capacitance using FETs.

FIG. 50A shows a side view of the pillow recharger 4100 along its short axis and FIG. 50B shows a perspective view of the pillow recharger 4100. As both of these figures show, the magnetic field lines travel up from one side of the coil and down towards the adjacent coil. The dashed lines show the magnetic field pattern produced while the transmitter module 4102 is ON. Thus, while the transmitter module 4102 is ON, a corresponding wireless power receiver may be properly charged at different locations with respect to the pillow. In the configuration described, the magnetic field generated may result in an electromagnetic field that is within a suitable range for recharging (e.g. 50 kHz, 100 kHz, 150 kHz, 200 kHz, and so forth).

Turning to FIG. 51, this figure shows a representation of a person laying their head on the recharging pillow. Because the transmitter coils may be formed to cover a large region of the pillow, as long as the person's head is on the pillow, a sufficient electromagnetic field will be able to reach the wireless receiver in the implantable neurostimulation device for recharging.

Next, there may also be a level of intelligent control based on the position of the wireless receiver module. Because the wireless receiver module (e.g., implant) position does not necessarily remain stationary on the pillow charger during charging, it may be advantageous to be able to determine where the wireless receiver module is in relation to the wireless transmitter. The regions of the wireless transmitter may be delineated into regions, including quadrants, where each region may have a unique identifier (e.g., which corresponds to a specific region of the wireless transmitter when the wireless receiver is above it). When actively charging, the wireless receiver may ascertain a tag associated with the particular wireless transmitter region and adjust the power output such that the energy sent to the wireless receiver remains essentially constant even if the position of the wireless receiver module has changed. In some embodiments, each region may have its own set of transmitter coils that can be separately powered. Any of the various sets of coils may be used to address various angular orientations as well as spatial positions.

A wireless power transmitter may be connected to either an internal or external power supply. The wireless power transmitter may also include a controller for manual control of the recharger. A user will be able to power ON or OFF the pillow charger or select a time period for charging or allow the system to automatically turn on for charging and OFF when done.

The wireless power transmitter may also include sensors or indicators. Sensors and indicators may be of the type that alerts the user as to when charging is required or when charging is complete. Sensors may include temperature sensors that monitor the temperature of the pillow at its surface or near surface. Because the wireless recharging system is incorporated into a pillow, it may be desirable to be able to silence certain indicators so not to disturb the user's sleep. In other instances, certain indicators may not be silenced, such as in the case of a temperature sensor alarm that alerts the user of overheating at the pillow surface.

Figure 52A:
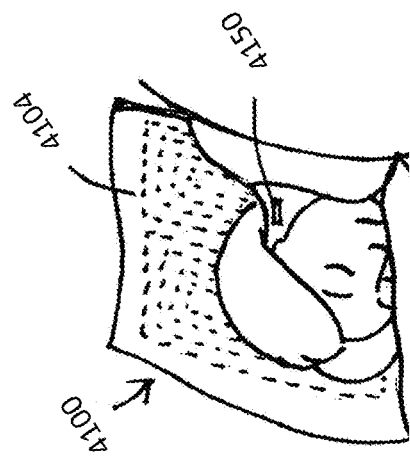
FIGS. 52A-52C show the patient in different positions on the recharging pillow and the position of the wireless transmitter relative to the implantable neurostimulator module.
Figure 52C:
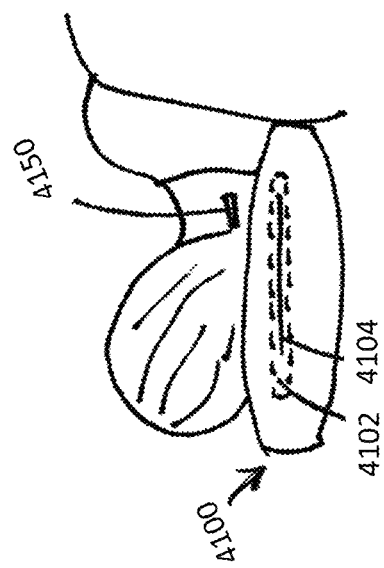
Figure 52B:
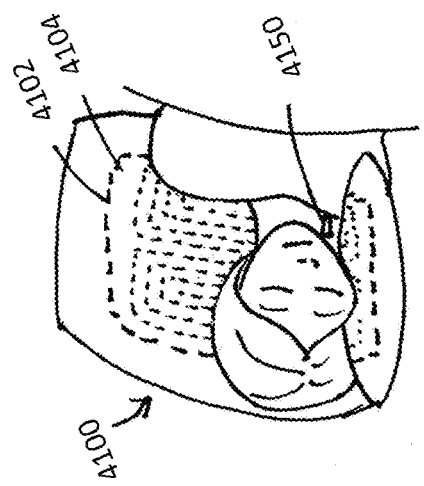

The wireless power receivers contained within the implantable neurostimulation unit, as the term suggests, receives inductive power from the wireless power transmitter. Going back to FIG. 48, the wireless power receiver module 4150 is shown relative to the recharging pillow 4100. The wireless power receiver module 4150 may be helical or spiral in shape where its longitudinal axis is parallel to the longitudinal axis of the vagus nerve. Here, even though the location of the wireless receiver module is not stationary, even if the patient moves about during normal sleep, more likely than not, their neck is still within the transmission coil region where the distance between the transmission coil and the receiver coil are still within an acceptable distance from each other for power transmission (e.g. 2 inches, 3 inches, and so forth). FIGS. 52A-52C shows possible sleeping orientations of a patient. As can be seen, the wireless power receiver 4150 is always with an acceptable range of distance from the transmitter coil 4104 even when the patient is moving about.

While the transmitter coil and receiver coil alignment as shown in the figures will successful charge for the majority of the various sleep orientations, there may be patient sleep orientations that increases the distance between the wireless transmitter coil and the wireless power receiver (e.g. patient sleeps on their stomach or patient sleeps with an arm under their head). Thus alternatively, it may be useful to have a receiver coil that is able to receive energy transmission even if the orientation of and the distance between the transmission and receiver coils are not optimal. In these variations, the receiver coil may be a multi-axes wireless power receiver coupled to a circuit board, where the circuit board includes circuitry for functional components such as controllers, sensors, logic, and so forth. The multi-axes power receiver may include a support structure onto which the wires may be wrapped along more than one axes to achieve proper resonance matching with the wireless power transmitter. The support structure may be composed of a ferrite sheet or plate of any suitable shape. The support structure may include notches or protrusions for retaining the wrapped wire coils. The wrapped wire coils may also be wrapped around the exterior of the support structure. In some examples, the wires may be wrapped in a combination of directions from top to bottom and side to side, around the support structure, and so forth. The number of turns of the wire for each axes may be variable, such as 10 turns, 20 turns, 30 turns, and so forth. The corresponding antennae outputs may each be connected in parallel, having a value where each coil resonates at the driving frequency of the wireless transmitter, e.g., when the antenna outputs are rectified prior to being connected in parallel. The outputs may also be kept separate.

In some instances, the wireless receiver also includes a capacitor or a battery that will be able to store the power received through the wireless power receiver module 4150.

With the figure eight transmitter coil configuration, in some embodiments, the electromagnetic field created passes out the top portion of the one of the coil halves of the figure eight and then drops down into the other coil halve of the figure eight.

Because the charger described herein may communicate (e.g., recharge) the implantable neurostimulation device while the patient is lying or sleeping on the charger, it is desirable that the wireless transmitter units (including the coil, supporting circuitry, power supply, and other components) remain at a safe temperature to avoid burning the patient (especially when the patient's senses will be slow to respond to such stimuli due to sleep). In some instances, temperature sensors may be included at various locations at or near the pillow surface to ensure that an upper threshold temperature is never reached. The system may also include a cooling mechanism that is able to bring the temperature of pillow down to a safe level if the temperature sensor detects overheating. (In other variations, a flux concentrator may be incorporated into the receiving coil, such that when the temperature exceeds the Curie temperature for the flux concentrator material, the flux concentrator loses their magnetic properties and thereby de-tunes the resonant inductive coupling of the wireless receiver with the wireless power transmitter.)

Note that the inductive communication between the charger and the implants described herein may refer to both charging of the implant from the energy emitted by the charger and communication of information between the two, including in particular, commands for stimulation protocols from a separate controller (e.g., the "prescription pads" described above, which may be a handheld processor such as a smartphone, pad, wearable, etc.). Information from the implant may also be communicated inductively; a communication signal from the charger to the implant may ride on top of the power signal (e.g., may modulate the power signal) or it may be separate from it.

Another consideration for the chargers described herein may be that the internal wireless transmitter components may be protected from a certain amount of force when the patient places their body (e.g., abdomen, torso, head, etc.) on the recharging pillow. Adequate cushioning in the way of sealed air compartments or cushioning materials (e.g. cotton, polyester fill, foam, gels) may be used to further pad and protect the areas around the wireless transmitter module. It may also be desirable to enclose the wireless transmitter module in a waterproof covering to prevent moisture from reaching the transmitter components.

Overall, the pillow recharger may be configured to feel like a traditional pillow cover, e.g., made of natural and/or synthetic fibers. The pillow recharger may include cushioning fill of either natural or synthetic fibers. Note that any of the "pillow" chargers described herein may be configured for charging an implant implanted sub-diaphragmatically, as mentioned above. Thus, these chargers may be configured as mattresses, pads, backrests, seats, etc. for communicating with the implant. Thus, although referred to as a pillow charger, the charger can take a form other than a pillow for a patient's head, such as a pad that can be placed under any portion of the patient to inductively charge an implant located in various locations of the body.

Batteryless Microstimulators

Any of the microstimulators described herein may be configured as batteryless implants. Such implants may provide VNS (vagal nerve stimulation) only when in the presence of a sufficient inductive filed. Such implantable microstimulators/microregulators (MS/MR) can be used to electrically stimulate a nerve such as the vagus nerve for therapeutic purposes, including for treatment of chronic inflammation, such as rheumatoid arthritis and Crohn's disease, by providing neurostimulation of the cholinergic anti-inflammatory pathway. Sub-diaphragmatic stimulation may be particularly well-suited to the use of a batteryless implant, which may be smaller, and lighter without the battery, however it may pose specific challenges, including matching the orientation and identifying such devices. For any of the apparatuses and method described herein, vagus nerve stimulation can also be used to treat other conditions, such as modulating sirtuins levels as described in U.S. Patent Application Publication No. 2013/0079834 to treat a variety of disease and conditions, or modulating levels of Receptor Activator for Necular Factor kB Ligand (RANKL) and/or osteoprotegerin (OPG) for bone erosion or treatment/prevention of cancer as described in U.S. Patent Application Publication No. 2013/0253413. Treatment of epilepsy, depression, headaches, and other neurological disorders can also be accomplished through vagus nerve stimulation.

Various battery-based MR for electrically stimulating a nerve, such as the vagus nerve, have been previously described in U.S. Pat. Nos. 8,612,002 and 8,886,339, herein incorporated by reference it their entireties, and in the examples provided above. Advantages of a battery based MR include automatic dosing, which leads to increased patient compliance to prescribed treatments and increased ease of use. In addition, a battery based MR can more conveniently automatically provide multiple stimulations per day when compared to a batteryless MR which may need patient action for each stimulation. In addition, a battery based MR can include sensor feedback from a motion sensor or a sensor to measure heart rate for closed loop stimulation as further described in U.S. Provisional Patent Application No. 62/286,957, filed on Jan. 25, 2016, and U.S. Provisional Patent Application No. 62/340,950, filed on May 24, 2016, each of which is herein incorporated by reference in their entireties.

Figure 53:
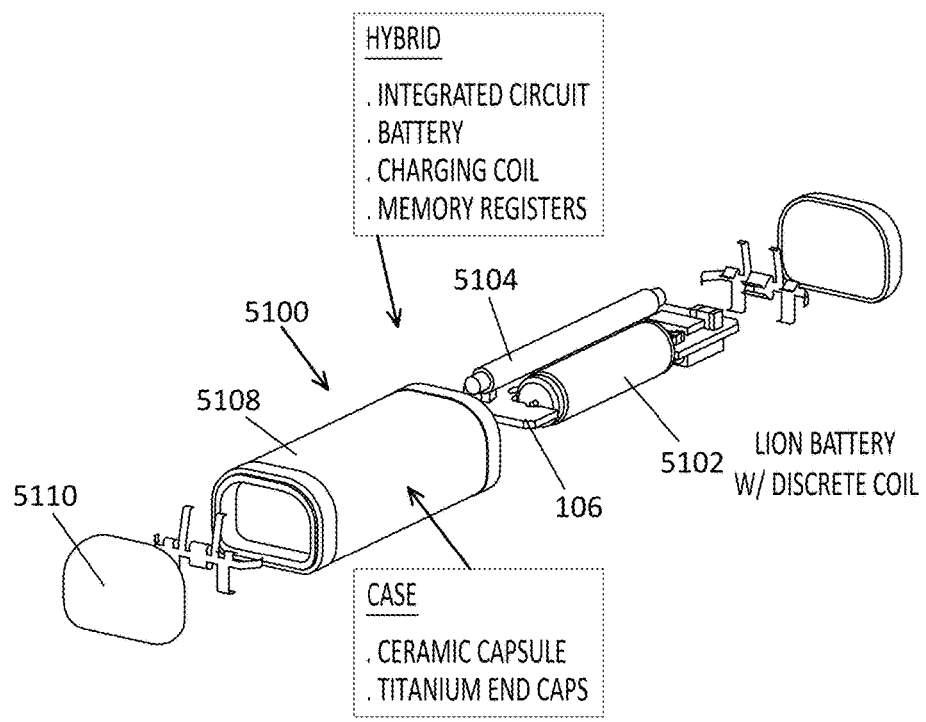
FIG. 53 shows an example of a microregulator/microstimluator including a battery.

FIG. 53 illustrates an embodiment of a microstimulator 5100 with a battery 5102, such as a rechargeable LION battery, and a discrete charging/data transmission coil 5104 for charging the battery. Additional components of the MR include one or more integrated circuits and memory. A printed circuit board (PCB) 5106 can be used to electrically connect the various components together. The electrical assembly can be encapsulated within a capsule 5108, which can be made of a nonconductive material such as a ceramic, and conductive end caps 5110, which can be made of titanium or another biocompatible metal or alloy. The apparatus may include an integrated circuit, battery charging coil and memory registers, as shown.

Figure 54A:
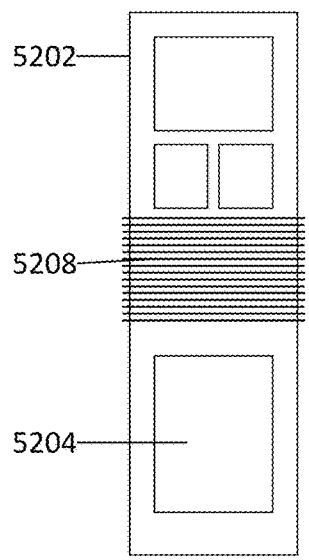
FIGS. 54A and 54B illustrate another embodiment of a microstimulator with a battery from top and side views, respectively.
Figure 54B:
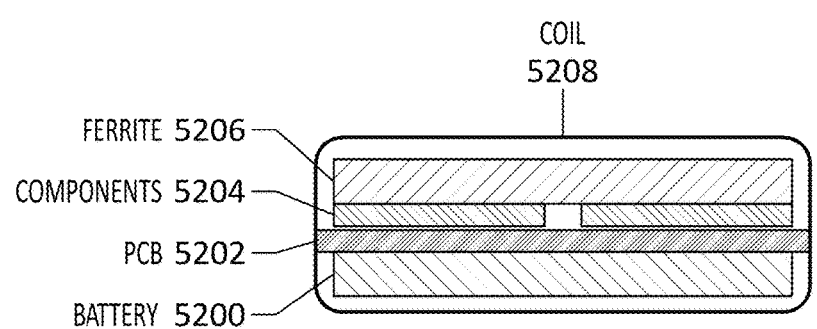

FIGS. 54A and 54B illustrate another embodiment of a microstimulator with a battery. In this embodiment, the MR can have a battery 5200, which can be a solid-state battery, which can be disposed on one side of the PCB 5202, while the electrical components 5204 such as the integrated circuits and memory can be disposed on the other side of the PCB. A ferrite 5206 can be disposed over the electrical components, and a laminated coil 5208 can be wrapped around the entire electrical assembly.

Figure 55:
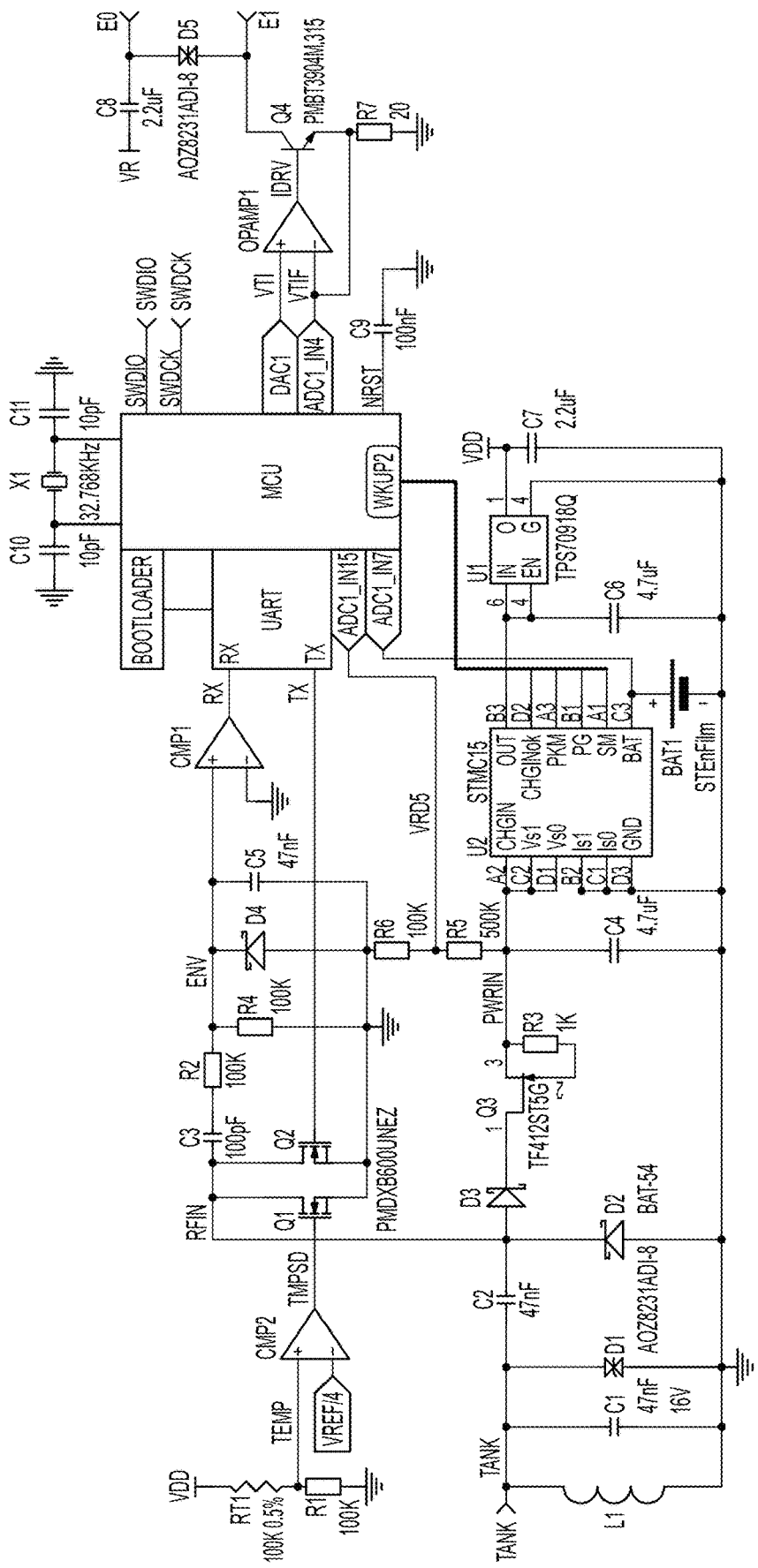
FIG. 55 is a schematic of a circuit for a MR including a battery.

FIG. 55 illustrates a circuit diagram for a hermetic MR with a battery, as shown in FIGS. 53-54B for example. L1 & C1 form a tank circuit that resonates at a set or predetermined frequency, which can be ~131 KHz. D1 prevents the tank circuit voltage from going beyond a set or predetermined voltage, which can be 10V for example. C2, D2, & D3 form a voltage doubler and impedance matcher. Q3 & R4/R3 limits current to avoid circuit chattering. R5 and R6 scale down PWRIN voltage to be read by the microcontroller (MCU). Q1 shorts the Tank if the temperature as measured by RT1 exceeds a set or predetermined temperature, such as 41.5 C. C3, R2, R3, D4 & C5 extract the AM modulated carrier to extract incoming data. CMP1 slices the data that feeds into the UART RX line. Q2 receives UART TX line and modulates carrier with return data. U2 charges battery at a set or predetermined voltage, such as 4.2V, limiting current to a set or predetermined current, such as 10 mA, and prevents over discharge. U1 regulates PWRIN, a variable voltage that ranges from 3.3-16V, to a set or predetermined voltage such as 1.8V to power the MCU. DAC1 drives a voltage to current converter (OPAMP1, Q4 & R7) to drive stimulation electrodes (E0, E1) where C8 protects against DC. ADC1_IN4 measures compliance voltage where impedance can be calculated. ADC1_IN7 measures battery voltage. A piezoelectric crystal, X1, can be used as a clock to track time for autonomous dosing.

As an alternative to a battery based MR, in some embodiments the MR can be batteryless. Since the MR does not have a battery, another device, such as an energizer, is provided to power the MR. Since the batteryless MR is a passive device until powered by the energizer, a patient reminder feature is preferably provided to the energizer or another device, such as a smart watch or a smartphone that can be worn or carried by the patient.

One advantage of a batteryless MR over a battery based MR is a lower cost. The parts for the batteryless MR can be much lower cost than the parts of a battery based MR, as the battery alone may add substantial cost. Another advantage is that the size of the batteryless MR can be about ⅓ the volume as a battery based MR, which allows the batteryless MR to be applied to many other nerves, particularly smaller nerves. As described below, a mold insert for a silicon overmold can be used to set the size of the nerve channel for the MR. Smaller size also facilitates the use of endoscopic and/or laparoscopic procedures for implantation. In addition, the reduced electrical components and the materials used allow the batteryless MR to be tested under accelerated life tests that can be run at 90 degrees Celsius. The tradeoff is that implant life may be reduced as compared to a hermitic battery based MR, depending on the properties of the materials used to fabricate the batteryless MR. Since an external energizer is used to deliver electrical stimulus through the batteryless MR, it may rely on manual operation rather than autonomous operation, because the batteryless MR may generally not be powered unless in proximity to an external energizer. A separate sensor such as an ECG device may be worn to measure continuously (e.g., even when not in the inductive field), e.g., to measure heart rate variability (HRV) or other parameters, for example.

FIGS. 56A-56D illustrate one embodiment of a batteryless MR. FIG. 56A illustrates an embodiment of a PCB 5400 with a ferrite 5404 and electrodes 5402 attached to and in electrical communication with the PCB 5400 that can be formed around a mandrel. The mandrel can have a circular, oval, elliptical, or oblong cross-sectional profile so that the molded PCB 5400 and electrodes 5402 are shaped to form a nerve channel with a matching cross sectional profile for receiving a nerve, such as the vagus nerve or other peripheral nerve. The size and shape of the mandrel cross-section can be matched to the nerve. For example, in some embodiments, the mandrel can be oval or elliptical with a 4×3 mm cross section. In some embodiments, the initial mandrel can be partially rectilinear, or have flat section that corresponds to the PCB, and curved sections that correspond to the electrodes. The initial mandrel can be used to shape the electrodes, while a second mandrel can be used to form a nerve channel in a silicon or polymer overmold, as further described below.

FIGS. 56B-56D illustrate the configuration of the batteryless MR before the electrodes 5402 are formed around the mandrel. As shown, the batteryless MR can be initially formed as a substantially planar structure before creating the nerve channel using the mandrel. Structural members, such as tabs that can be pinched together, can extend from the outer surface of the MR. Pinching the tabs opens up the gap between the opposing ends of the electrodes and allows access to the nerve channel. In addition, a pair of Nitinol structural members 5406 at the ends of MR can be added to assist the cuff portion of the MR to adopt the appropriate channel shaped configuration when placed in the body. The Nitinol structural members can be heat set and shaped, over the mandrel or another similarly shaped mandrel for example, to adopt the channel shaped configuration when heated to body temperature.

The PCB 5400 and electrical components 5408 can form one layer and a ferrite layer 5404 can be disposed against and/or attached to the PCB layer. In some embodiments, surface mounted components can be soldered on only one side, such as the top side, using only solder. A coil 5410 for power transmission and communication can be wrapped around the PCB 5400 and ferrite 5404 layers. In some embodiments, the coil is made of gold wire or traces. Addition of the ferrite layer improves the efficiency of power transfer and communication signal strength. In other embodiments, the coil is wrapped around a ferrite core, such as a ferrite rod, which can be separate from the PCB. The use of ferrite may allow low frequency power transfer and communication.

The electrodes 5402, which may be spring cut to aid in deployment, can be attached to and/or in electrical communication with the PCB 5400. The electrodes 5402 can made of a platinum alloy (i.e., platinum-iridium) coated metal (i.e., gold traces) that can be encapsulated or sheathed within a polymer such as liquid crystal polymer (LCP). The LCP can provide the metal tracings that form the electrode with support and structure so that the electrodes can maintain the appropriate shape as defined by, for example, the mandrel. The LCP can be melted at 200° C. to encapsulate the electrodes, conductive traces, the PCB with its associated electronics, the coil, and the ferrite. The ferrite can also be coated with a polymer, such as parylene-C. The polymer coatings and/or sheath 412 provides physical support and protection for the various components and provides electrical insulation to the components and stops or reduces undesired or unintended current between electrical components and to wrong tissues in the patient's body. In addition, the polymer coatings, and particularly the LCP, can be used to embed any toxic materials in the electrical components, thereby preventing or greatly reducing the leaching of toxic materials in the patient.

In some embodiments, the batteryless MR is non-hermetic. In this embodiment, the electrodes are not encapsulated by LCP and are instead encapsulated with a standard polymer sheath.

In order to control delivery of electrical current from the electrodes, selective openings or windows 5414 can be created in the polymer coating or sheath 5412, by overmolding or selective application of the polymer, to expose a portion of the electrode. Each electrode can have one or more openings in the polymer coating to expose the platinum alloy coated metal electrode. In some embodiments, the openings can be up to about 0.5, 1.0, 1.5, 2.0, 2.5, 3.0 mm². The current density of the electrodes through these openings can be up to about 0.25, 0.5, 1.0, 1.5, 2.0 mA/mm².

FIGS. 57A-57C illustrate an embodiment of the batteryless MR in which the PCB substrate is formed from a high temperature melting point LCP 5500, which allows the electrodes 5502 that can be coated with platinum, iridium oxide, or combinations thereof, conductive traces 5510 that can be made of gold, and electronics components 5504, such as the MCU, to be embedded in the LCP substrate and/or surface mounted on the high temperature LCP substrate 5500. The high temp LCP 5500 can be melted at 200 degrees C. In some embodiments, surface mounted components can be soldered on only one side, such as the top side, using only solder. A low temperature melting point LCP 5506 can be used to cover both sides of the PCB with windows 5508 on the bottom for electrodes 5502. In some embodiments, the high temperature LCP layer can have a thickness between about 0.25 to 3 mm, or up to about 1, 2, 3, 4, or 5 mm. In some embodiments, the low temperature LCP 5506 can have a thickness of about or less than about 0.25, 0.5, 0.75, or 1 mm. In other embodiments, the electronic components can be surface mounted on a polyimide substrate and then coated with LCP. The electronic components may first be coated in Parlyene-C before adding the LCP coating.

Figure 58A:
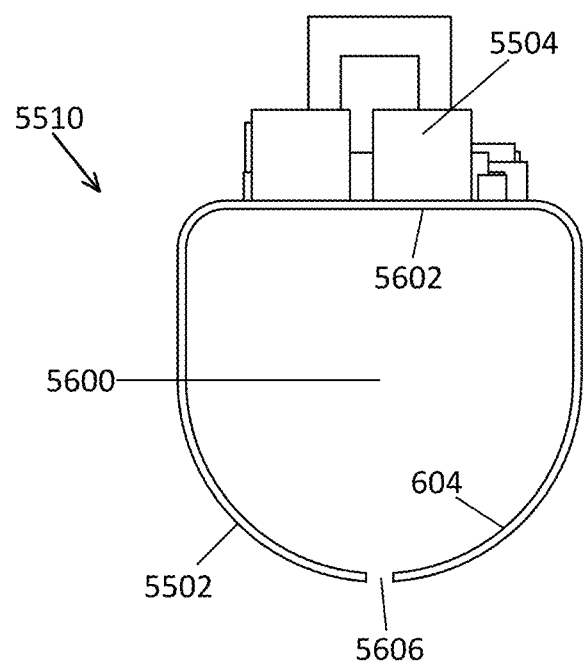
FIGS. 58A-58B illustrate the batteryless MS of FIGS. 57A-57C in a deployed configuration, which may be positioned/implanted around a nerve.
Figure 58B:
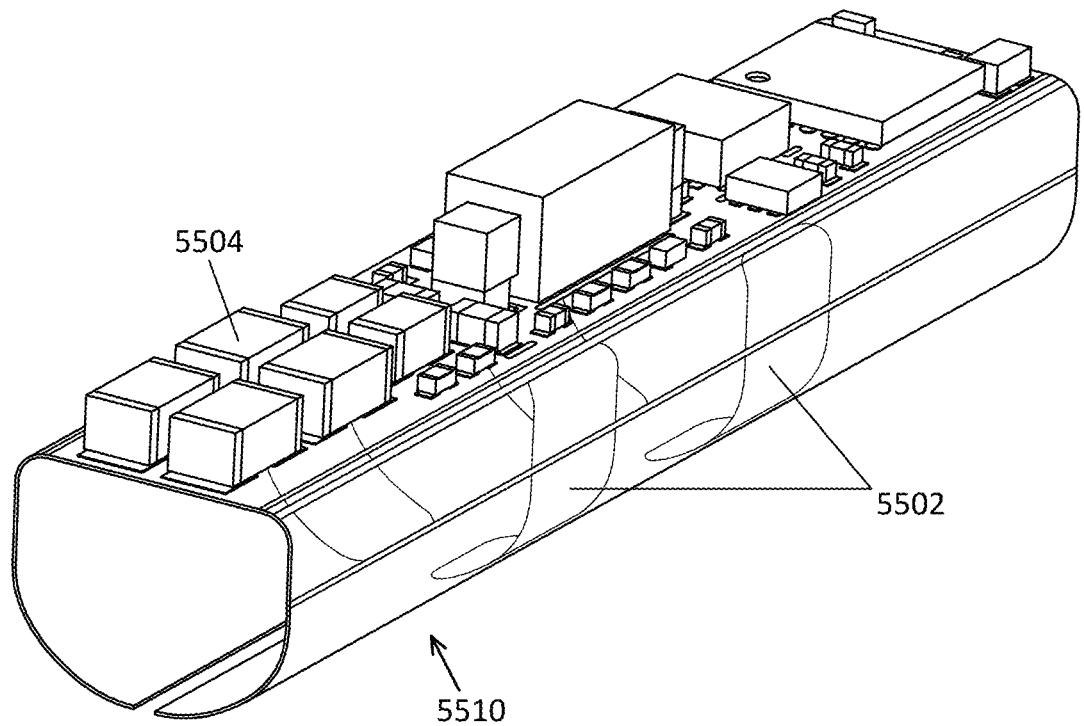

In some embodiments, the PCB 5510, electrodes 5502, and cuff portion are formed initially into a flat, planar structure, as shown in FIGS. 57A and 57B, for example, using layers of LCP as shown in FIG. 57C. Then, as shown in FIGS. 58A and 58B, the PCB 5510 can be deformed or molded around a mandrel 5600 so that it neutrally sits around the target nerve. Due to the thermoplastic properties of the LCP, the step of deforming or molding the PCB 5510 around the mandrel 5600 can be done thermally by heating the PCB 5510. In some embodiments, the mandrel 5600 can also be heated, and the mandrel may be made of metal to improve heat conductance through the mandrel. In some embodiments, the mandrel 5600 can have a flat planar portion 5602 that abuts against the portion of the PCB 5510 with the electrical components 5504, and a curved portion 5604 to which the electrodes 5502 and cuff portion of the PCB 5510 can be wrapped around. The size of the mandrel 5600 is selected so that when the electrodes 5502 and cuff portion of the PCB 5510 is wrapped around the mandrel 5600, the ends of the PCB 5510 form a small gap 5606 or a slit, which can be less than about 1, 2, 3, 4, or 5 mm or the ends can abut against one another. The gap 5606 allows access to the nerve channel and allows the implant to be placed around a nerve and also to be later removed from the nerve or repositioned along the nerve.

Figure 59A:
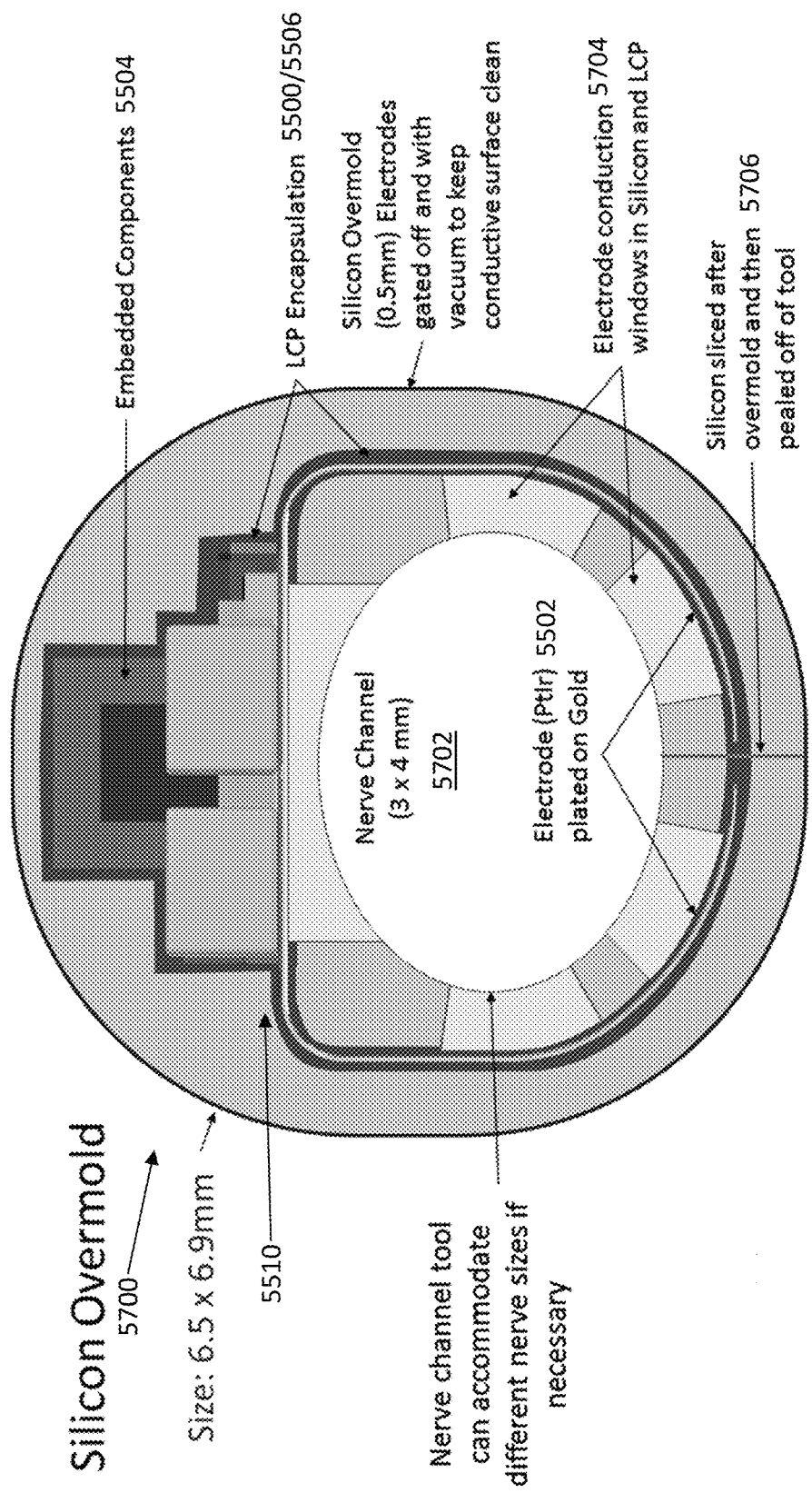
FIGS. 59A-59C illustrate a deployed batteryless MR with side "wings" or portions curved (e.g., over a nerve); the apparatus may be placed within a holder (e.g., a cuff or POD as described herein) or directly coated with an overmolding material (such as a silicone overmold, as shown).
Figure 59B:
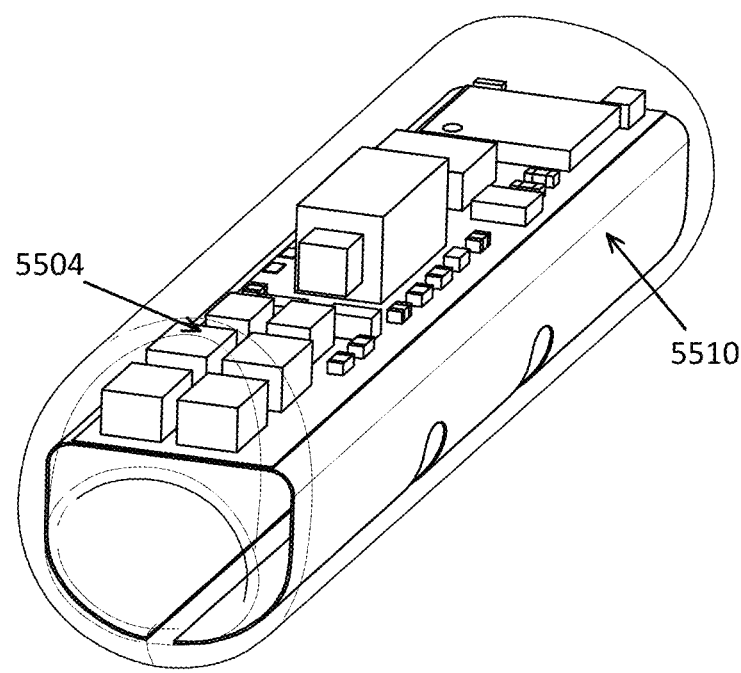
Figure 59C:
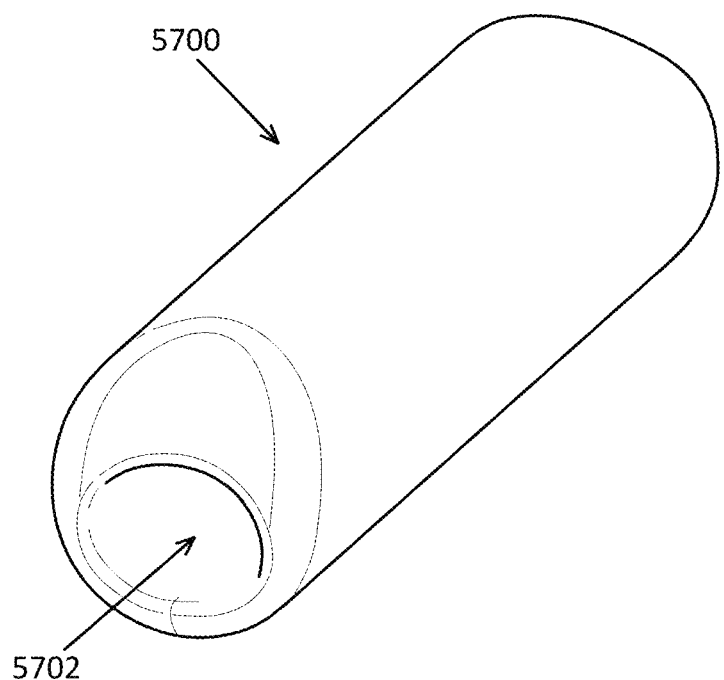

After the PCB is molded around the mandrel, the PCB can be cooled and the mandrel can be removed so that a silicon overmold 5700 can be applied over the LCP coated 5500/5506 PCB 5510 and electronics 5504, as shown in FIGS. 59A-59C. In some embodiments, another polymer, plastic, or rubber material can be used instead of silicon. The inner portion of the silicon overmold 5700 can be defined to form a nerve channel 5702 using a nerve channel tool which can be sized and shaped to accommodate different target nerve sizes. For example, the nerve channel tool can have a cross-section that is oblong, oval or ellipsoid with minor dimension of about 3 mm and a major dimension of about 4 mm to form a nerve channel for receiving the vagus nerve. For a batteryless MR, the silicon overmold 5700 can be made substantially smaller with a cross-section dimension of about 6.5 by 6.9 mm, compared to a MR with a battery, which has a cross-section dimension of about 9.4 by 11.1 mm, for example. The silicon overmold 5700 can provide a layer of silicon about 0.5 mm thick on either side of the LCP encapsulated PCB 5510. The outer surface of the silicon overmold can be made smooth and curved to be atraumatic to the patient's tissues. The silicon overmold 5700 can also be provided with electrode conduction windows 5704 that align with the electrode conduction windows in the LCP that expose a portion of the electrode 5502 for delivery of electrical stimulation. The electrodes 5502 can be gated off and with vacuum to keep the conductive surface of the electrodes clean. The silicon overmold 700 can then be sliced or formed with a slit 5706 that is aligned with the gap or slit in the cuff portion of the PCB 5510, and then the silicon overmold 5700 and encapsulated PCB 5510 forming the MR can be peeled off and removed from the nerve channel tool. The slice or gap 5706 allows the cuff portion to be opened so that the nerve can be placed within the nerve channel during implantation. In addition, the sliced overmold allows the MR to be removed from the nerve and allows the MR to be repositioned if needed, as described herein.

Figure 60A:
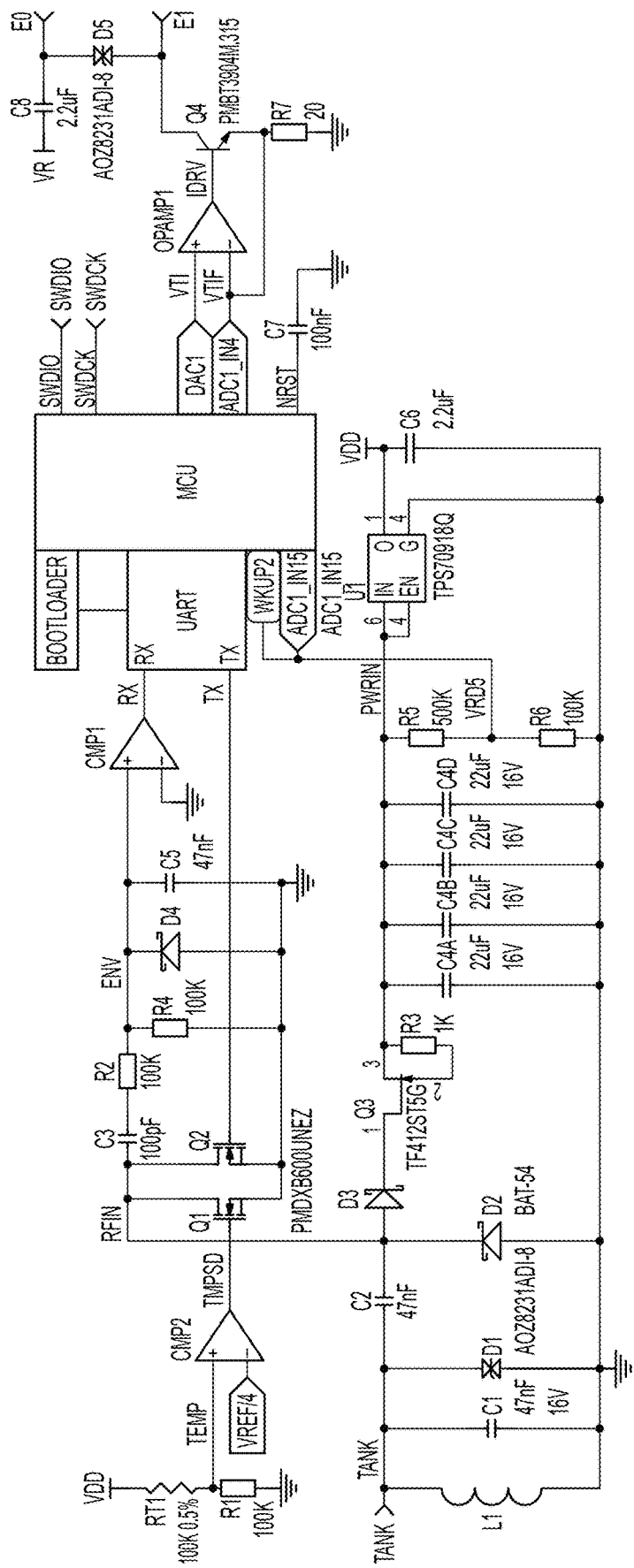
FIGS. 60A-60C show exemplary circuit diagrams of batteryless MRs as described.

FIG. 60A illustrates a circuit diagram of the batteryless and optionally non-hermetic MR illustrated in FIGS. 56A-56D. L1 & C1 form a tank circuit that resonates at a set or predetermined frequency, which can be ~131 KHz. To power and/or charge and/or communicate with the device, the charger or device communicating with the MR can send a signal with a frequency that matches the tank circuit resonance frequency. D1, which represents a TVS diode, prevents the tank circuit voltage from going beyond a set or predetermined voltage limit, which can be 16V as shown. C2, D2 (Zener diode), & D3 (Zener diode) form a voltage doubler and impedance matcher. Q3 & R4 limits current to avoid circuit chattering. C4 stores enough energy for several seconds (sub-burst) of stimulation. C4 can be a plurality of capacitors in parallel, which is shown in FIG. 60A as four capacitors (C4A, C4B, C4C, and C4D) in parallel. R5 and R6 scale down PWRIN voltage to be read by the MCU. Q1 shorts the Tank if the temperature as measured by RT1 exceeds a set or predetermined temperature, which can be 41.5 C as shown. C3, R2, R3, D4 & C5 extract the amplitude modulation (AM) modulated carrier to extract incoming data from the signal. CMP1 slices the data that feeds into the UART RX line. Q2 receives UART TX line and modulates the carrier with return data. U1 regulates PWRIN, a variable voltage that can range from 3.3-16V for example, to a set or predetermined voltage such as 1.8V to power the MCU. DAC1 drives a voltage to current converter (OPAMP1, Q4 & R7) to drive stimulation electrodes (E0, E1) where C8 protects against direct current (DC). ADC1_IN4 measures compliance voltage where impedance can be calculated. In some embodiments, the MCU stimulates the patient and communicates with the Energizer only when the Energizer is attached. In addition, RT1, R1 and CMP2 form the thermal shutdown circuitry.

Figure 60B:
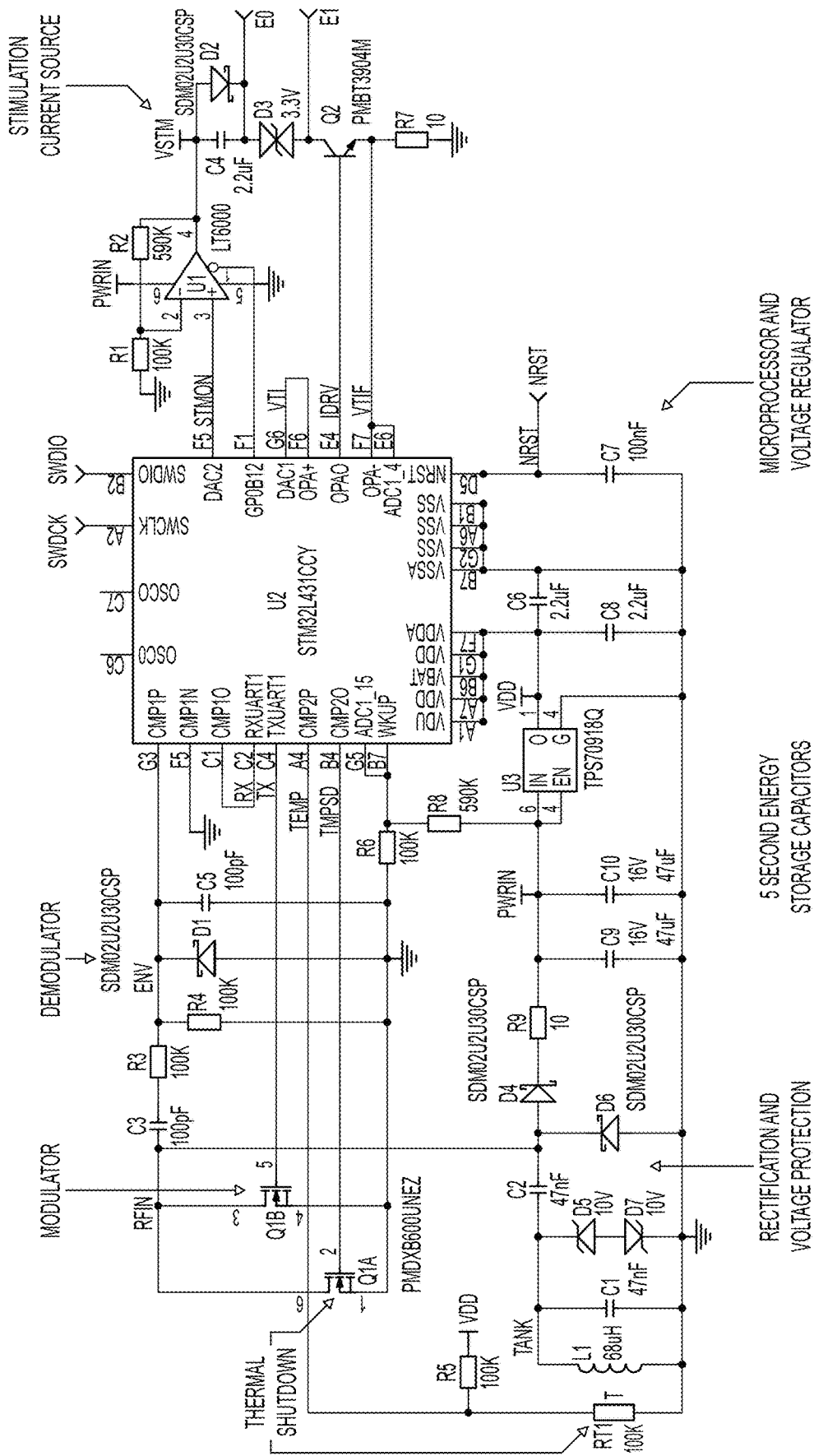

FIG. 60B illustrates an embodiment of another circuit diagram of the batteryless non-hermetic MR illustrated in FIGS. 56A-56D. The circuit diagrams illustrated in FIGS. 60A and 60B are very similar but do have some differences. For example, the embodiment illustrated in FIG. 60B stores energy in fewer capacitors (i.e., two) than shown in FIG. 60A, but the capacitors have a higher capacity (i.e., 47 uF versus 22 uF). The higher capacity capacitors are capable of providing enough energy for 5 seconds of electrical stimulation with the stimulation parameters previously described in U.S. Pat. Nos. 8,612,002 and 8,886,339, while lower capacity capacitors generally result in shorter sub-burst durations. Another difference is the thermal shutdown circuitry. In FIG. 60B, the thermal shutdown circuitry includes a thermistor RT1 that is directly integrated with the tank circuit (L1 and C1) which receives power from the energizer, whereas in FIG. 57A, the thermistor RT1 is not directly connected to the tank circuit and instead can be placed near the antenna, L1, or another portion of the MR in which it is desirable to measure the temperature, such as the electrodes, for example.

Similar to FIG. 60A, the circuit diagram shown in FIG. 60B also shows the modulator and demodulator portions of the circuit which are responsible for extracting information from and/or introducing information to the signal from the energizer. Both circuits also have a rectification and voltage protection circuit, microprocessor and voltage regulator circuit, and a stimulation current source circuit.

After implantation of the batteryless MR at or around a nerve, such as the vagus nerve, the MR can be operated by applying an RF power signal at the resonant frequency to charge up C4 to a set, desired, or predetermined voltage, such as 10V. In some embodiments, charging is relatively quick and can take about 0.5 seconds, or less than 1, 2, 3, 4, or 5 seconds. An external energizer that can be handheld or worn around the body part of the MR, such as the neck, can be used to generate the RF power signal to power and charge the MR. In some embodiments, the energizer can be a powered coil that can be worn around the body part with the MR such that the coil encircles the MR, and the energizer generates an electromagnetic field that inductively charges the MR. However, since the power requirements of the batteryless MR is generally much less than a battery based MR, a handheld energizer with a pancake coil that can be pressed against the body part with the MR may be used instead of a coil that is worn around the body part with the MR.

After the MR is charged up, the MR-MCU can start delivering the electrical stimulus to the nerve, in the form of a sub-burst for example, and can return an acknowledgement and an impedance measurement to the external energizer. The impedance measurement can be used to determine whether the electrodes are in good contact with the nerve. A higher than normal or expected impedance measurement may indicate poor electrode contact. The MR-MCU can also log the success or failure of delivering the sub-burst and can also transmit this information to the energizer. The MR-MCU can complete at least one 1-3 second stimulus sub-burst using the power stored in the array of capacitors, meaning that even if RF power transmission of the energizer fails, the delivery of the full sub-burst can be completed once the capacitors are sufficiently charged, such as being charged to about 10V. Although a 1-3 second sub-burst is described, longer sub-bursts can also be achieved by increasing the capacity of the capacitors and/or by increasing the number of capacitors in parallel. For example, if C4 (array of capacitors in parallel) is charged up to 10V by the Energizer, the Energizer or the MR-MCU itself can instruct the MR to deliver a second sub-burst immediately after delivering the first sub-burst so that a complete burst formed of back-to-back sub-bursts can be delivered. In some embodiments, more than two sub-bursts can be delivered consecutively by, for example, increasing the energy capacity of C4. After the sub-burst and/or complete burst is delivered, the MR-MCU and/or energizer can log the delivery of the stimulus for patient compliance tracking and monitoring onto non-volatile memory of the MR. In some embodiments, once a sub-burst is initiated, it goes to completion, so a shorter duration sub-burst may be preferred, such as less than about 1, 2, 3, 4, 5, 6, 7, 8, 9, or 10 seconds, since a shorter sub-burst allows the stimulation to be stopped more quickly if a problem with stimulation is detected.

Figure 60C:
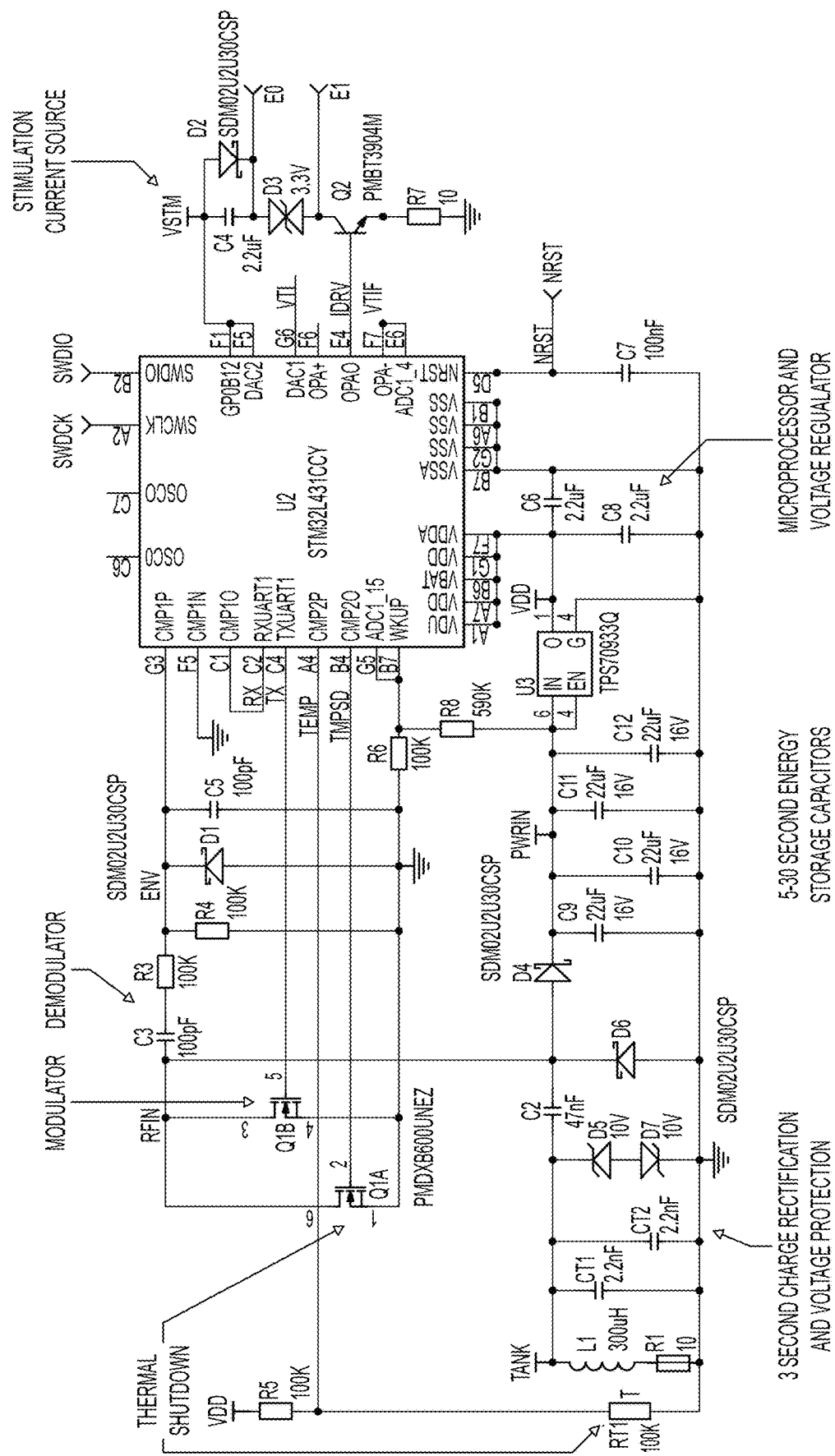

FIG. 60C illustrates yet another embodiment of a circuit diagram for a batteryless MR that is similar to the circuit diagram illustrated in FIG. 60B. Both FIGS. 60B and 60C share the same modulator, demodulator, thermal shutdown, and microprocessor and voltage regular components. There are differences in the rectification and voltage protection, the energy storage, and the stimulation current source portions of the circuit. The rectification and voltage protection circuit has been modified to provide about 3 seconds of charge rectification and voltage protection and enough stored energy to deliver about 5-30 seconds of electrical stimulation.

L1, CT1 and CT2 form a tank circuit that resonates at about 131 KHz. D5 & D7 prevents the tank from going beyond 16V. C2, D4, & D6 form at voltage doubler and impedance matcher. C9-12 stores enough energy for about 5-30 seconds of electrical stimulation, depending on the stimulation amplitude applied. R6 & R8 scale downs PWRIN voltage to be read by the MCU. Q1A shorts the Tank if the temperature as measured by RT1 exceeds a predetermined or set temperature, such as 41.5 C. C3, R2, R3, D1 & C5 extract the AM modulated carrier to extract incoming data. CMP1 slices the data that feeds into the UART RX line. Q2 receives UART TX line and modulates carrier with return data. U1 regulates PWRIN that ranges from 3.4-16V to 3.3V. DAC2 ramps voltage up to 3.3V and GPOB12 holds high during stimulation to save power and then DAC2 ramps down to 0V. DAC1 drives a voltage to current converter (OPAMP, Q4 & R7) to drive stimulation electrodes where C4 protects against DC and D2 recovers stimulation pulse. ADC1_IN4 measures compliance voltage where impedance can be calculated. The MCU stimulates the patient and communicates with the Energizer only when the Energizer is attached.

Figure 61:
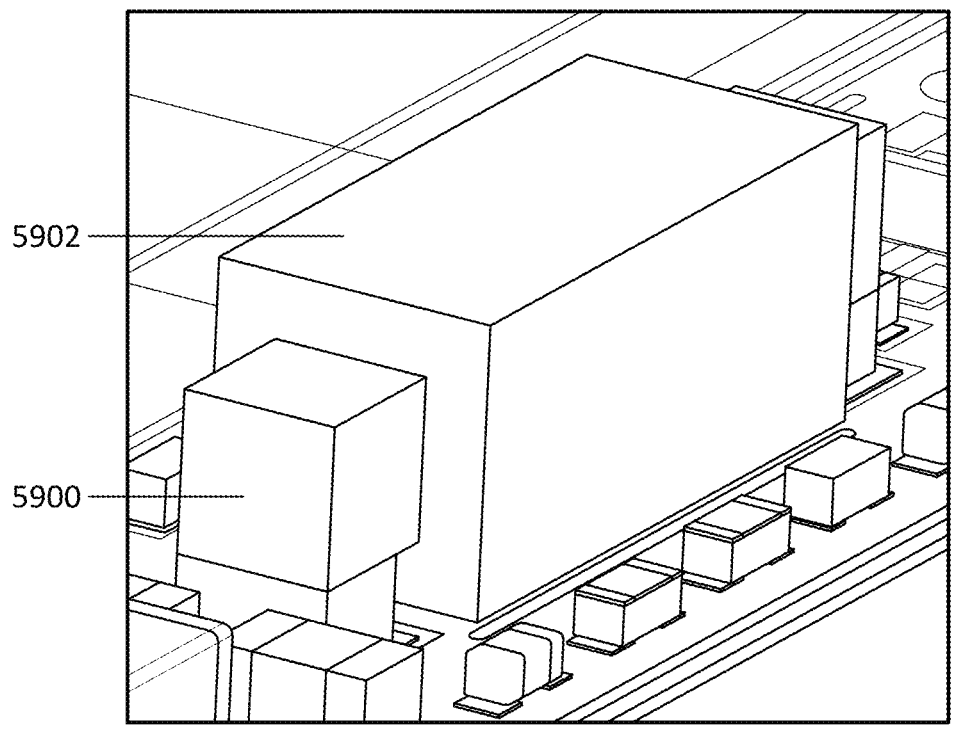
FIG. 61 illustrates a magnetic core within a coil (forming an inductive coil within the batteryless MS) that may be used as part of a batteryless MS.

In some embodiments, the power transfer and magnetics features or requirements of the MR may include, for example, selecting a shape and size for the magnetic core or ferrite 900, as shown in FIG. 61, which is compatible with a 3T magnetic field generated during MRI, which can exert a force and torque on the magnetic core of the MR. The magnetic field during MRI can also generate heating and induced voltages which need to be tolerated by the components of the magnetic core 5900 and coil 5902. For a given core with its geometric constraints, the number of turns of the wire and the gauge of the wire for the coil are selected to provide direct impedance match to load without additional matching components, which results in improved or maximum volumetric efficiency.

Figure 62:
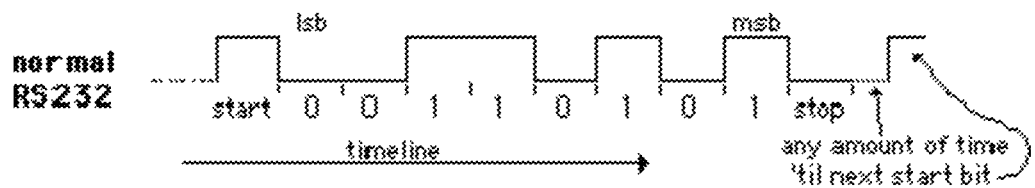
FIGS. 62 and 63 illustrate communication protocols that may be used (having low energy requirements) with any of the microstimulators described herein, including in particularly a batteryless MS.
Figure 63:
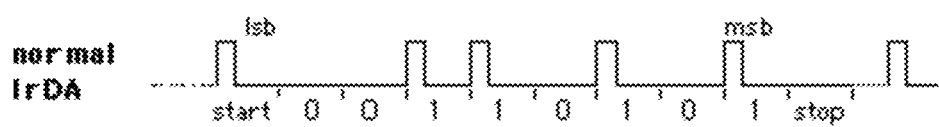
Figure 64A:
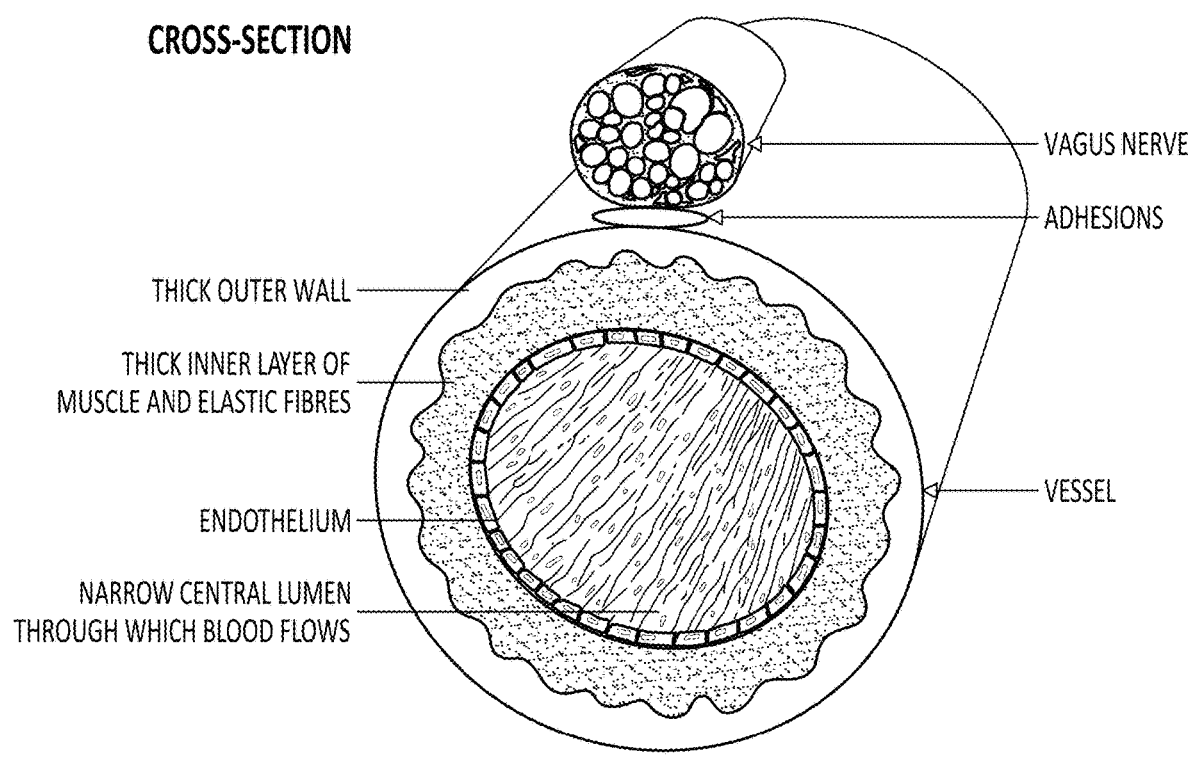
FIG. 64A illustrates the anatomy of a portion of a nerve (e.g., vagus nerve) near a vessel.
Figure 64B:
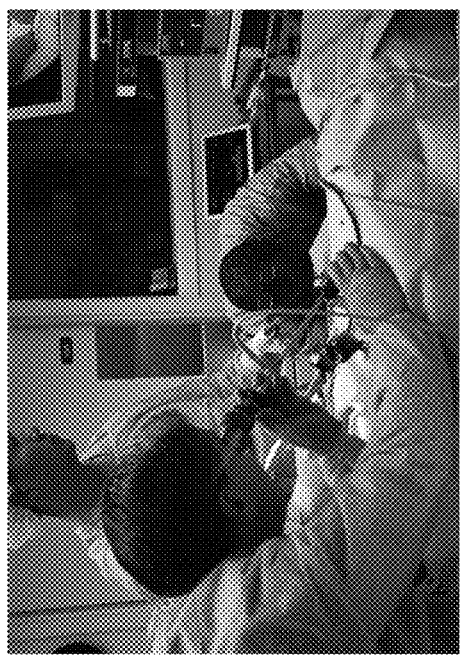
FIGS. 64B-64D illustrate one method of surgically inserting/implanting a batteryless MS apparatus as described herein.
Figure 64D:
Figure 64C:

In some embodiments, the Energizer or another computing device can communicate directly with the MCU hardware bootloader of the MR. The communications protocol can be RS232: 8 bit and parity NRZ at 2,400-4,800 bps. In some embodiments, the communications reliability can be improved by using inverse IrDA because response telemetry can reduce carrier cutout. Physical security as provided by the loop prevents unauthorized access that can result in overwritten and/or corrupted data, which is recoverable. Because the power signal is used for power transfer and communications, there is a tradeoff between power transfer and communication speed, meaning some power transfer may be sacrificed to increase communication speed. Examples of RS232 and IrDA signals for communication are illustrated in FIGS. 62 and 63, respectively.

Implantation

FIGS. 64A-64D illustrate the separation of a nerve, in this case the vagus nerve, from an adjacent blood vessel using a laparoscopic procedure. It some cases, the target nerve runs along a blood vessel and may be attached to the blood vessel, and both structures may be covered in a sheath of connective tissue. In some embodiments, the connective tissue sheath can be dissected to expose the nerve, and the nerve can be dissected and separated from the blood vessel at the implantation site before the MR is attached to the nerve. For example, in the neck the vagus nerve, the interior jugular vein, and the common carotid artery are enclosed by the carotid sheath. The carotid sheath can be cut and dissected at the implantation site to expose the vagus nerve and blood vessels. The vagus nerve can then be dissected and separated from the blood vessel within the carotid sheath, and the MR can be placed over the nerve. In some embodiments, the sheath may be dissected to expose the nerve and blood vessels, but the nerve may be left attached to the blood vessel(s) and the MR nerve channel may be sized and shaped to encompass both the nerve and blood vessel(s). In other embodiments, the sheath, nerve and blood vessels may be left untouched and the nerve channel may be sized and shaped to encompass the entire structure of the sheath, nerve, and blood vessels. In some embodiments, the preparation of the implantation site can be performed using minimally invasive surgical techniques, such as there a laparoscopic or endoscopic procedure.

The benefit of removing the sheath and optionally separating the vessel from the nerve is that such separation may allow cleaner, closer and more direct contact of the electrodes with the target nerve, which allows the nerve to be stimulated using a lower level of current and/or voltage. For example, testing has shown that removal of the carotid sheath from the vagus nerve can allow stimulation of the vagus nerve using a 5 to 10 fold lower level of current compared to stimulation through the carotid sheath. For a battery based MR, the reduction in current level and/or voltage level allows the MR to be used longer before recharge for a given battery capacity, and/or allows the MR to use a lower capacity battery which can reduce the size of the MR and reduce manufacturing costs. For a batteryless MR, lower current and/or voltage levels can reduce the number and/or capacity of the capacitors used for delivering the electrical stimulus, which can reduce the material costs and the time needed to charge the capacitors before delivering an on-demand type stimulation. Also, in general, using lower current and/or voltage to stimulate the nerve is generally desirable to reduce tissue damage and inadvertent stimulation of other nerves or tissues within or near the sheath, such as baroreceptors.

The batteryless MR can be implanted to the target nerve using various surgical procedures, including minimally invasive procedures such as a laparoscopic procedure as shown in FIGS. 65A-65D. The batteryless MR can be made substantially smaller than a MR that relies on a relatively large battery to provide enough energy for long term stimulation. This allows the batteryless MR to be delivered in a variety of different minimally invasive procedures.

For example, the batteryless MR 1300 can be delivered using a laparoscopic delivery tube 1302 with an optional removable sheath 1304, which can be used to prop open the cuff portion of the MR. The batteryless MR 1300 can be loaded within the distal end of the laparoscopic delivery tube 1302 at a temperature below body temperature, such as at ambient temperature (i.e., about 23 degrees C.) or colder. At this temperature, the Nitinol struts 1306 within the cuff portion of the MR 1300, as also shown in FIGS. 56A-56D, adopt an open delivery configuration as shown in FIG. 65B or 65C, for example, where the cuff is in an open state and the nerve channel is exposed to receive the nerve. As shown in FIG. 65C, a removable sheath 1304 can optionally be placed within the nerve channel of the MR to prop the open the nerve channel. Alternatively as shown in FIG. 65B, the cuff portion of the MR 1300 can be inverted and placed into the delivery tube 1302 to hold the MR in an open configuration. The delivery tube 1302 can then be inserted through a small incision to the target nerve 1308. Once the distal end of the delivery tube 1302 is aligned with the nerve 1308 and placed adjacent to the target nerve, the MR can be ejected or pushed out of the delivery tube or a retractable sheath can be withdrawn to release the MR from the delivery tube. The removable sheath 1304 can then be removed from the MR when the MR is correctly positioned and aligned over the nerve to allow the cuff portion of the MR to close over the nerve. As the Nitinol struts 1306 of the MR 1300 increase in temperature to body temperature (i.e., about 37 degrees C.), the cuff portion moves from an open state to a closed state. The biocompatibility, shape memory and superelastic properties of Nitinol facilitates the deployment of the MR 1300 over the nerve 1308. If the MR 1300 was properly deployed along the nerve 1308, the cuff portion will surround and encapsulate a portion of the nerve 1308 as it adopts the closed state, as shown in FIG. 65D, for example.

FIG. 66A-66C illustrates a variation of the batteryless MR discussed above in connection with FIGS. 56A-56D that is bistable. As shown in FIG. 66A, the cuff or sheath portion of the MR 1400 with the electrodes 1402 and that goes around the nerve 1404 can also be molded and formed into a tubular shape using, for example, a mandrel as described above. As shown in FIG. 60B, instead of using Nitinol struts to change the configuration of the cuff from open to closed, the tubular cuff can be unrolled and buckled off-axis or otherwise flattened and held in place in the buckled or flattened configuration using a retaining mechanism 1406, such as a clip, for example. To deploy the MR 1400, as shown in FIG. 60C, the MR 1400 is aligned with and placed against the nerve 1404. Then the retaining mechanism 1406 is removed, allowing the tubular cuff to take its natural shape around the nerve 1404.

Figure 69A:
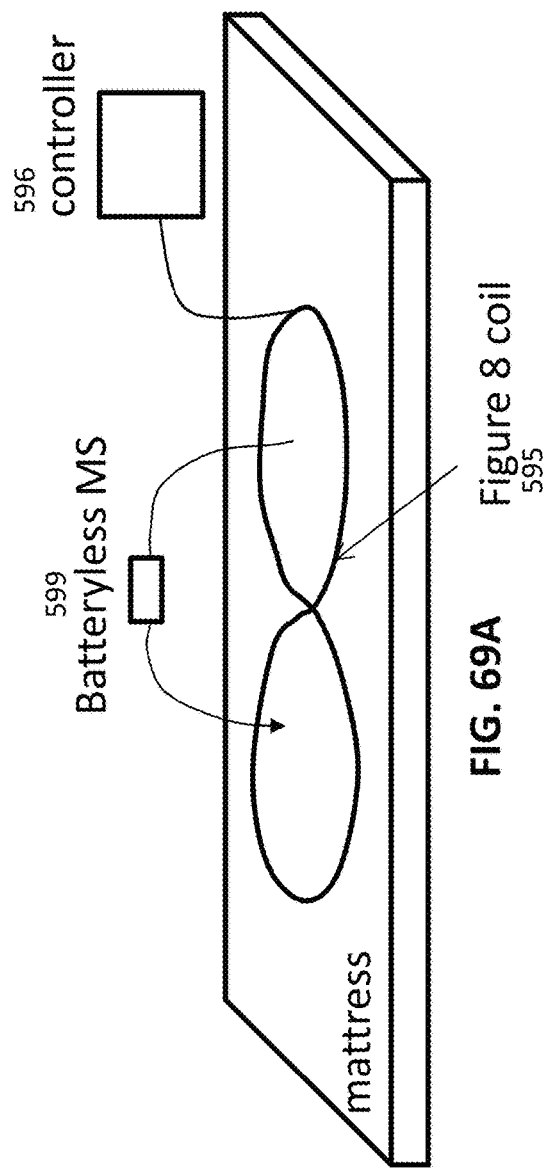
FIGS. 69A and 69B illustrate chargers (configured as pillow chargers/mattress chargers) that may be used with a batteryless implant, as described herein.
Figure 69B:
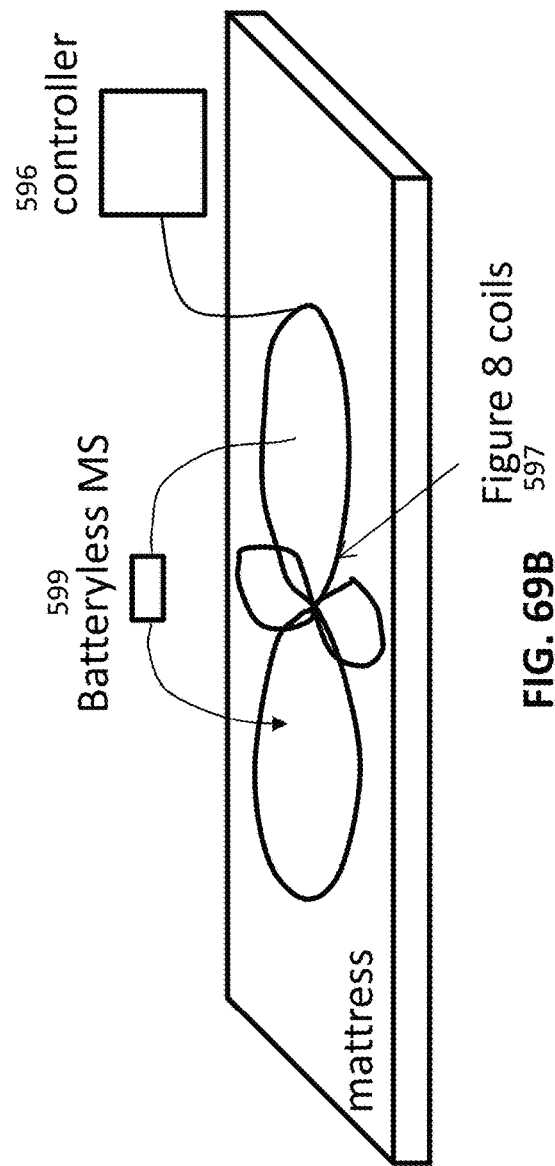

Although the laparoscopic procedures described herein can also be adapted and used for cervical placement of the MR on, for example, the cervical portion of the vagus nerve, the laparoscopic procedures are particularly suited for placement of the MR in the thorax and other areas below the neck. For example, the laparoscopic procedure can be used for placement of the MR on the sub-diaphragmatic portion of the vagus nerve. Sub-diaphragmatic placement on the vagus nerve in contrast to cervical vagal placement may result in fewer side effects such as avoiding laryngeal adverse events (change or loss of voice) and avoiding changes to the heart rate and other changes to the cardiovascular system because the stimulation site is downstream of the portion of the vagus nerve that innervates the heart. In addition, a laparoscopic procedure in the thorax, which is typically covered by clothing, avoids creating a scar on a highly visible area such as the neck. Other advantages of a laparoscopic procedure include the ability to perform the procedure in an outpatient surgery and reduced costs as compared to traditional hospital based surgery where the patient remains for one or more days and/or nights. Furthermore, sub-diaphragmatic placement may result in less undesirable muscle stimulation and the resulting pain. The laparoscopic procedure, which may be adapted for use with a MR with a battery, is particularly suited for delivering the smaller batteryless MR, which may also lack a hermetic seal that may limit the operation lifetime of the MR to about 5 to 10 years. A batteryless MR implanted within the thorax can be used with a chest strap type energizer that can be adapted from the energizer worn around the neck as previously described in U.S. Pat. Nos. 8,612,002 and 8,886,339. The chest strap energizer can have a power source and a coil that extends through the strap to encircle the patient's chest when worn. Any of the chargers described herein may be used with these devices. For example, as shown in FIGS. 69A-69B, described below, a charger configured as a mattress may be particularly useful.

Figure 67C:
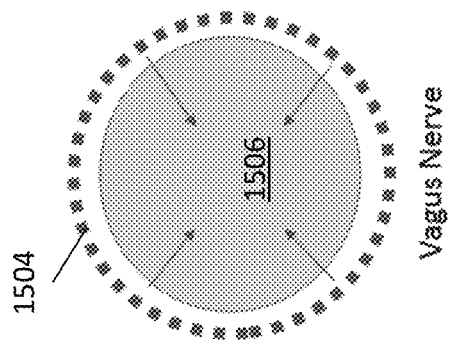
FIGS. 67A-67C illustrate a method of delivering a batteryless MS device for implantation on a nerve.
Figure 67B:
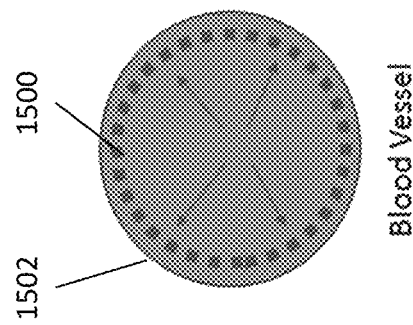
Figure 67A:
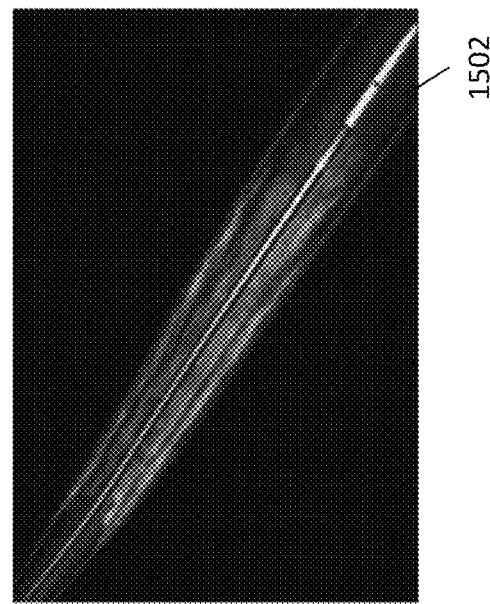

FIGS. 67A-67C illustrate at method of delivering the MR that is similar to a method of delivering a stent. FIGS. 67A and 67B illustrate that a stent 1500 can be advanced within a blood vessel 1502 to a target site and then expanded to press the stent 1500 against the wall of the vessel 1502 which anchors the stent 1500 using an outwardly applied force. To deliver the MR 1504, as shown in FIG. 65C, the MR 1504 can be advanced to the target site on the nerve 1506, and then instead of expanding the implant, the MR 1504 is disposed over the nerve 1506 to encompass the nerve within a channel to anchor the nerve by exerting an inwards force around the nerve.

FIGS. 68A-68E illustrates an embodiment of an insertion tool 1600 for placing the MR 1602 around the nerve 1604. The insertion tool 1600 has an elongate and arched MR receiving portion 1606 that can have a U-shaped cross-sectional profile. The elongate MR receiving portion 1604 can also be segmented with a plurality of transverse slits 1608 to provide the MR receiving portion with additional flexibility. As shown in FIGS. 68B and 68C, the cuff portion of the MR 1602 can be opened and placed over the U-shaped MR receiving portion 1606 such that the cuff portion wraps around the outside surface of the MR receiving portion 1606. The opening 1610 to the MR receiving portion 1606 is wide enough to encompass the anatomical structure to be encompassed by the MR cuff portion, such as the vagus nerve 1604. The insertion tool 1600 can have an elongate shaft 1612 that is movably attached to the MR receiving portion 1606, as shown in FIG. 68C. The insertion tool 1600 can also be inserted through a trocar 1614, catheter, or other access device using a minimally invasive procedure. In some embodiments, the MR 1602 can be pre-loaded on the insertion tool 1600 by the manufacturer.

After the implantation site has been prepared, by for example dissecting the nerve from the sheath and blood vessels, a trocar 1614 or catheter or other access device, which can have a lumen for receiving the insertion tool 1600, can be inserted into the patient and advanced near the target site using conventional techniques. The trocar 1614, catheter, or other access device may have already been inserted into the patient during the preparation of the implantation site, in which case the preexisting access device can be used instead. As shown in FIG. 68C, the insertion tool 1600, with the MR 1602 loaded on the MR receiving portion 1604, can be inserted through the trocar until the MR receiving portion 1606 carrying the MR 1602 is fully extended outside the trocar 1614. As shown in FIG. 68D, the MR receiving portion 1606 can then be positioned over the nerve 1604 so that the nerve 1604 is positioned inside the U-shaped portion of the MR receiving portion 1606. Next, the insertion tool 1600 is extracted while holding the MR 1602 in place over the nerve 1604 at the target implantation site.

To hold the MR in place while the insertion tool is extracted, a MR stabilizing device can be advanced to the MR to abut against the proximal end of the MR and/or to grasp a portion of the MR as the MR receiving portion of the insertion tool is retracted in a proximal direction. In some embodiments, the MR stabilizing device may be advanced over the shaft of the insertion tool and/or may be integrated into the insertion tool as a component that can be advanced and retracted relative to the shaft of the insertion tool. In some embodiments, the MR stabilizing device can have a distal end that is arched with a U-shaped cross-sectional profile that is similar in shape with the MR receiving portion, except that the U-shaped cross-sectional profile of the distal end of the MR stabilizing device can be slightly larger than the size of the MR receiving portion of the insertion tool so that the MR receiving portion can be retracted within or through the U-shaped portion of the MR stabilizing device while the MR stabilizing device abuts against the MR.

Alternatively, the MR stabilizing device can be positioned to abut against the MR during loading of the MR onto the insertion tool. The insertion tool and the MR stabilizing device can both be inserted through the access device, such as the trocar illustrated herein, and advanced to and positioned over the nerve as described herein. To deploy the MR, the MR receiving portion of the insertion tool can be retracted while the MR stabilizing device is held in place.

In some embodiments, the MR stabilizing device can have a different shaped cross-section, such as rectangular, square, or curved, that can be aligned and/or abutted against a portion of the MR, such as the portion with the PCB and electronic components.

As shown in FIG. 68E, after the insertion tool 1600 is extracted, the cuff portion of the MR 1602 can adopt a closed configuration and encircle the nerve 1604.

FIGS. 69A-69B illustrate examples of chargers that may be particularly useful in conjunction with a batteryless microstimluator. In FIG. 69A, the mattress includes a figure-8 coil 595 that allows for device communication at relatively large distances in the patient's abdomen. Stimulation from the batteryless implant 599 (shown above the mattress, where it may be when implanted into a patient's body) may therefore be performed while the patient is reclining on the mattress. The bursts of energy may be kept sort to keep the heat low, and the monitoring (e.g., heart rate monitoring, HRV) may be performed by the device itself at night while within the inductive field, allowing manual or automatic adjustments to the applied energy based on feedback from the HRV or other metrics. Data/information on the patient and/or implant may be stored in non-volatile memory within the implant and/or the charger and/or a separate controller 596 that may be wired or wireless coupled to the charger.

FIG. 69B shows another variation having multiple coils (e.g. a pair of FIG. 8 coils 579 although additional coils at other orientations may be used). As described above, the charger may rotate the field to best match the coil(s) in the implant.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for nerve stimulation, the system comprising:
a microregulator comprising:
   a receiver module configured to wirelessly receive a power signal;
   at least one pair of electrodes configured to deliver electrical stimulation to a nerve;
   a microprocessor configured to be powered by electrical energy received by the receiver module, wherein the microprocessor is configured to cause the at least one pair of electrodes to deliver the electrical stimulation to the nerve only when the power signal is being received by the receiver module; and
   a cuff configured to secure the at least one pair of electrodes against the nerve; and
a charger configured to charge the microregulator, the charger including a transmitter that is configured to generate the power signal receivable by the receiver module of the microregulator.

2. The system of claim 1, wherein the microregulator is configured for implantation into a patient's body, and wherein the charger is configured to be external to the patient's body.

3. The system of claim 1, wherein the cuff defines a nerve channel that is configured to hold the nerve within the nerve channel.

4. The system of claim 1, wherein the cuff comprises one or more conduction windows arranged to expose at least a portion of the at least one pair of electrodes for delivery of the electrical stimulation to the nerve.

5. The system of claim 1, wherein the microprocessor is configured to cause the at least one pair of electrodes to deliver the electrical stimulation for modulating chronic inflammation.

6. The system of claim 1, wherein the receiver module includes a power receiving coil, and the charger includes a transmitter coil.

7. The system of claim 1, wherein the charger is configured to be wearable by a patient.

8. The system of claim 1, wherein the charger is part of a pillow.

9. The system of claim 1, wherein the receiver module, the microprocessor, and at least a portion of the at least one pair of electrodes are encapsulated by a liquid crystal polymer, wherein the liquid crystal polymer is encapsulated by the cuff.

10. The system of claim 1, wherein the microregulator further comprises a non-volatile memory in communication with the microprocessor, wherein the microprocessor is programmed to log dose compliance in the non-volatile memory.

11. The system of claim 1, wherein the microregulator is batteryless.

12. The system of claim 1, further comprising an external controller module that is configured to allow a patient to set one or more parameters stimulation parameters.

13. The system of claim 1, further comprising tester configured to test operation of the microregulator implanted in a patient.

14. A system for nerve stimulation, the system comprising:
a microregulator configured for implantation into a patient's body, the microregulator comprising:
   a receiver module configured to wirelessly receive a power signal;
   at least one pair of electrodes configured to deliver electrical stimulation to a nerve;
   a microprocessor configured to be powered by electrical energy received by the receiver module, wherein the microprocessor is configured to cause the at least one pair of electrodes to deliver the electrical stimulation to the nerve only when the power signal is being received by the receiver module, wherein the electrical stimulation is configured to treat inflammation and/or an inflammatory disorder; and
   a cuff configured to secure the at least one pair of electrodes against the nerve; and
an external charger configured to charge the microregulator when the microregulator is implanted within the patient's body, the charger including a transmitter that is configured to generate the power signal receivable by the receiver module of the microregulator.

15. The system of claim 14, wherein the electrical stimulation has an amplitude of up to 3 mA and a duration of up to 30 seconds.

16. The system of claim 14, wherein the electrical stimulation is delivered as a plurality of sub-bursts, each sub-burst having a duration of about 1-5 seconds.

17. The system of claim 14, wherein the nerve is the vagus nerve in a cervical region of the neck, a sub-diaphragmatic portion of the vagus nerve, or a peripheral nerve.

18. The system of claim 14, wherein the cuff defines a nerve channel that is configured to hold the nerve within the nerve channel.

19. The system of claim 14, wherein the cuff comprises one or more conduction windows arranged to expose at least a portion of the at least one pair of electrodes for delivery of the electrical stimulation to the nerve.

20. The system of claim 14, wherein the charger is part of a pillow or is configured to be wearable by a patient.

* * * * *